United States Patent
Tanaka et al.

(10) Patent No.: US 9,670,129 B2
(45) Date of Patent: Jun. 6, 2017

(54) PROCESS FOR PREPARING 4-HYDROXYBUTYL ACRYLATE

(71) Applicant: OSAKA ORGANIC CHEMICAL INDUSTRY LTD., Osaka-shi, Osaka (JP)

(72) Inventors: Yukio Tanaka, Kashiwara-shi (JP); Kohei Okamura, Kashiwara-shi (JP); Keisuke Ito, Kashiwara-shi (JP)

(73) Assignee: OSAKA ORGANIC CHEMICAL INDUSTRY LTD., Osaka-shi (JP)

( * ) Notice: Subject to any disclaimer, the term of this patent is extended or adjusted under 35 U.S.C. 154(b) by 0 days.

(21) Appl. No.: 14/516,979

(22) Filed: Oct. 17, 2014

(65) Prior Publication Data

US 2015/0126766 A1 May 7, 2015

Related U.S. Application Data

(63) Continuation of application No. PCT/JP2013/061460, filed on Apr. 18, 2013.

(30) Foreign Application Priority Data

| Apr. 21, 2012 | (JP) | ................................ | 2012-097208 |
| May 9, 2012 | (JP) | ................................ | 2012-107166 |
| Jun. 13, 2012 | (JP) | ................................ | 2012-133380 |
| Jul. 13, 2012 | (JP) | ................................ | 2012-157301 |
| Aug. 27, 2012 | (JP) | ................................ | 2012-186422 |
| Feb. 4, 2013 | (JP) | ................................ | 2013-019961 |
| Feb. 15, 2013 | (JP) | ................................ | 2013-027400 |

(51) Int. Cl.
*C07C 67/40* (2006.01)
*C07C 67/03* (2006.01)

(52) U.S. Cl.
CPC .............. *C07C 67/40* (2013.01); *C07C 67/03* (2013.01)

(58) Field of Classification Search
CPC ............................. C07C 69/32; C07C 69/533
See application file for complete search history.

(56) References Cited

U.S. PATENT DOCUMENTS

2007/0270606 A1  11/2007  Riondel et al.

FOREIGN PATENT DOCUMENTS

| CN | 101074195 A | 11/2007 |
| DE | 1518572 A1 | 1/1969 |
| EP | 663386 A1 * | 7/1995 |
| EP | 0 881 209 A1 | 2/1998 |
| EP | 0 906 902 A2 | 7/1999 |
| JP | 46-39848 | 11/1971 |
| JP | 8-268938 A | 10/1996 |
| JP | 11-43466 A | 2/1999 |
| JP | 2000-63371 A | 2/2000 |
| JP | 2000-128831 A | 5/2000 |
| JP | 2000-159726 A | 6/2000 |
| JP | 2000-159727 A | 6/2000 |
| JP | 2000-319225 A | 11/2000 |
| JP | 2003-155263 A | 5/2003 |
| JP | 2003155263 A * | 5/2003 |
| JP | 2004-189650 A | 7/2004 |
| JP | 3585989 B2 | 11/2004 |
| JP | 2007-254384 A | 4/2007 |
| JP | 2007-161636 A | 6/2007 |
| JP | 2008-231003 A | 2/2008 |
| WO | 2010/136696 A1 | 2/2010 |

OTHER PUBLICATIONS

English Translation of JP 2003-155263, 6 pages, Published May 27, 2003.
Office Action dated Jun. 25, 2015, issued in corresponding Chinese Patent Application No. 201380019941.3 (6 pages).
Extended (Supplementary) European Search Report dated Feb. 25, 2016, issued in counterpart application No. 13778712.3.

* cited by examiner

*Primary Examiner* — Sudhakar Katakam
(74) *Attorney, Agent, or Firm* — Westerman, Hattori, Daniels & Adrian, LLP

(57) ABSTRACT

A process for preparing 4-hydroxybutyl acrylate by transesterifying an alkyl acrylate with 1,4-butanediol in the presence of a dialkyltin oxide such that each of the alkyl groups has 4 to 8 carbon atoms, characterized in that the amount of the dialkyltin oxide is adjusted to 0.00001 to 0.01 moles per one mole of the alkyl acrylate.

8 Claims, No Drawings

PROCESS FOR PREPARING 4-HYDROXYBUTYL ACRYLATE

TECHNICAL FIELD

The present invention relates to a process for preparing 4-hydroxybutyl acrylate. More specifically, the present invention relates to a process for preparing 4-hydroxybutyl acrylate, a process for preparing a hydroxyalkyl acrylate, and a process for preparing a (meth)acrylate.

A hydroxyalkyl acrylate is useful for, for example, raw materials such as fibers, fiber treating agents, dyeability-improving agents for fibers, coatings, anti-static additives, adhesives, pressure sensitive additives, paper strength additives, raw materials for resins such as ion-exchange resins, and precursors for producing various organic compounds. 4-Hydroxybutyl acrylate is useful for raw materials such as coatings for automobiles, coatings for building materials, coating agents for electronic materials, photosensitive resin compositions and pressure sensitive additives for medical uses. A (meth)acrylate is useful for, for example, raw materials such as (meth)acrylic resins, surface active agents, additives and coatings, although its uses depend on its kind.

Incidentally, in this description, "methyl(meth)acrylate" means "methyl acrylate" and/or "methyl methacrylate". Therefore, methyl acrylate and methyl methacrylate can be used alone respectively, or can be used together. Also, "(meth)acrylate" means "acrylate" and/or "methacrylate". Therefore, the acrylate and the methacrylate can be used alone respectively, or can be used together.

BACKGROUND ART

As a process for preparing 4-hydroxybutyl acrylate, there has been known a process for preparing 4-hydroxybutyl acrylate, which includes the esterification reaction through dehydration of 1,4-butanediol and acrylic acid with a catalyst such as sulfonic acid or para-toluene sulfonic acid (see, for example, Patent Literature 1). However, the above-mentioned process has some defects such that the amount of by-products is great, that the process necessitates a complicated neutralizing step because an acid is used as a catalyst, and that a large amount of salts generated in the neutralizing step become wastes. In addition, the above-mentioned process has some defects such that unreacted acrylic acid remains in the resulting 4-hydroxybutyl acrylate in an amount which exerts baneful influence for using the 4-hydroxybutyl acrylate as a raw material for pressure sensitive additives for medical uses, coating agents for electronic materials and the like.

As a method for solving the defects in the above-mentioned process, there have been proposed a method for preparing a hydroxyalkyl monoacrylate, which includes the esterification reaction of an acrylic acid derivative with an alkane diol with a stannoxane compound as a reaction catalyst, to give a hydroxyalkyl monoacrylate (see, for example, Patent Literature 2), a method for preparing 4-hydroxybutyl acrylate, which includes transesterification reaction of 1,4-butanediol and methyl methacrylate in the presence of a stannoxane catalyst as a reaction catalyst, to give 4-hydroxybutyl acrylate (see, for example, column [0020] of Patent Literature 3 and columns [0033]-[0034] of Patent Literature 4), and the like. However, acid components such as acrylic acid remain in acrylates obtained in these methods in an amount which imparts stimulation to a skin, and which would cause corrosion. Therefore, it cannot be said that the acrylate is suitable for a raw material of pressure sensitive additives for medical uses, coating agents for electronic materials and the like.

As a method for removing a free carboxylic acid contained in the resulting hydroxyalkyl acrylate, there has been proposed a method which includes carrying out the transesterification reaction of an alkane diol with an acrylate with a distannoxane compound as a reaction catalyst, and contacting a solution of an organic solvent containing the resulting hydroxyalkyl acrylate and a free carboxylic acid with an alkaline aqueous solution (see, for example, Patent Literature 5). However, there are some defects in the above-mentioned method, such that productivity of the hydroxyalkyl acrylate is low, because the method necessitates an alkaline aqueous solution which hydrolyzes the hydroxyalkyl acrylate.

Also, it has been known to use a dialkyltin oxide such as dibutyltin oxide or di-tert-butyltin oxide as a catalyst for transesterification (see, for example, column [0004] of Patent Literature 6 and claim 1 of Patent Literature 7). The dialkyltin oxide is an attractive catalyst, because the dialkyltin oxide is excellent in catalytic activity even when its amount is mall, and is relatively inexpensive. However, it is considered that it is difficult to use the dialkyltin oxide as a catalyst, because the dialkyltin oxide is difficultly separated by an extraction operation when 4-hydroxybutyl acrylate is prepared by the transesterification reaction of 1,4-butanediol and methyl acrylate (see, for example column [0079] of Patent Literature 2 and column [0007] of Patent Literature 6). In addition, disproportionation reaction of the resulting 4-hydroxybutyl acrylate represented by the formula:

[Chem. 1]

occurs due to the alkyltin oxide contained in the 4-hydroxybutyl acrylate, to generate 1,4-butanediol diacrylate as a by-product. This by-product, 1,4-butanediol diacrylate has a boiling point which is near to the boiling point of 4-hydroxybutyl acrylate. In addition, self-polymerization of 1,4-butanediol diacrylate easily occurs due to the presence of the alkyltin oxide as a catalyst. Moreover, a crosslinking reaction of 1,4-butanediol diacrylate easily occurs, because the 1,4-butanediol diacrylate has two acrylate groups in its molecule. Therefore, it has been thought that the separation of the by-product, 1,4-butanediol diacrylate is considerably difficult by a purification method such as distillation.

Also, when a hydroxyalkyl acrylate is prepared by a transesterification method, methanol is distilled off, and contains not only n-hexane which is an azeotropic solvent but also methyl acrylate which is a raw material. Therefore, there has been proposed that water is added to this methanol, and the resulting aqueous methanol solution is separated from the starting methyl acrylate and n-hexane by liquid-liquid separation, to collect the starting methyl acrylate (see, for example, Patent Literature 8). However, water cannot be easily separated from the aqueous methanol solution. Therefore, the aqueous methanol solution is currently discarded by incineration, nevertheless the methanol contained in the aqueous methanol solution is valuable. When the above-mentioned operation for treatment is carried out, there arise some defects such that a special incinerator such as an incinerator of waste water for incinerating the aqueous methanol solution is necessitated, and that running cost increases because a large amount of energy is required for incinerating the aqueous methanol solution.

In addition, as a method for efficiently separating methanol from the mixture of methyl(meth)acrylate and methanol with a reactor equipped with a distillation column, there has been proposed a method which includes using an azeotropic solvent which forms an azeotropic mixture together with methanol, recirculating a part of a condensate made of vapor which is distilled from the overhead of the distillation column, separating the residual condensate into two layers, supplying the upper layer of the two layers to the middle portion of the distillation column, taking out the lower layer from the distillation column, and collecting methyl(meth)acrylate from the bottom of the reactor (see, for example, Patent Literature 9). According to the above-mentioned method, methyl(meth)acrylate which exists in the bottom portion of the reactor can be collected. However, after the collection of the methyl(meth)acrylate, the methyl(meth)acrylate remaining inside the reactor cannot be collected.

Also, as a process for preparing an objective(meth)acrylate by the transesterification reaction of an alkyl(meth)acrylate used as a raw material and an alcohol, there has been proposed a process for preparing a (meth)acrylate, which includes carrying out a transesterification reaction in the presence of an azeotropic solvent which forms an azeotropic mixture together with an alkyl alcohol which is formed as a by-product, removing the alkyl alcohol which is formed as a by-product together with the azeotropic solvent from the discharge port positioning at the upper portion of the distillation column, controlling the temperature of the vapor discharging from the discharge port to a temperature not lower than the azeotropic temperature of the alkyl alcohol which is generated as a by-product and an azeotropic solvent which forms an azeotropic mixture together with the alkyl alcohol, and not higher than the temperature which is 2° C. higher than the azeotropic temperature, and controlling the temperature of the bottom of the distillation column to a temperature which is 10° C. lower than the boiling point of the azeotropic solvent or more and not higher than the boiling point of the azeotropic solvent (see, for example, Patent Literature 10). According to the above-mentioned process for preparing the (meth)acrylate, it is thought that a side reaction, Michael addition reaction can be suppressed, and a (meth)acrylate can be prepared in high productivity. However, after the preparation of an objective(meth)acrylate, the alkyl(meth)acrylate used as a raw material remains in the reaction system, and a method for efficiently collecting the remaining alkyl(meth)acrylate which is a raw material has not yet been examined.

Accordingly, in a process for preparing a (meth)acrylate which is prepared by a transesterification method with methyl(meth)acrylate used as a raw material, there has been desired to develop a process for preparing a (meth)acrylate by using a transesterification method, which enables the collection of the (meth)acrylate which is a raw material remaining in the reaction system in high efficiency.

Also, when a (meth)acrylate is prepared by transesterification reaction of methyl(meth)acrylate and an alcohol, methyl alcohol which is generated as a by-product is generally removed from the reaction system in order to efficiently prepare the (meth)acrylate. A method for removing methyl alcohol which is generated as a by-product during the preparation of the (meth)acrylate is generally classified into the following two methods:

The first method is a method which includes using a reactor equipped with a distillation column when the transesterification reaction of methyl(meth)acrylate and an alcohol is carried out, forming an azeotropic mixture of methyl (meth)acrylate and methyl alcohol, and taking out the resulting azeotropic mixture from the overhead of the distillation column (see, for example, working example 4 of Patent Literature 11). The azeotropic mixture obtained by this method is generally used as a raw material for preparing methyl methacrylate in order to effectively use the azeotropic mixture. When the above-mentioned azeotropic mixture is used as a raw material for preparing(meth)acrylate, methyl (meth)acrylate is effectively used as a raw material. However, methyl alcohol which is a by-product has a defect such that the methyl alcohol hinders the transesterification reaction of methyl(meth)acrylate and an alcohol.

The second method is a method which includes using a reactor equipped with a distillation column when the transesterification reaction of methyl(meth)acrylate and an alcohol is carried out, adding a hydrocarbon compound which forms an azeotropic mixture with methyl alcohol at a temperature lower than the boiling point of methyl(meth)acrylate to a reaction system of methyl(meth)acrylate and an alcohol, and discharging the azeotropic mixture of methyl alcohol and the hydrocarbon compound at an azeotropic temperature of methyl alcohol and the hydrocarbon compound from the overhead of the distillation column (see, for example, working example 5 of Patent Literature 9). In this method, a preferred reaction solvent includes aliphatic saturated hydrocarbon compounds having 5 to 8 carbon atoms, such as n-pentane, n-hexane, n-heptane, n-octane, 2,3-dimethylbutane, 2,5-dimethylhexane and 2,2,4-trimethylpentane, and the like (see, for example, columns [0017]-[0018] of Patent Literature 9). According to the second method, for example, when n-hexane is used as a reaction solvent, methyl(meth)acrylate which is a raw material is included in the azeotropic mixture other than n-hexane and methyl alcohol, which is discharged from the overhead of the distillation column. However, it is difficult to separate the methyl(meth)acrylate from n-hexane and methyl alcohol. Therefore, according to the second method, the azeotropic mixture is treated as a waste, fuel and the like, nevertheless the azeotropic mixture includes methyl(meth)acrylate which is useful as a raw material of a (meth)acrylate.

As a method for effectively using the azeotropic mixture obtained in the second method, it is thought that a part of the distillate which is distilled from the overhead of the distillation column is recirculated to the overhead of the distillation column, water is added to the remaining distillate to separate the distillate into two layers, supplying the upper layer of the two layers, which mainly contains a reaction solvent, to the middle portion of the distillation column, and the lower layer of the two layers, which mainly contains methyl alcohol and water, is disposed as a waste (see, for example, claim 1 of Patent Literature 2). According to the second method, however, it is difficult to extract methyl (meth)acrylate only to the upper layer, and methyl(meth)acrylate is included in the lower layer. Therefore, methyl (meth)acrylate contained in the lower layer is disposed as a waste in the end.

PRIOR ART DOCUMENTS

Patent Documents

Patent Literature 1: German Patent No. 1518572
Patent Literature 2: Japanese Unexamined Patent Publication No. Hei 11-43466
Patent Literature 3: Japanese Unexamined Patent Publication No. 2003-155263
Patent Literature 4: Japanese Unexamined Patent Publication No. 2007-161636

Patent Literature 5: Japanese Unexamined Patent Publication No. 2000-159727
Patent Literature 6: Japanese Unexamined Patent Publication No. 2000-128831
Patent Literature 7: Japanese Examined Patent Publication No. Sho 46-39848
Patent Literature 8: Japanese Patent No. 3585989
Patent Literature 9: Japanese Unexamined Patent Publication No. Hei 8-268938
Patent Literature 10: Japanese Unexamined Patent Publication No. 2004-189650
Patent Literature 11: Japanese Unexamined Patent Publication No. 2000-319225

SUMMARY OF THE INVENTION

Problems to be Solved by the Invention

The present invention has been accomplished in view of the foregoing prior art.

An object of the present invention is to provide a process for preparing 4-hydroxybutyl acrylate, in which 4-hydroxybutyl acrylate can be efficiently prepared by carrying out the transesterification reaction of 1,4-butanediol and an alkyl acrylate, and moreover a catalyst for transesterification which is used in the transesterification reaction can be efficiently collected.

Another object of the present invention is to provide a process for preparing 4-hydroxybutyl acrylate having a low content of acid components, which can be suitably used as a raw material of pressure sensitive additives for medical uses, which is easily influenced adversely by acids, coating agents for electronic materials, photosensitive resin compositions, and the like.

The other object of the present invention is to provide a process for preparing 4-hydroxybutyl acrylate, in which even though an alkyltin oxide is used as a catalyst for transesterification when 4-hydroxybutyl acrylate is prepared by carrying out the transesterification reaction of 1,4-butanediol and an alkyl acrylate, 4-hydroxybutyl acrylate can be efficiently prepared in a low content of 1,4-butanediol diacrylate which is generated as a by-product.

The other object of the present invention is to provide a process for preparing a hydroxyalkyl acrylate, in which an alcohol which is generated as a by-product when a hydroxyalkyl acrylate is prepared by a transesterification method can be efficiently collected.

The other object of the present invention is to provide a process for preparing a (meth)acrylate by a transesterification method, in which methyl(meth)acrylate is used as a raw material, and a (meth)acrylate is prepared by a transesterification method, wherein an objective(meth)acrylate is prepared, and then methyl(meth)acrylate which is a raw material remaining in the reaction system can be efficiently collected.

The other object of the present invention is to provide a process for preparing a (meth)acrylate, in which methyl(meth)acrylate can be efficiently used when the (meth)acrylate is prepared by a transesterification method using methyl(meth)acrylate as a raw material.

Means for Solving the Problems

Conventionally, when a dialkyltin oxide is used as a catalyst for transesterification in the transesterification reaction of 1,4-butanediol and an alkyl acrylate, it has been thought that the separation of the dialkyltin oxide from the resulting 4-hydroxybutyl acrylate is difficult by an extraction operation. Therefore, it has been thought that the dialkyltin oxide is not suitable as a catalyst for transesterification when the transesterification reaction of 1,4-butanediol and an acrylate is carried out (see, for example, column [0079] of the above-mentioned Patent Literature 2 and column [0007] of the above-mentioned Patent Literature 6).

The transesterification reaction of 1,4-butanediol and an alkyl acrylate has been earnestly studied, focusing on a dialkyltin oxide which has been conventionally thought not to be suitable as a catalyst for transesterification when the transesterification reaction of 1,4-butanediol and an acrylate is carried out. As a result, it has been found out a quite novel process for preparing 4-hydroxybutyl acrylate, in which 1,4-butanediol and an acrylate can be efficiently reacted with each other even when 1,4-butanediol is reacted with an alkyl acrylate in the presence of a dialkyltin oxide, in which the dialkyltin oxide can be easily removed from the resulting 4-hydroxybutyl acrylate, and in which the collected dialkyltin oxide can be reused in the transesterification reaction of 1,4-butanediol and an alkyl acrylate. The first present invention has been accomplished based upon the above-mentioned facts.

Therefore, the first present invention relates to (1) a process for preparing 4-hydroxybutyl acrylate, including carrying out the transesterification reaction of 1,4-butanediol and an alkyl acrylate, characterized in that a catalyst for transesterification containing a dialkyltin oxide having an alkyl group of 4 to 18 carbon atoms is used, and the amount of the dialkyltin oxide having an alkyl group of 4 to 18 carbon atoms is adjusted to 0.00001 to 0.01 moles per one mole of the alkyl acrylate when the transesterification reaction of 1,4-butanediol and an alkyl acrylate is carried out in the presence of the dialkyltin oxide;

(2) the process for preparing 4-hydroxybutyl acrylate according to the above-mentioned item (1), wherein a reaction mixture obtained by the transesterification reaction of 1,4-butanediol and an alkyl acrylate is mixed with an extractant containing water and an aliphatic hydrocarbon compound, to extract 4-hydroxybutyl acrylate into a water layer, thereafter the water layer is mixed with an extractant containing an aromatic hydrocarbon compound, to extract 4-hydroxybutyl acrylate contained in the water layer into the aromatic hydrocarbon compound to collect 4-hydroxybutyl acrylate;

(3) the process for preparing 4-hydroxybutyl acrylate according to the above-mentioned item (1) or (2), wherein the dialkyltin dioxide is collected from the reaction mixture containing 4-hydroxybutyl acrylate obtained by the transesterification reaction of 1,4-butanediol and the alkyl acrylate, the collected dialkyltin oxide is reused as a catalyst for transesterification when the transesterification reaction of 1,4-butanediol and an alkyl acrylate is carried out; and (4) the process for preparing 4-hydroxybutyl acrylate according to any one of the above-mentioned items (1) to (3), wherein the alkyl acrylate is an alkyl acrylate represented by the formula (I);

[Chem. 2]

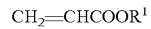

$$CH_2=CHCOOR^1 \qquad (I)$$

wherein $R^1$ is an alkyl group having 1 to 4 carbon atoms. The second present invention relates to (1) a process for preparing 4-hydroxybutyl(meth)acrylate, including carrying out the transesterification reaction of 1,4-butanediol and an alkyl(meth)acrylate, characterized in that the transesterification of 1,4-butanediol and the alkyl(meth)acrylate is carried out in the presence of a catalyst for transesterification represented by the formula (II);

[Chem. 3]

wherein each of $R^2$ and $R^3$ is independently an alkyl group having 1 to 18 carbon atoms, an aryl group having 6 to 12 carbon atoms or an aralkyl group having 7 to 12 carbon atoms, X is an alkali metal atom or an alkaline earth metal, n is a mummer which shows the atomic value of X;

(2) the process for preparing 4-hydroxybutyl(meth)acrylate according to the above-mentioned item (1), wherein the amount of the catalyst for transesterification represented by the formula (II) is 0.00001 to 0.01 moles per one mole of (meth)acrylate;

(3) the process for preparing 4-hydroxybutyl(meth)acrylate according to the above-mentioned item (1) or (2), wherein the reaction mixture obtained by the transesterification reaction of 1,4-butanediol and the alkyl (meth)acrylate is mixed with an extractant containing water and an aliphatic hydrocarbon compound, to extract 4-hydroxybutyl acrylate into a water layer, thereafter the water layer is mixed with an extractant containing an aromatic hydrocarbon compound, to extract the 4-hydroxybutyl acrylate contained in the water layer into the aromatic hydrocarbon compound, to collect 4-hydroxybutyl acrylate;

(4) the process for preparing 4-hydroxybutyl(meth)acrylate according to any one of the above-mentioned items (1) to (3), wherein the catalyst for transesterification represented by the formula (II) is collected from the reaction mixture containing 4-hydroxybutyl(meth)acrylate obtained by the transesterification reaction of 1,4-butnediol and the alkyl (meth)acrylate, the collected catalyst for transesterification represented by the formula (II) is reused as a catalyst for transesterification when the transesterification reaction of 1,4-butanediol and an alkyl(meth)acrylate is carried out; and (5) the process for preparing 4-hydroxybutyl(meth)acrylate according to any one of the above-mentioned items (1) to (4), wherein the alkyl(meth)acrylate is represented by the formula (III);

[Chem. 4]

$$CH_2=CR^4COOR^5 \quad (III)$$

wherein $R^4$ is a hydrogen atom or methyl group, and $R^5$ is an alkyl group having 1 to 4 carbon atoms.

The third present invention relates to
(1) a process for preparing 4-hydroxybutyl acrylate, including carrying out the transesterification reaction of 1,4-butanediol and an alkyl acrylate to prepare 4-hydroxybutyl acrylate, characterized in that the transesterification reaction of 1,4-butanediol and an alkyl acrylate is carried out in the presence of a catalyst for transesterification, thereafter extracting 4-hydroxybutyl acrylate from the resulting reaction mixture containing 4-hydroxybutyl acrylate, to collect 4-hydroxybutyl acrylate;
(2) the process for preparing 4-hydroxybutyl acrylate according to the above-mentioned item (1), wherein the reaction mixture obtained by carrying out the transesterification reaction of 1,4-butanediol and the alkyl acrylate is mixed with an extractant containing water and an aliphatic hydrocarbon compound, 4-hydroxybutyl acrylate is extracted into a water layer, thereafter the water layer is mixed with an extractant containing an aromatic hydrocarbon compound, and the 4-hydroxybutyl acrylate contained in the water layer is extracted into the aromatic hydrocarbon, to collect the 4-hydroxybutyl acrylate;

(3) the process for preparing 4-hydroxybutyl acrylate according to the above-mentioned item (2), wherein the reaction mixture is mixed with an extractant containing water and an aliphatic hydrocarbon compound, 4-hydroxybutyl acrylate is extracted into a water layer, thereafter the water layer is contacted with an ion exchange resin, and then the water layer is mixed with an extractant containing an aromatic hydrocarbon compound; and (4) 4-hydroxybutyl acrylate obtained by the transesterification reaction of 1,4-butanediol and an alkyl acrylate, characterized in that the content of acrylic acid is not more than 50 ppm.

The fourth present invention relates to a process for preparing 4-hydroxybutyl acrylate, including carrying out the transesterification reaction of 1,4-butanediol and an alkyl acrylate, characterized in that a dialkyltin oxide is used as a catalyst for transesterification; the transesterification reaction of 1,4-butanediol and an alkyl acrylate is carried out in the presence of the alkyltin oxide; the resulting reaction mixture containing 4-hydroxybutyl acrylate is extracted with an alicyclic or aromatic hydrocarbon compound and water as an extractant at a temperature of 15 to 35° C.; the resulting water layer is extracted with an aromatic hydrocarbon compound at a temperature of 15 to 65° C. from the aliphatic or alicyclic hydrocarbon compound layer and the water layer; and the resulting aromatic hydrocarbon layer is collected from the aromatic hydrocarbon layer and the water layer.

The fifth present invention relates to
(1) a process for preparing a hydroxyalkyl acrylate, including carrying out the transesterification reaction of a polyhydric alcohol and an alkyl acrylate to give a hydroxyalkyl acrylate, characterized in that an alcohol which is generated as a by-product when the transesterification reaction of a polyhydric alcohol and an alkyl acrylate is carried out is collected by using a polyhydric alcohol;

(2) the process for preparing a hydroxyalkyl acrylate according to the above-mentioned item (1), wherein the transesterification reaction of a polyhydric alcohol and an alkyl acrylate is carried out in the presence of an organic solvent which is incompatible to the polyhydric alcohol; an azeotropic mixture containing an alcohol which is generated as a by-product when the transesterification reaction is carried out and the organic solvent is distilled away from the reaction system of the transesterification reaction; thereafter the distilled azeotropic mixture is mixed with a polyhydric alcohol; the resulting alcohol solution containing the alcohol generated as a by-product and the polyhydric alcohol is separated from the resulting mixture; and the alcohol generated as a by-product is collected from the separated alcohol solution;

(3) the process for preparing a hydroxyalkyl acrylate according to the above-mentioned item (2), wherein the polyhydric alcohol which is used in the transesterification reaction is an aliphatic polyhydric alcohol having 6 to 8 carbon atoms, and the organic solvent which is incompatible to the polyhydric alcohol is at least one hydrocarbon compound selected from the group consisting of aliphatic hydrocarbon compounds having 6 to 8 carbon atoms and alicyclic hydrocarbon compounds having 6 to 8 carbon atoms;

(4) the process for preparing a hydroxyalkyl acrylate according to any one of the above-mentioned items (1) to (3), wherein the polyhydric alcohol which is used when the polyhydric alcohol is mixed with the azeotropic mixture is the same kind as the polyhydric alcohol which is used in the transesterification reaction; and (5) the process for preparing a hydroxyalkyl acrylate according to any one of the above-mentioned items (2) to (4), wherein the polyhydric alcohol is collected from the alcohol solution, and the collected polyhydric alcohol is used as a polyhydric alcohol which is used in a transesterification reaction.

The sixth present invention relates to (1) a process for preparing a (meth)acrylate, which includes using methyl (meth)acrylate as a raw material, and carrying out the transesterification reaction of the methyl (meth)acrylate and an alcohol which corresponds to an objective(meth)acrylate, to give an objective(meth)acrylate, characterized in that a reactor having a distillation column is used as a reactor; when the transesterification reaction of methyl(meth)acrylate and an alcohol which corresponds to an objective (meth)acrylate is carried out in the reactor, an azeotropic solvent which is capable of forming an azeotropic mixture with the methyl(meth) acrylate at a temperature of not higher than the boiling point of methyl(meth)acrylate is used as an azeotropic solvent; after the transesterification reaction of methyl (meth)acrylate and the alcohol which corresponds to the objective (meth)acrylate, the resulting reaction mixture is further heated; and vapor containing unreacted methyl (meth)acrylate is taken out from the upper portion of the distillation column;

(2) the process for preparing the (meth)acrylate according to the above-mentioned item (1), wherein the azeotropic solvent is at least one solvent selected from the group consisting of cyclohexane and n-hexane;

(3) the process for preparing the (meth)acrylate according to the above-mentioned item (1) or (2), wherein when the transesterification reaction of methyl(meth)acrylate and an alcohol which corresponds to the objective (meth) acrylate is carried out, vapor is taken out from the upper portion of the distillation column; the vapor obtained is condensed; a part of the obtained condensate is returned to the distillation column, and the remaining of the condensate is removed from the reactor, to control the temperature of the upper portion of the distillation column to an azeotropic temperature of the alcohol and the azeotropic solvent;

(4) the process for preparing the (meth)acrylate according to the above-mentioned item (3), wherein water is added to the condensate which is removed from the reactor; the resulting mixture is separated into two layers of an upper layer and a lower layer; and the upper layer which is separated from the two layers is returned to the distillation column;

(5) the process for preparing the (meth)acrylate according to the above-mentioned item (3) or (4), wherein water is added to the condensate which is removed from the reactor; the resulting mixture is separated into two lays of an upper layer and a lower layer; the lower layer separated from the two layers is further charged to the distillation column to distill the lower layer; vapor containing methyl (meth)acrylate and methyl alcohol which is generated as a by-product, and vapor containing methyl alcohol which is generated as a by-product in the transesterification reaction as major components are taken out from the upper portion of the distillation column, respectively;

(6) the process for preparing the (meth)acrylate according to the above-mentioned item (5), wherein the vapor containing methyl(meth)acrylate, methyl alcohol which is generated as a by-product and an azeotropic solvent is used as a raw material when the transesterification reaction of methyl(meth)acrylate and the above-mentioned alcohol is carried out; and (7) the process for preparing the (meth)acrylate according to any one of the above-mentioned items (1) to (6), wherein after the transesterification reaction of methyl(meth)acrylate and an alcohol which corresponds to the objective (meth)acrylate, vapor containing unreacted methyl(meth) acrylate which is taken out from the upper portion of the distillation column by further heating the reaction mixture is condensed, and the resulting condensate is used as a raw material in the transesterification of methyl (meth) acrylate and the above-mentioned alcohol.

The seventh present invention relates to (1) a process for preparing a (meth)acrylate which includes using methyl (meth)acrylate as a raw material and carrying out a transesterification reaction, characterized in that when the transesterification reaction of methyl(meth) acrylate and an alcohol is carried out, isohexane and cyclohexane are used in combination as a reaction solvent, and (2) the process according to the above-mentioned item (1), wherein the transesterification reaction of methyl(meth) acrylate and an alcohol is carried out by using a reactor equipped with a distillation column; vapor discharged from the overhead of the distillation column is condensed; the resulting condensate is separated into two layers; the upper layer of the two layers being separated is supplied to the distillation column.

Effects of the Invention

According to the process for preparing a 4-hydroxybutyl acrylate of the first present invention, there are exhibited excellent effects such that 4-hydroxybutyl acrylate can be efficiently prepared by carrying out the transesterification reaction of 1,4-butanediol and an alkyl acrylate, and moreover a catalyst for transesterification which is used in the transesterification reaction can be efficiently collected.

According to the process for preparing 4-hydroxybutyl (meth)acrylate of the second present invention, there are exhibited excellent effects such that 4-hydroxybutyl(meth) acrylate can be efficiently prepared by carrying out the transesterification reaction of 1,4-butanediol and an alkyl (meth)acrylate, and moreover, a catalyst for the transesterification reaction, which is used in the transesterification reaction, can be efficiently collected and reused.

According to the third present invention, there is provided 4-hydroxybutyl acrylate having a low content of acid components, which can be suitably used as a raw material of pressure sensitive additives for medical uses which are easily influenced adversely by acids, coating agents for electronic materials, photosensitive resin compositions, and the like.

According to the process for preparing 4-hydroxybutyl acrylate of the fourth present invention, there are exhibited excellent effects such that even though an alkyltin oxide is used as a catalyst for transesterification when 4-hydroxyethyl butyl acrylate is prepared by carrying out the transesterification reaction of 1,4-butanediol and an alkyl acrylate, 4-hydroxybutyl acrylate can be efficiently prepared in a low content of 1,4-butanediol diacrylate which is a by-product.

According to the process for preparing a hydroxyalkyl acrylate of the fifth present invention, there are exhibited excellent effects such that an alcohol which is generated as a by-product when a hydroxyalkyl acrylate is prepared by a transesterification method can be efficiently collected.

According to the process for preparing a (meth)acrylate of the sixth present invention, there are exhibited excellent effects such that in a process for preparing a (meth)acrylate in which methyl(meth)acrylate is used as a raw material, and in which a (meth)acrylate is prepared by a transesterification method, after an objective (meth)acrylate is prepared, methyl(meth)acrylate remaining as a raw material in the reaction system can be efficiently collected.

MODES FOR CARRYING OUT THE INVENTION

[The First Invention]

The first invention is described below.

The process for preparing 4-hydroxybutyl acrylate according to the first present invention is a process for preparing 4-hydroxybutyl acrylate, including carrying out the transesterification reaction of 1,4-butanediol and an alkyl acrylate, characterized in that a catalyst for transesterification containing a dialkyltin oxide having an alkyl group of 4 to 18 carbon atoms is used, and the amount of the dialkyltin oxide having an alkyl group of 4 to 18 carbon atoms is adjusted to 0.00001 to 0.01 moles per one mole of the alkyl acrylate when the transesterification reaction of 1,4-butanediol and an alkyl acrylate is carried out in the presence of the dialkyltin oxide.

In the present invention, first of all, the transesterification reaction of 1,4-butanediol and an alkyl acrylate is carried out.

The alkyl acrylate includes, for example, methyl acrylate, ethyl acrylate, propyl acrylate, n-butyl acrylate, isobutyl acrylate, tert-butyl acrylate, and the like. These alkyl acrylates can be used alone, respectively or at least two kinds thereof can be used in combination. Among the alkyl acrylates, from the viewpoint of the efficient separation of the resulting 4-hydroxybutyl acrylate from the alkyl acrylate, an alkyl acrylate represented by the formula (I):

[Chem. 5]

$$CH_2=CHCOOR^1 \quad (I)$$

wherein $R^1$ is an alkyl group having 1 to 4 carbon atoms is preferred, the alkyl acrylate in which $R^1$ is an alkyl group having 1 to 3 carbon atoms is more preferred, and methyl acrylate is furthermore preferred.

The amount of the alkyl acrylate per one mole of 1,4-butanediol is preferably at least 0.5 moles from the viewpoint of increase in reaction rate, and preferably at most 5 moles, more preferably at most 3 moles from the viewpoint of decrease in the amount of the unreacted alkyl acrylate.

When the transesterification reaction of 1,4-butanediol and an alkyl acrylate is carried out, a catalyst for transesterification containing a dialkyltin oxide having 4 to 18 carbon atoms is used. There is one of great characteristics of the present invention in that the catalyst for transesterification containing a dialkyltin oxide having 4 to 18 carbon atoms is used.

When a catalyst for transesterification containing a dialkyltin oxide is used, according to prior art, it has been considered that it will be difficult to remove dibutyltin oxide from the resulting 4-hydroxybutyl acrylate. In contrast, according to the present invention, nevertheless a dialkyltin oxide having 4 to 18 carbon atoms, which is one of the dialkyltin oxides, is used, there are exhibited excellent effects such that 4-hydroxybutyl acrylate can be efficiently prepared, and moreover, a catalyst for transesterification, which is used in the transesterification reaction, can be efficiently collected.

In the present invention, as a catalyst for transesterification, a dialkyltin oxide having 4 to 18 carbon atoms is used, from the viewpoint that the transesterification reaction of 1,4-butanediol and an alkyl acrylate is accelerated, and that a catalyst for transesterification can be easily removed from the resulting 4-hydroxybutyl acrylate.

The dialkyltin oxide having 4 to 18 carbon atoms has two alkyl groups which can be the same with each other, or can be different from each other.

The dialkyltin oxide having 4 to 18 carbon atoms includes, for example, dialkyltin oxides having an alkyl group of 4 to 18 carbon atoms, such as dibutyltin oxide, dioctyltin oxide and dilauryltin oxide. These dialkyltin oxides can be used alone respectively, or at least two kinds thereof can be used in combination.

Among the dialkyltin oxides having 4 to 18 carbon atoms, a dialkyltin oxide having an alkyl group of 4 to 12 carbon atoms is preferable, and dioctyltin oxide and dilauryltin oxide are more preferable, from the viewpoint that the transesterification reaction of 1,4-butanediol and an alkyl acrylate is accelerated, and that the dialkyltin oxide having an alkyl group of 4 to 18 carbon atoms is easily removed from the resulting 4-hydroxybutyl acrylate.

The amount of the dialkyltin oxide having 4 to 18 carbon atoms per one mole of the alkyl acrylate is at least 0.00001 moles, preferably at least 0.0001 mole, from the viewpoint of efficient preparation of 4-hydroxybutyl acrylate, and at most 0.01 moles, preferably at most 0.005 moles, from the viewpoint of efficient removal of dibutyltin oxide from the resulting 4-hydroxybutyl acrylate and efficient collection of the dialkyltin oxide having 4 to 18 carbon atoms.

When 1,4-butanediol is reacted with the alkyl acrylate, it is preferred that 1,4-butanediol is reacted with the alkyl acrylate in the presence of a reaction inhibitor from the viewpoint of suppression of polymerization of the alkyl acrylate.

The polymerization inhibitor includes, for example, N-oxy radical compounds such as 4-hydroxy-2,2,6,6-tetramethylpiperidine-N-oxyl, 4-acetoamino-2,2,6,6-tetramethylpiperidine-N-oxyl, 4-benzoyloxy-2,2,6,6-tetramethylpiperidine-N-oxyl, 4-oxo-2,2,6,6-tetramethylpiperidine-N-oxyl and 2,2,6,6-tetramethylpiperidine-N-oxyl; phenol compounds such as paramethoxyphenol, 2,2'-methylenebis (4-ethyl-6-tert-butylphenol), 2.6-ditert-butyl-4-methylphenol, 2.6-ditert-butyl-4-methylphenol, 2,6-ditert-butyl-N,N-dimethylamino-p-cresol, 2,4-dimetyl-6-tert-butylphenol, 4-tert-butylcatechol, 4,4'-thio-bis(3-methyl-6-tert-butylphenol) and 4,4'-butylidene-bis(3-methyl-6-tert-butylphenol); quinine compounds such as methoquinone, hydroquinone, 2,5-ditert-butylhydroquinone, 2,6-ditert-butylhydroquinone and benzoquinone; cuprous chloride; copper dialkyldithiocarbamates such as copper dimethyldithiocarbamate; amino compound such as phenothiazine, N,N'-diphenyl-p-phenylenediamine, phenyl-β-naphthylamine, N,N-diβ-naphthyl-p-phenylenediamine and N-phenyl-N'-isopropyl-p-phenylenediamine; hydroxylamine compounds such as 1,4-dihydroxy-2,2,6,6-tetramethylpiperidine, 1-hydroxy-2,2,6,6-tertamethylpiperidine, 1-hydroxy-2,2,6,6-tetramethylpiperidine and 4-hydroxy-2,2,6,6-tetrametylpiperidine; and the like. The present invention is not limited only to those exemplified ones. These polymerization inhibitors can be used alone respectively, or at least two kinds thereof can be used in combination.

The amount of the polymerization inhibitor per 100 parts by mass of the alkyl acrylate is preferably at least 0.001 parts by mass, more preferably at least 0.005 parts by mass, furthermore preferably at least 0.01 parts by mass from the viewpoint of suppression of polymerization of the alkyl acrylate, and preferably at most 5 parts by mass, more preferably at most 3 parts by mass, and furthermore preferably at most 1 part by mass from the viewpoint of increase in purity of 4-hydroxybutyl acrylate.

Incidentally, when 1,4-butanediol is reacted with the alkyl acrylate, an organic solvent can be used.

The organic solvent is preferably an organic solvent which is inactive in the reaction system of the transesterification reaction. Preferred organic solvents include, for example, aliphatic hydrocarbon compounds such as n-hexane, n-heptane and n-octane; alicyclic hydrocarbon compounds such as cyclohexane and methylcyclohexane; aromatic hydrocarbon compounds such as benzene, toluene and xylene; ether compounds such as tetrahydrofuran; organic chlorine compounds such as dichloromethane and 1,1-dichloroethane; aromatic nitro compounds such as nitrobenzene; organic phosphorus compounds such as triethyl phosphate; organic sulphur compounds such as dimethyl sulfoxide; and the like. The present invention is not limited only to those exemplified ones. These organic solvents can be used alone respectively, or can be used in combination.

The amount of the organic solvent is not particularly limited, and can be usually 5 to 200 parts by mass or so per 100 parts by mass of the total amount of 1,4-butanediol and the alkyl acrylate.

When the transesterification reaction of 1,4-butanediol and the alkyl acrylate is carried out, the reaction temperature is preferably at lowest 30° C., and more preferably at lowest 50° C. from the viewpoint of increase in reaction rate, and preferably at highest 150° C. from the viewpoint of inhibition of polymerization of the resulting 4-hydroxybutyl acrylate.

When the transesterification reaction of 1,4-butanediol and the alkyl acrylate is carried out, the atmosphere is preferably an atmosphere containing oxygen from the viewpoint of inhibition of polymerization of the alkyl acrylate, and more preferably a gas containing oxygen in a content of from 5% by volume to atmospheric concentration of oxygen from the viewpoint of enhancement of safety. Also, the pressure of the atmosphere is usually atmospheric pressure, and can be increased or reduced. For example, when the pressure of the atmosphere is reduced, there is a merit such that a side reaction can be suppressed, because the reaction temperature can be lowered.

When the transesterification reaction of 1,4-butanediol and the alkyl acrylate is carried out, the reaction time cannot be absolutely determined because the reaction time differs depending on the amounts of 1,4-butanediol and the alkyl acrylate, reaction temperature and the like. Therefore, the reaction time is usually controlled so that the transesterification reaction is completed. The end point of the transesterification reaction can be confirmed by, for example, gas chromatography, liquid chromatography and the like.

The transesterification reaction of 1,4-butanediol and the alkyl acrylate can be carried out by using a rectifying tower, a fluidized bed, a fixed bed, a reaction distillation column or the like, and the present invention is not limited only to those exemplified ones. In addition, the transesterification reaction of 1,4-butanediol and the alkyl acrylate can be carried out by any of a continuous method and a batch method.

In the progress of the transesterification reaction of 1,4-butanediol and the alkyl acrylate, an alcohol is generated as a by-product. It is usually preferred that the alcohol which is generated as a by-product is removed from the reaction system in order to accelerate the reaction. The alcohol which is generated as a by-product can be removed from the reaction system as, for example, an azeotropic mixture with an acrylate or a suitable solvent.

After the transesterification reaction of 1,4-butanediol and the alkyl acrylate is carried out in the presence of the dialkyltin oxide having 4 to 18 carbon atoms, the dialkyltin oxide having 4 to 18 carbon atoms can be collected from the resulting reaction mixture by means of, for example, distillation.

Also, an objective 4-hydroxybutyl acrylate can be collected from the resulting reaction mixture by the distillation of an unreacted acrylate and an alcohol from the reaction mixture. The removal of the unreacted acrylate and the alcohol can be carried out by means of, for example, distillation, extraction and the like.

More specifically, the resulting 4-hydroxybutyl acrylate can be collected from the resulting reaction mixture, for example, by mixing the reaction mixture obtained by the transesterification reaction of 1,4-butanediol and the alkyl acrylate with an extractant containing water and an aliphatic hydrocarbon compound to extract 4-hydroxybutyl acrylate to a water layer, and thereafter, mixing the water layer with an extractant containing an aromatic hydrocarbon compound to extract 4-hydroxybutyl acrylate contained in the water layer to the aromatic hydrocarbon compound.

When the reaction mixture is mixed with an extractant containing water and the aliphatic hydrocarbon compound, 4-hydroxybutyl acrylate contained in the reaction mixture can be extracted to the water layer, and 1,4-butanediol diacrylate which is generated as a by-product can be extracted to the aliphatic hydrocarbon compound layer. Therefore, the water layer containing 4-hydroxybutyl acrylate can be collected by separating the water layer from the aliphatic hydrocarbon compound layer.

The aliphatic hydrocarbon compound includes, for example, aliphatic hydrocarbon compounds having 6 to 12 carbon atoms, such as cyclohexane, n-hexane, n-heptane, n-octane, n-decane, isohexane, isooctane and isodecane, and the present invention is not limited only to those exemplified ones. Incidentally, in this description, the aliphatic hydrocarbon compound includes the concept that the aliphatic hydrocarbon compound contains a hydrocarbon compound having an alicyclic structure, such as cyclohexane. The extractant containing water and the aliphatic hydrocarbon compound may contain an aromatic hydrocarbon compound within the scope in which an object of the present invention is not hindered.

The amount of the aliphatic hydrocarbon compound and water cannot be absolutely determined because the amount differs depending on the amount of the reaction mixture and the like. It is preferred that the amount is appropriately controlled to an amount which is suitable for extracting 4-hydroxybutyl acrylate contained in the reaction mixture to the water layer, and separating the aliphatic hydrocarbon compound layer from the water layer. In addition, the temperature during the above-mentioned extracting operation is not particularly limited, and is usually 5 to 50° C. or so.

Next, the water layer to which 4-hydroxybutyl acrylate is extracted is mixed with an extractant containing an aromatic hydrocarbon compound to extract the 4-hydroxybutyl acrylate contained in the water layer to an aromatic hydrocarbon compound layer, and the aromatic hydrocarbon compound layer is separated from the water layer to collect the aromatic hydrocarbon compound layer containing 4-hydroxybutyl acrylate.

The aromatic hydrocarbon compound includes, for example, benzene, toluene, xylene, ethyl benzene and the like, and the present invention is not limited only to those exemplified ones. Incidentally, the extractant containing the aromatic hydrocarbon compound may contain an aliphatic hydrocarbon compound, water and the like within a scope which does not hinder an object of the present invention.

The amount of the aromatic hydrocarbon compound cannot be absolutely determined, because the amount differs depending on the amount of the water layer which is separated from the above-mentioned aliphatic hydrocarbon compound layer. It is preferred that the amount is appropriately controlled to an amount which is suitable for extracting 4-hydroxybutyl acrylate contained in the water layer to the aromatic hydrocarbon layer, and separating an aromatic hydrocarbon compound layer from the water layer. The temperature during the above-mentioned extracting operation is not particularly limited, and is usually preferably 5 to 50° C. or so.

The 4-hydroxybutyl acrylate contained in the above-mentioned aromatic hydrocarbon compound layer can be collected by, for example, evaporation of the aromatic hydrocarbon compound and the like. The temperature during the removal of the aromatic hydrocarbon compound from the aromatic hydrocarbon compound layer is not particularly limited, and is usually preferably 20 to 150° C. or so. The 4-hydroxybutyl acrylate obtained in the above can be purified by distillation, washing and the like as occasion demands.

On the other hand, the aliphatic hydrocarbon compound layer contains 1,4-butanediol diacrylate which is generated as a by-product. The aliphatic hydrocarbon compound layer also contains a dialkyltin oxide having an alkyl group of 4 to 18 carbon atoms other than the 1,4-butanediol diacrylate. Therefore, from the viewpoint of effective use of the dialkyltin oxide having an alkyl group of 4 to 18 carbon atoms, the dialkyltin oxide having an alkyl group of 4 to 18 carbon atoms can be collected from the aliphatic hydrocarbon compound layer by distillation, condensation, washing and the like.

In the present invention, the catalytic activity of the collected dialkyltin oxide having an alkyl group of 4 to 18 carbon atoms is not so lowered, and is maintained. Therefore, the dialkyltin oxide having an alkyl group of 4 to 18 carbon atoms can be reused as a catalyst for transesterification when the transesterification reaction of 1,4-butanediol and an alkyl acrylate is carried out. Accordingly, the collected dialkyltin oxide having an alkyl group of 4 to 18 carbon atoms can be reused as a catalyst for transesterification when the transesterification reaction of 1,4-butanediol and an alkyl acrylate is carried out, and the transesterification reaction of 1,4-butanediol and an alkyl acrylate can be carried out in the presence of the collected dialkyltin oxide having an alkyl group of 4 to 18 carbon atoms. At that time, it is preferred that the collected dialkyltin oxide having an alkyl group of 4 to 18 carbon atoms is reused after the reaction system of the transesterification reaction of 1,4-butanediol and an alkyl acrylate is dried so that the water content in the reaction system is at most 1000 ppm, from the viewpoint of maintenance of catalytic activity.

As mentioned above, according to the process for preparing 4-hydroxybutyl acrylate of the present invention, the collected dialkyltin oxide having an alkyl group of 4 to 18 carbon atoms can be repeatedly used until its catalytic activity is lost. Therefore, the process for preparing 4-hydroxybutyl acrylate of the present invention is excellent in industrial productivity.

The 4-hydroxybutyl acrylate prepared in the above by the process of the present invention is useful, for example, as raw materials such as coatings for automobiles, coatings for building materials, coating agents for electronic materials and photosensitive resin compositions.

[Second Invention]

The process for preparing 4-hydroxybutyl(meth)acrylate is a process for preparing 4-hydroxybutyl(meth)acrylate by carrying out the transesterification reaction of 1,4-butanediol and an alkyl(meth)acrylate, characterized in that the transesterification reaction of 1,4-butanediol and an alkyl(meth)acrylate is carried out in the presence of a catalyst for transesterification represented by the formula (II):

[Chem. 6]

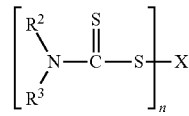
(II)

wherein each of $R^2$ and $R^3$ is independently an alkyl group having 1 to 18 carbon atoms, an aryl group having 6 to 12 carbon atoms or an aralkyl group having 7 to 12 carbon atoms, X is an alkali metal atom or an alkaline earth metal, n is a number which shows the atomic value of X.

In the present invention, first of all, the transesterification reaction of 1,4-butanediol and an alkyl(meth)acrylate is carried out.

The alkyl(meth)acrylate includes, for example, methyl(meth)acrylate, ethyl(meth)acrylate, propyl(meth)acrylate, n-butyl(meth)acrylate, isobutyl(meth)acrylate, tert-butyl(meth)acrylate, and the like. These alkyl(meth)acrylates can be used alone respectively, or at least two kinds thereof can be used in combination. Among the alkyl(meth)acrylates, from the viewpoint of efficient separation of the resulting 4-hydroxybutyl(meth)acrylate from the alkyl(meth)acrylate, an alkyl(meth)acrylate represented by the formula (III):

[Chem. 7]

 (III)

wherein $R^4$ is a hydrogen atom or methyl group, and $R^5$ is an alkyl group having 1 to 4 carbon atoms is preferable, an alkyl(meth)acrylate represented by the formula (III) in which $R^4$ is a hydrogen atom or methyl group, and $R^5$ is an alkyl group having 1 to 3 carbon atoms is more preferable, and methyl(meth)acrylate is furthermore preferable.

The amount of the alkyl(meth)acrylate per one mole of 1,4-butanediol is preferably at least 0.5 moles from the viewpoint of increase in reaction rate, and preferably at most 5 moles, more preferably at most 3 moles from the viewpoint of decrease in the amount of the unreacted alkyl(meth)acrylate.

When the transesterification reaction of 1,4-butanediol and an alkyl(meth)acrylate is carried out, a catalyst for transesterification represented by the formula (II) is used.

There is one of great characteristics of the present invention in that the catalyst for transesterification represented by the formula (II) is used.

When the catalyst for transesterification represented by the formula (II) is used, there are excellent effects such that 4-hydroxybutyl (meth)acrylate can be efficiently prepared, that the catalyst for transesterification which is used in the transesterification reaction can be efficiently collected, and that the catalyst for transesterification can be reused.

In the catalyst for transesterification represented by the formula (II), each of $R^2$ and $R^3$ is independently an alkyl group having 1 to 18 carbon atoms, an aryl group having 6 to 12 carbon atoms or an aralkyl group having 7 to 12 carbon atoms, from the viewpoint of maintenance of catalytic activity and the viewpoint of increase in yield of 4-hydroxybutyl (meth)acrylate obtained by the transesterification reaction. Incidentally, it is preferred that $R^2$ is the same as $R^3$ from the viewpoint of easiness in the preparation of the catalyst for transesterification represented by the formula (II).

Among the alkyl group having 1 to 18 carbon atoms, from the viewpoint of the maintenance of catalytic activity and the viewpoint of increase in yield of 4-hydroxybutyl(meth)acrylate, an alkyl group having 1 to 12 carbon atoms is preferable, and an alkyl group having 1 to 8 carbon atoms is more preferable, and from the viewpoint of easiness of the removal of the catalyst for transesterification by washing with water after the preparation of 4-hydroxybutyl(meth)acrylate, an alkyl group having 1 to 4 carbon atoms is furthermore preferable. The alkyl group having 1 to 4 carbon atoms includes methyl group, ethyl group, n-propyl group, isopropyl group, n-butyl group, isobutyl group and tert-butyl group.

The aryl group having 6 to 12 carbon atoms include, for example, phenyl group, tolyl group, xylyl group, biphenyl group, naphthyl group, anthryl group, phenanthryl group and the like, and the present invention is not limited only to those exemplified ones.

The aralkyl group having 7 to 12 carbon atoms include, for example, benzyl group, phenylethyl group, methylbenzyl group, naphthyl methyl group and the like, and the present invention is not limited only to those exemplified ones.

In the formula (II), X is an alkali metal atom or an alkaline earth metal. The alkali metal atom includes for example, lithium, sodium, potassium and the like. The alkaline earth metal includes, for example, magnesium, calcium, barium and the like. Among the X, from the viewpoint of the maintenance of catalytic activity and the viewpoint of increase in yield of 4-hydroxybutyl(meth)acrylate, sodium, potassium, magnesium and calcium are preferable, sodium, potassium and magnesium are more preferable, and sodium and potassium are furthermore preferable.

In the formula (II), n is a number which shows the atomic value of X. Therefore, when the X is an alkali metal, n is 1, and when the X is an alkaline earth metal, n is 2.

Concrete examples of the catalyst for transesterification represented by the formula (II) include alkali metal salts of dithiocarbamic acid, such as sodium dimethyldithiocarbamate, sodium diethyldithiocarbamate, sodium dipropyldithiocarbamate, sodium dibutyldithiocarbamate, potassium dimethyldithiocarbamate, potassium diethyldithiocarbamate, potassium dipropyldithiocarbamate, potassium dibutyldithiocarbamate, sodium methylethyldithiocarbamate, sodium methylpropyldithiocarbamate, sodium ethylpropyldithiocarbamate, sodium methylbutyldithiocarbamate, potassium methylethyldithiocarbamate, potassium methylpropyldithiocarbamate, potassium ethylpropyldithiocarbamate, potassium methylbutyldithiocarbamate, sodium diphenyldithiocarbamate, sodium ditolyldithiocarbamate, sodium dixylyldithiocarbamate, sodium dibiphenyldithiocarbamate, sodium dinaphthyldithiocarbamate, sodium dianthryldithiocarbamate, sodium diphenanthryldithiocarbamate, potassium diphenyldithiocarbamate, potassium ditolyldithiocarbamate, potassium dixylyldithiocarbamate, potassium dibiphenyldithiocarbamate, potassium dinaphthyldithiocarbamate, potassium dianthryldithiocarbamate, potassium diphenanthryldithiocarbamate, sodium dibenzyldithiocarbamate, sodium diphenylethyldithiocarbamate, sodium dimethylbenzyldithiocarbamate, sodium dinaphthylmethyldithiocarbamate, potassium dibenzyldithiocarbamate, potassium diphenylethyldithiocarbamate, potassium dimethylbenzyldithiocarbamate and potassium dinaphthylmethyldithiocarbamate; and alkaline earth metal salts of dithiocarbamic acid, such as magnesium dimethyldithiocarbamate, magnesium diethyldithiocarbamate, magnesium dipropyldithiocarbamate, magnesium dibutyldithiocarbamate, calcium dimethyldithiocarbamate, calcium diethyldithiocarbamate, calcium dipropyldithiocarbamate, calcium dibutyldithiocarbamate, magnesium methylethyldithiocarbamate, magnesium methylpropyldithiocarbamate, magnesium ethylpropyldithiocarbamate, magnesium methylbutyldithiocarbamate, calcium methylethyldithiocarbamate, calcium methylpropyldithiocarbamate, calcium ethylpropyldithiocarbamate, calcium methylbutyldithiocarbamate, magnesium diphenyldithiocarbamate, magnesium ditolyldithiocarbamate, magnesium dixylyldithiocarbamate, magnesium dibiphenyldithiocarbamate, magnesium dinaphthyldithiocarbamate, magnesium dianthryldithiocarbamate, magnesium diphenanthryldithiocarbamate, calcium diphenyldithiocarbamate, calcium ditolyldithiocarbamate, calcium dixylyldithiocarbamate, calcium dibiphenyldithiocarbamate, calcium dinaphthyldithiocarbamate, calcium dianthryldithiocarbamate, calcium diphenanthryldithiocarbamate, magnesium dibenzyldithiocarbamate, magnesium diphenylethyldithiocarbamate, magnesium dimethylbenzyldithiocarbamate, magnesium dinaphthylmethyldithiocarbamate, calcium dibenzyldithiocarbamate, calcium diphenylethyldithiocarbamate, calcium dimethylbenzyldithiocarbamate and calcium dinaphthylmethyldithiocarbamate, and the present invention is not limited only to those exemplified ones.

Among the catalysts for transesterification represented by the formula (II), from the viewpoint that the catalyst can be reused by washing the catalyst with water to separate and collect the catalyst after the transesterification reaction, salts of a dialkyldithiocarbamic acid having an alkyl group of 1 to 4 carbon atoms is preferable, alkali metal salts of a dialkyldithiocarbamic acid having an alkyl group of 1 to 4 carbon atoms is more preferable, and sodium dimethyldithiocarbamate, sodium diethyldithiocarbamate, sodium dipropyldithiocarbamate, sodium dibutyldithiocarbamate, potassium dimethyldithiocarbamate, potassium diethyldithiocarbamate, potassium dipropyldithiocarbamate and potassium dibutyldithiocarbamate are furthermore preferable.

The catalysts for transesterification represented by the formula (II) can be used only in one kind, or at least two kinds thereof can be used in combination.

In the present invention, the catalyst for transesterification represented by the formula (II) is used, and can be used together with other catalyst for transesterification within a scope in which an object of the present invention is not hindered. The other catalyst for transesterification includes, for example, ones described in column [0043] of Japanese Unexamined Patent Publication No. 2002-326973 and the like, and the present invention is not limited only to those exemplified ones.

The amount of the catalyst for transesterification represented by the formula (II) cannot be absolutely determined because the amount differs depending on the kind of the (meth)acrylate which is used as a raw material in the transesterification. The amount of the catalyst for transesterification represented by the formula (II) is usually preferably 0.00001 to 0.01 moles, more preferably 0.0001 to 0.005 moles per one mole of the (meth)acrylate which is used as a raw material, from the viewpoint of acceleration of the transesterification reaction of 1,4-butanediol and the (meth)acrylate.

When 1,4-butanediol is reacted with the alkyl(meth)acrylate, it is preferred that 1,4-butanediol is reacted with the alkyl(meth)acrylate in the presence of a polymerization inhibitor from the viewpoint of inhibition of polymerization of the alkyl(meth)acrylate.

As the polymerization inhibitor, there can be exemplified ones which can be used in the first present invention. The polymerization inhibitors can be used only in one kind, or at least two kinds thereof can be used in combination.

The amount of the polymerization inhibitor per 100 parts by mass of the alkyl(meth)acrylate is preferably at least 0.001 parts by mass, more preferably at least 0.005 parts by mass, and furthermore preferably at least 0.01 parts by mass, from the viewpoint of inhibition of polymerization of the alkyl(meth)acrylate, and is preferably at most 5 parts by mass, more preferably at most 3 parts by mass, and furthermore preferably at most 1 part by mass, from the viewpoint of enhancement of purity of 4-hydroxybutyl (meth)acrylate.

Incidentally, when the transesterification reaction of 1,4-butanediol and an alkyl(meth)acrylate is carried out, an organic solvent can be used.

As the organic solvent, there can be exemplified ones which are described in the first present invention. The organic solvents can be used only in one kind, or at least two kinds thereof can be used in combination.

The amount of the organic solvent is not particularly limited, and can be usually 5 to 200 parts by mass based on 100 parts by mass of the total amount of 1,4-butanediol and the alkyl(meth)acrylate.

When the transesterification reaction of 1,4-butanediol and the alkyl(meth)acrylate is carried out, the reaction temperature is preferably at lowest 30° C., and more preferably at lowest 50° C., from the viewpoint of increase in reaction rate, and preferably at highest 150° C. from the viewpoint of inhibition of polymerization of the resulting 4-hydroxybutyl (meth)acrylate.

When the transesterification reaction of 1,4-butanediol and the alkyl(meth)acrylate is carried out, the atmosphere is preferably an atmosphere containing oxygen from the viewpoint of inhibition of polymerization of the alkyl(meth)acrylate, and more preferably a gas containing oxygen in a content of from 5% by volume to atmospheric concentration of oxygen from the viewpoint of enhancement of safety. Also, the pressure of the atmosphere is usually atmospheric pressure, and can be increased or reduced. For example, when the pressure of the atmosphere is reduced, there is a merit such that a side reaction can be suppressed, because the reaction temperature can be lowered.

When the transesterification reaction of 1,4-butanediol and the alkyl(meth)acrylate is carried out, the reaction time cannot be absolutely determined because the reaction time differs depending on the amounts of 1,4-butanediol and the alkyl(meth)acrylate, reaction temperature and the like. Therefore, the reaction time is usually controlled so that the transesterification reaction is completed. The end point of the transesterification reaction can be confirmed by, for example, gas chromatography, liquid chromatography and the like.

The transesterification reaction of 1,4-butanediol and the alkyl (meth)acrylate can be carried out by using a rectifying tower, a fluidized bed, a fixed bed, a reaction distillation column or the like, and the present invention is not limited only to those exemplified ones. In addition, the transesterification reaction of 1,4-butanediol and the alkyl(meth)acrylate can be carried out by any of a continuous method and a batch method.

In the progress of the transesterification reaction of 1,4-butanediol and the alkyl(meth)acrylate, an alcohol is generated as a by-product. It is usually preferred that the alcohol generated as a by-product is removed from the reaction system in order to accelerate the reaction. The alcohol which is generated as a by-product can be removed from the reaction system as, for example, an azeotropic mixture with a (meth)acrylate or a suitable solvent.

After the transesterification reaction of 1,4-butanediol and the alkyl(meth)acrylate is carried out in the presence of the catalyst for transesterification represented by the formula (II), the catalyst for esterification represented by the formula (II) which is used as the above-mentioned catalyst for transesterification can be collected from the resulting reaction mixture by means of, for example, distillation.

Also, an objective 4-hydroxybutyl acrylate can be collected from the resulting reaction mixture by distillation of an organic solvent, an unreacted (meth)acrylate and an alcohol from the reaction mixture. The removal of the unreacted (meth)acrylate and the alcohol can be carried out by means of, for example, distillation, extraction and the like.

More specifically, the resulting 4-hydroxybutyl(meth) acrylate can be collected from the resulting reaction mixture, for example, by mixing the reaction mixture obtained by the transesterification reaction of 1,4-butanediol and the alkyl (meth)acrylate with an extractant containing water and an aliphatic hydrocarbon compound to extract 4-hydroxybutyl (meth)acrylate to a water layer, and thereafter, mixing the water layer with an extractant containing an aromatic hydrocarbon compound to extract 4-hydroxybutyl(meth)acrylate contained in the water layer to the aromatic hydrocarbon compound.

When the reaction mixture is mixed with an extractant containing water and the aliphatic hydrocarbon compound, 4-hydroxybutyl (meth)acrylate contained in the reaction mixture can be extracted to the water layer, and the resulting 1,4-butanediol di(meth)acrylate obtained as a by-product and the like can be extracted to the aliphatic hydrocarbon compound layer. Therefore, the water layer containing 4-hydroxybutyl (meth)acrylate can be collected by separating the water layer from the aliphatic hydrocarbon compound layer.

The aliphatic hydrocarbon compound includes, for example, aliphatic hydrocarbon compounds having 6 to 12 carbon atoms, such as cyclohexane, n-hexane, n-heptane, n-octane, n-decane, isohexane, isooctane and isodecane, and the present invention is not limited only to those exemplified ones. Incidentally, in this description, the aliphatic hydrocarbon compound includes the concept that the aliphatic hydrocarbon compound contains a hydrocarbon compound having an alicyclic structure, such as cyclohexane. The extractant containing water and the aliphatic hydrocarbon compound may contain an aromatic hydrocarbon compound within the scope in which an object of the present invention is not hindered.

In the above-mentioned extractant, each amount of the aliphatic hydrocarbon compound and water cannot be absolutely determined because the amount differs depending on the amount of the reaction mixture and the like. It is preferred that the amount is appropriately controlled to an amount which is suitable for extracting 4-hydroxybutyl (meth)acrylate contained in the reaction mixture to the water layer, and separating the aliphatic hydrocarbon compound layer from the water layer. In addition, the temperature during the above-mentioned extracting operation is not particularly limited, and is usually 5 to 50° C. or so.

Next, the water layer to which 4-hydroxybutyl(meth) acrylate is extracted is mixed with an extractant containing an aromatic hydrocarbon compound to extract 4-hydroxybutyl acrylate contained in the water layer to an aromatic hydrocarbon compound layer, and the aromatic hydrocarbon compound layer is separated from the water layer to collect the aromatic hydrocarbon compound layer containing 4-hydroxybutyl(meth)acrylate.

The aromatic hydrocarbon compound includes, for example, benzene, ethyl benzene, toluene, xylene and the like, and the present invention is not limited only to those exemplified ones. Incidentally, the extractant containing the aromatic hydrocarbon compound may contain an aliphatic hydrocarbon compound, water and the like within a scope which does not hinder an object of the present invention.

The amount of the aromatic hydrocarbon compound cannot be absolutely determined, because the amount differs depending on the amount of the water layer which is separated from the above-mentioned aliphatic hydrocarbon compound layer. It is preferred that the amount is appropriately controlled to an amount which is suitable for extracting 4-hydroxybutyl(meth)acrylate contained in the water layer to the aromatic hydrocarbon layer, and separating the aromatic hydrocarbon compound layer from the water layer. The temperature during the above-mentioned extracting operation is not particularly limited, and is usually preferably 5 to 50° C. or so.

The 4-hydroxybutyl(meth)acrylate contained in the above-mentioned aromatic hydrocarbon compound layer can be collected by, for example, evaporation of the aromatic hydrocarbon compound and the like. The temperature during the removal of the aromatic hydrocarbon compound from the aromatic hydrocarbon compound layer is not particularly limited, and is usually preferably 20 to 150° C. or so. The 4-hydroxybutyl acrylate collected in the above can be purified by distillation, washing and the like as occasion demands.

On the other hand, the aliphatic hydrocarbon compound layer contains 1,4-butanediol di(meth)acrylate which is generated as a by-product. The aliphatic hydrocarbon compound layer also contains the catalyst for transesterification represented by the formula (II) other than the 1,4-butanediol di(meth)acrylate. Therefore, from the viewpoint of effective use of the catalyst for transesterification represented by the formula (II), the catalyst for transesterification represented by the formula (II) can be collected from the aliphatic hydrocarbon compound layer by distillation, condensation, washing and the like.

In the present invention, the catalytic activity of the collected catalyst for transesterification represented by the formula (II) is not so lowered, and is maintained. Therefore, the catalyst for transesterification represented by the formula (II) can be reused as a catalyst for the transesterification reaction of 1,4-butanediol and an alkyl(meth)acrylate.

Accordingly, the catalyst for transesterification represented by the formula (II) can be reused as a catalyst for the transesterification reaction of 1,4-butanediol and an alkyl acrylate, and the transesterification reaction of 1,4-butanediol and an alkyl(meth)acrylate can be carried out in the presence of the collected catalyst for transesterification represented by the formula (II). At that time, it is preferred that the collected catalyst for transesterification represented by the formula (II) is reused after the reaction system of the transesterification reaction of 1,4-butanediol and an alkyl (meth)acrylate is dried so that the water content in the reaction system of the transesterification reaction of 1,4-butanediol and the alkyl (meth)acrylate is at most 1000 ppm, from the viewpoint of the maintenance of catalytic activity.

As mentioned above, according to the process for preparing 4-hydroxybutyl(meth)acrylate of the present invention, the collected catalyst for transesterification represented by the formula (II) can be repeatedly used until its catalytic activity is lost. Therefore, the process for preparing 4-hydroxybutyl(meth)acrylate of the present invention is excellent in industrial productivity.

The 4-hydroxybutyl(meth)acrylate obtained in the above by the process of the present invention is useful, for example, as raw materials such as coatings for automobiles, coatings for building materials, coating agents for electronic materials and photosensitive resin compositions.

[Third Invention]

Hereinafter, the third invention is described.

The process for preparing 4-hydroxybutyl acrylate of the third present invention is a process for preparing 4-hydroxybutyl acrylate by carrying out the transesterification reaction of 1,4-butanediol and an alkyl acrylate to prepare 4-hydroxybutyl acrylate, characterized by carrying out the transesterification reaction of 1,4-butanediol and an alkyl acrylate in the presence of a catalyst for transesterification, thereafter extracting the resulting 4-hydroxybutyl acrylate from the resulting reaction mixture containing 4-hydroxybutyl acrylate, to collect 4-hydroxybutyl acrylate.

In the present invention, first of all, the transesterification reaction of 1,4-butanediol and an alkyl acrylate is carried out.

The alkyl acrylate includes, for example, methyl acrylate, ethyl acrylate, propyl acrylate, n-butyl acrylate, isobutyl acrylate, tert-butyl acrylate, and the like. These alkyl acrylates can be used alone, respectively, or at least two kinds thereof can be used in combination. Among the alkyl acrylates, from the viewpoint of efficient separation of the resulting 4-hydroxybutyl acrylate from the alkyl acrylate which is used as a raw material, an alkyl acrylate having an alkyl group of 1 to 4 carbon atoms is preferable, an alkyl acrylate having an alkyl group of 1 to 3 carbon atoms is more preferable, and methyl acrylate is furthermore preferable.

The amount of the alkyl acrylate per one mole of 1,4-butanediol is preferably at least 0.5 moles from the viewpoint of increase in reaction rate, and preferably at most 5 moles, more preferably at most 3 moles from the viewpoint of decrease in the amount of the unreacted alkyl acrylate.

In the present invention, when the transesterification reaction of 1,4-butanediol and an alkyl acrylate is carried out, a catalyst for transesterification is used.

The catalyst for transesterification includes, for example, a tin compound, a metal salt of dithiocarbamic acid, a titanium compound, a thallium compound, a lead compound, a chromium compound, a metal alcoholate, lithium hydroxide and the like, and the present invention is not limited only to those exemplifies ones. These catalysts for transesterification can be used alone respectively, or at least two kinds thereof can be used in combination.

Among the catalysts for transesterification, the lead compound and the metal salt of dithiocarbamic acid are preferable, and the lead compound is more preferable. When the lead compound or the metal salt of dithiocarbamic acid is used as a catalyst for transesterification, there are exhibited excellent effects such that the transesterification reaction of 1,4-butanediol and methyl acrylate can efficiently progress, that an organic acid such as acrylic acid or acetic acid is not necessitated, and that 4-hydroxybutyl acrylate having a low content of an acid component can be efficiently prepared.

The lead compound includes, for example, dialkyltin oxide, tin carboxylates such as tin octylate, dialkyltin dialkyl esters such as dibutyltin dilaurate, monoalkyltin oxides such as monobutyltin oxide, cuprous chloride, and the like, and the present invention is not limited only to those exemplified ones. These lead compounds can be used alone respectively, or at least two kinds thereof can be used in combination.

Among the lead compounds, the dialkyltin oxide is preferable. When the dialkyltin oxide is used as a catalyst for transesterification, there are some merits such that the transesterification reaction of 1,4-butanediol and the alkyl acrylate can efficiently progress, and that 4-hydroxybutyl acrylate having a low content of an acid component can be efficiently prepared without the necessity of use of an organic acid such as acrylic acid or acetic acid, at the time of preparation of 4-hydroxybutyl acrylate by carrying out the transesterification reaction of 1,4-butanediol and methyl acrylate.

The dialkyltin oxides include, for example, dialkyltin oxides having an alkyl group of 4 to 18 carbon atoms, such as dibutyltin oxide, dioctyltin oxide and dilauryltin oxide, and the present invention is not limited only to those exemplified ones. These dialkyltin oxides can be used alone respectively, or at least two kinds thereof can be used in combination. Among these dialkyltin oxides, a dialkyltin oxide having an alkyl group of 4 to 12 carbon atoms is preferable, a dialkyltin oxide having an alkyl group of 4 to 8 carbon atoms is more preferable, and dibutyltin oxide and dioctyltin oxide are further preferable, and dioctyltin oxide is furthermore preferable, from the viewpoint that the transesterification reaction of 1,4-butanediol and an alkyl acrylate is accelerated.

The metal salts of dithiocarbamic acid include, for example, alkali metal salts of dithiocarbamic acid, such as sodium dimethyldithiocarbamate, sodium diethyldithiocarbamate, sodium dipropyldithiocarbamate, sodium dibutyldithiocarbamate, potassium dimethyldithiocarbamate, potassium diethyldithiocarbamate, potassium dipropyldithiocarbamate, potassium dibutyldithiocarbamate, sodium methylethyldithiocarbamate, sodium methylpropyldithiocarbamate, sodium ethylpropyldithiocarbamate, sodium methylbutyldithiocarbamate, potassium methylethyldithiocarbamate, potassium methylpropyldithiocarbamate, potassium ethylpropyldithiocarbamate, potassium methylbutyldithiocarbamate, sodium diphenyldithiocarbamate, sodium ditolyldithiocarbamate, sodium dixylyldithiocarbamate, sodium dibiphenyldithiocarbamate, sodium dinaphthyldithiocarbamate, sodium dianthryldithiocarbamate, sodium diphenanthryldithiocarbamate, potassium diphenyldithiocarbamate, potassium ditolyldithiocarbamate, potassium dixylyldithiocarbamate, potassium dibiphenyldithiocarbamate, potassium dinaphthyldithiocarbamate, potassium dianthryldithiocarbamate, potassium diphenanthryldithiocarbamate, sodium dibenzyldithiocarbamate, sodium diphenylethyldithiocarbamate, sodium dimethylbenzyldithiocarbamate, sodium dinaphthylmethyldithiocarbamate, potassium dibenzyldithiocarbamate, potassium diphenylethyldithiocarbamate, potassium dimethylbenzyldithiocarbamate and potassium dinaphthylmethyldithiocarbamate; and alkaline earth metal salts of dithiocarbamic acid, such as magnesium dimethyldithiocarbamate, magnesium diethyldithiocarbamate, magnesium dipropyldithiocarbamate, magnesium dibutyldithiocarbamate, calcium dimethyldithiocarbamate, calcium diethyldithiocarbamate, calcium dipropyldithiocarbamate, calcium dibutyldithiocarbamate, magnesium methylethyldithiocarbamate, magnesium methylpropyldithiocarbamate, magnesium ethylpropyldithiocarbamate, magnesium methylbutyldithiocarbamate, calcium methylethyldithiocarbamate, calcium methylpropyldithiocarbamate, calcium ethylpropyldithiocarbamate, calcium methylbutyldithiocarbamate, magnesium diphenyldithiocarbamate, magnesium ditolyldithiocarbamate, magnesium dixylyldithiocarbamate, magnesium dibiphenyldithiocarbamate, magnesium dinaphthyldithiocarbamate, magnesium dianthryldithiocarbamate, magnesium diphenanthryldithiocarbamate, calcium diphenyldithiocarbamate, calcium ditolyldithiocarbamate, calcium dixylyldithiocarbamate, calcium dibiphenyldithiocarbamate, calcium dinaphthyldithiocarbamate, calcium dianthryldithiocarbamate, calcium diphenanthryldithiocarbamate, magnesium dibenzyldithiocarbamate, magnesium diphenylethyldithiocarbamate, magnesium dimethylbenzyldithiocarbamate, magnesium dinaphthylmethyldithiocarbamate, calcium dibenzyldithiocarbamate, calcium diphenylethyldithiocarbamate, calcium dimethylbenzyldithiocarbamate and calcium dinaphthylmethyldithiocarbamate, and the present invention is not limited only to those exemplified ones. These metal salts of dithiocarbamic acid can be used alone respectively, or at least two kinds thereof can be used in combination.

Among the metal salts of dithiocarbamic acid, from the viewpoint that the metal salts of dithiocarbamic acid can be reused by washing the metal salts with water to separate and collecting the metal salts after the transesterification reaction, salts of a dialkyldithiocarbamic acid having an alkyl group of 1 to 4 carbon atoms is preferable, alkali metal salts of a dialkyldithiocarbamic acid having an alkyl group of 1 to 4 carbon atoms is more preferable, and sodium dimethyldithiocarbamate, sodium diethyldithiocarbamate, sodium dipropyldithiocarbamate, sodium dibutyldithiocarbamate, potassium dimethyldithiocarbamate, potassium diethyldithiocarbamate, potassium dipropyldithiocarbamate and potassium dibutyldithiocarbamate are furthermore preferable.

The titanium compound contains, for example, tetraethyl titanate, tetraisopropyl titanate, tetrabutyl titanate, tetramethoxy titanate, tetraethoxy titanate, tetrabutoxy titanate and the like, and the present invention is not limited only to those exemplified ones. These titanium compounds can be used alone respectively, at least two kinds thereof can be used in combination.

The metal alcoholate includes, for example, alkali metal alcoholates such as sodium methylate, sodium ethylate, lithium methylate and lithium ethylate; alkaline metal alcoholates such as calcium methylate, calcium ethylate, magnesium methylate and magnesium ethylate; aluminum alcoholates such as aluminum methylate and aluminum ethylate; and the like, and the present invention is not limited only to those exemplified ones. These metal alcoholates can be used alone respectively, or at least two kinds thereof can be used in combination.

The amount of the catalyst for transesterification is preferably at least 0.00001 moles, more preferably at least 0.0001 moles, and preferably at most 0.01 moles, more preferably at most 0.005 moles per one mole of the alkyl acrylate from the viewpoint of efficient acceleration of the transesterification reaction of 1,4-butanediol and the alkyl acrylate.

When 1,4-butanediol is reacted with the alkyl acrylate, it is preferred that 1,4-butanediol is reacted with the alkyl acrylate in the presence of a polymerization inhibitor from the viewpoint of inhibition of polymerization of the alkyl acrylate.

As the polymerization inhibitor, there can be exemplified ones which can be used in the first invention. The polymerization inhibitors can be used only in one kind, or at least two kinds thereof can be used in combination.

The amount of the polymerization inhibitor per 100 parts by mass of the alkyl acrylate is preferably at least 0.001 parts by mass, more preferably at least 0.005 parts by mass, and furthermore preferably at least 0.01 parts by mass from the viewpoint of inhibition of polymerization of the alkyl acrylate, and is preferably at most 5 parts by mass, more preferably at most 3 parts by mass, and furthermore preferably at most 1 part by mass from the viewpoint of enhancement of the purity of 4-hydroxybutyl acrylate.

Incidentally, when the transesterification reaction of 1,4-butanediol and the alkyl acrylate is carried out, an organic solvent can be used.

As the organic solvent, there can be exemplified ones which are used in the first invention. The organic solvents can be used only in one kind, or at least two kinds thereof can be used in combination.

The amount of the organic solvent is not particularly limited, and can be usually 5 to 200 parts by mass or so based on 100 parts by mass of the total amount of 1,4-butanediol and the alkyl acrylate.

When the transesterification reaction of 1,4-butanediol and the alkyl acrylate is carried out, the reaction temperature is preferably at lowest 30° C., and more preferably at lowest 50° C., from the viewpoint of increase in reaction rate, and preferably at highest 150° C. from the viewpoint of inhibition of polymerization of the resulting 4-hydroxybutyl acrylate.

When the transesterification reaction of 1,4-butanediol and the alkyl acrylate is carried out, the atmosphere is preferably an atmosphere containing oxygen from the viewpoint of inhibition of polymerization of the alkyl acrylate, and more preferably a gas containing oxygen in a content of from 5% by volume to atmospheric concentration of oxygen from the viewpoint of enhancement of safety. Also, the pressure of the atmosphere is usually atmospheric pressure, and can be increased or reduced. For example, when the pressure of the atmosphere is reduced, there is a merit such that a side reaction can be suppressed, because the reaction temperature can be lowered.

When the transesterification reaction of 1,4-butanediol and the alkyl acrylate is carried out, the reaction time cannot be absolutely determined because the reaction time differs depending on the amounts of 1,4-butanediol and the alkyl acrylate, reaction temperature and the like. Therefore, the reaction time is usually controlled so that the transesterification reaction of 1,4-butanediol and the alkyl acrylate is completed. The end point of the transesterification reaction of 1,4-butanediol and the alkyl acrylate can be confirmed by, for example, gas chromatography, liquid chromatography and the like.

The transesterification reaction of 1,4-butanediol and the alkyl acrylate can be carried out by using a rectifying tower, a fluidized bed, a fixed bed, a reaction distillation column or the like, and the present invention is not limited only to those exemplified ones. In addition, the transesterification reaction of 1,4-butanediol and the alkyl acrylate can be carried out by any of a continuous method and a batch method.

In the progress of the transesterification reaction of 1,4-butanediol and the alkyl acrylate, an alcohol is generated as a by-product. It is usually preferred that the alcohol generated as a by-product is removed from the reaction system in order to accelerate the reaction. The alcohol generated as a by-product can be removed from the reaction system as, for example, an azeotropic mixture with an acrylate or a suitable solvent.

After the transesterification reaction of 1,4-butanediol and the alkyl acrylate is carried out, an organic solvent which is used in the reaction, an unreacted acrylate and an alcohol are distilled away from the resulting reaction mixture, to collect an objective hydroxybutyl alcohol. The removal of the unreacted acrylate and the alcohol can be carried out by extracting.

More specifically, the resulting 4-hydroxybutyl acrylate can be collected from the resulting reaction mixture, for example, by mixing the reaction mixture obtained by the transesterification reaction of 1,4-butanediol and the alkyl acrylate with an extractant containing water and an aliphatic hydrocarbon compound to extract 4-hydroxybutyl acrylate to a water layer, and thereafter, mixing the water layer with an extractant containing an aromatic hydrocarbon compound to extract 4-hydroxybutyl acrylate contained in the water layer to the aromatic hydrocarbon compound.

When the reaction mixture is mixed with an extractant containing water and the aliphatic hydrocarbon compound, 4-hydroxybutyl (meth)acrylate contained in the reaction mixture can be extracted to the water layer, and the resulting 1,4-butanediol diacrylate generated as a by-product and the like can be extracted to the aliphatic hydrocarbon compound layer. Therefore, the water layer containing 4-hydroxybutyl acrylate can be collected by separating the water layer from the aliphatic hydrocarbon compound layer.

The aliphatic hydrocarbon compounds include, for example, aliphatic hydrocarbon compounds having 6 to 12 carbon atoms, such as cyclohexane, n-hexane, n-heptane, n-octane, n-decane, isohexane, isooctane and isodecane, and the present invention is not limited only to those exemplified ones. Incidentally, in this description, the aliphatic hydrocarbon compound includes the concept that the aliphatic hydrocarbon compound contains a hydrocarbon compound having an alicyclic structure, such as cyclohexane. The extractant containing water and the aliphatic hydrocarbon compound may contain an aromatic hydrocarbon compound within the scope in which an object of the present invention is not hindered.

In the above-mentioned extractant, each amount of the aliphatic hydrocarbon compound and water cannot be absolutely determined because the amount differs depending on the amount of the reaction mixture and the like. It is preferred that the amount is appropriately controlled to an amount which is suitable for extracting 4-hydroxybutyl acrylate contained in the reaction mixture to the water layer, and separating the aliphatic hydrocarbon compound layer from the water layer. In addition, the temperature during the above-mentioned extracting operation is not particularly limited, and is usually preferably 5 to 50° C. or so.

Incidentally, after the reaction mixture is mixed with the extractant containing water and an aliphatic hydrocarbon compound, and 4-hydroxybutyl acrylate is extracted to the water layer, it is preferred that the water layer is contacted with an ion exchange resin. When the above-mentioned water layer is contacted with the ion exchange resin, there can be obtained 4-hydroxybutyl acrylate having a lower content of acidic components.

The ion exchange resin includes, for example, anion exchange resin having a basic group based on a quaternary ammonium salt, acidic cation exchange resin based on an acid such as phosphoric acid, a carboxylic acid or sulfonic acid, and the like, and the present invention is not limited only to those exemplified ones. The anion exchange resin includes, a strong basic anion resin, a weak basic anion resin, a mixture of a strong basic anion resin and a strong basic anion resin, and the like, and the present invention is not limited only to those exemplified ones. The acidic ion exchange resin includes, for example, a strong acidic cation resin, a weak acidic cation resin, a mixture of a strong acidic cation resin and a strong basic anion resin, and the like, and the present invention is not limited only to those exemplified ones. Among these ion exchange resins, the anion exchange resin is preferable from the viewpoint of preparation of 4-hydroxybutyl acrylate having a lower content of acidic components.

The amount of the ion exchange resin cannot be absolutely determined depending on its kinds and the like, and is usually 0.0001 to 0.1 times of the volume of the water layer which is contacted with the ion exchange resin.

Next, the water layer to which 4-hydrxybutyl acrylate is extracted is mixed with an extractant containing an aromatic hydrocarbon compound to extract 4-hydroxybutyl acrylate contained in the water layer to an aromatic hydrocarbon compound layer, and the aromatic hydrocarbon compound layer is separated from the water layer to collect the aromatic hydrocarbon compound layer containing 4-hydroxybutyl acrylate.

The aromatic hydrocarbon compound includes, for example, benzene, ethylbenzene, toluene, xylene and the like, and the present invention is not limited only to those exemplified ones. Incidentally, the extractant containing the aromatic hydrocarbon compound may contain an aliphatic hydrocarbon compound, water and the like within a scope which does not hinder an object of the present invention.

The amount of the aromatic hydrocarbon compound cannot be absolutely determined, because the amount differs depending on the amount of the water layer which is separated from the above-mentioned aliphatic hydrocarbon compound layer. It is preferred that the amount is appropriately controlled to an amount which is suitable for extracting 4-hydroxybutyl acrylate contained in the water layer to the aromatic hydrocarbon layer, and separating the aromatic hydrocarbon compound layer from the water layer. The temperature during the above-mentioned extracting operation is not particularly limited, and is usually preferably 5 to 50° C. or so.

The 4-hydroxybutyl(meth)acrylate contained in the above-mentioned aromatic hydrocarbon compound layer can be collected by, for example, evaporation of the aromatic hydrocarbon compound, and the like. The temperature during the removal of the aromatic hydrocarbon compound from the aromatic hydrocarbon compound layer is not particularly limited, and is usually preferably 20 to 150° C. or so. The 4-hydroxybutyl acrylate collected in the above can be purified by distillation, washing and the like as occasion demands.

On the other hand, the aliphatic hydrocarbon compound layer contains 1,4-butanediol diacrylate generated as a by-product. The aliphatic hydrocarbon compound layer also contains the dialkyltin oxide other than the 1,4-butanediol diacrylate. Therefore, from the viewpoint of effective use of the dialkyltin oxide, the dialkyltin oxide can be collected from the aliphatic hydrocarbon compound layer by distillation, condensation, washing and the like.

In the present invention, the catalytic activity of the collected dialkyltin oxide is not so lowered, and is maintained. Therefore, the dialkyltin oxide can be reused as a catalyst for the transesterification reaction of 1,4-butanediol and an alkyl acrylate. Accordingly, the collected dialkyltin oxide can be reused as a catalyst for the transesterification reaction of 1,4-butanediol and an alkyl acrylate, and the transesterification reaction of 1,4-butanediol and an alkyl acrylate can be carried out in the presence of the collected dialkyltin oxide. At that time, it is preferred that the collected dialkyltin oxide is reused after the reaction system of the transesterification reaction of 1,4-butanediol and the alkyl acrylate is dried so that the water content in the reaction system is at most 1000 ppm, from the viewpoint of maintenance of catalytic activity.

As mentioned above, according to the process for preparing 4-hydroxybutyl acrylate of the present invention, the collected dialkyltin oxide can be repeatedly used until its catalytic activity is lost. Therefore, the process for preparing 4-hydroxybutyl acrylate of the present invention is excellent in industrial productivity.

The 4-hydroxybutyl acrylate collected in the above can be purified by distillation, washing and the like as occasion demands.

According to the process of the present invention, there can be obtained 4-hydroxybutyl acrylate having a content of acrylic acid, which is an acidic component, of not more than 50 ppm, preferably not more than 30 ppm, and more preferably not more than 15 ppm. Since the 4-hydroxybutyl acrylate has a low content of acrylic acid which is an acidic component, the 4-hydroxybutyl acrylate is low in skin irritation, and does not generate a rash and inflammation. Therefore, the 4-hydroxybutyl acrylate is useful, for example, as raw materials such as medical adhesives for cataplasm and the like, coating agents for electronic materials and photosensitive resin compositions, and the like.

[Fourth Invention]

The fourth invention is described below.

As described above, the process for preparing 4-hydroxybutyl acrylate according to the fourth present invention is a process for preparing 4-hydroxybutyl acrylate, including carrying out the transesterification reaction of 1,4-butanediol and an alkyl acrylate, characterized in that a dialkyltin oxide is used as a catalyst for transesterification; the transesterification reaction of 1,4-butanediol and an alkyl acrylate is carried out in the presence of a dialkyltin oxide as a catalyst for transesterification; the resulting reaction mixture containing 4-hydroxybutyl acrylate is extracted with an aliphatic or alicyclic hydrocarbon compound and water as an extractant at a temperature of 15 to 35° C.; the resulting water layer is extracted with an aromatic hydrocarbon compound as an extractant at a temperature of 15 to 65° C. from the aliphatic or alicyclic hydrocarbon compound layer and a water layer; and the resulting aromatic hydrocarbon layer is collected from the aromatic hydrocarbon layer and the water layer.

In the present invention, first of all, the transesterification reaction of 1,4-butanediol and an alkyl acrylate is carried out.

The alkyl acrylate includes, for example, an alkyl acrylate represented by the formula (I):

[Chem. 8]

$$CH_2=CHCOOR^1 \qquad (I)$$

wherein $R^1$ is an alkyl group having 1 to 4 carbon atoms, an alkyl acrylate represented by the formula (IV):

[Chem. 9]

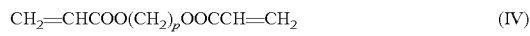

$$CH_2=CHCOO(CH_2)_pOOCCH=CH_2 \quad (IV)$$

wherein p is an integer of 1 to 8, and the like, and the present invention is not limited only to those exemplified ones. These alkyl acrylates can be used alone respectively, or at least of two kinds thereof can be used in combination.

The alkyl acrylate represented by the formula (IV) is an alkyl acrylate having an alkyl group of 1 to 4 carbon atoms. In the alkyl acrylate represented by the formula (IV), $R^1$ is an alkyl group having 1 to 4 carbon atoms. Concrete examples of the alkyl acrylate represented by the formula (IV) include, methyl acrylate, ethyl acrylate, propyl acrylate, n-butyl acrylate, isobutyl acrylate, tert-butyl acrylate, and the like. These alkyl acrylates can be used alone respectively, or at least two kinds thereof can be used in combination. Among the alkyl acrylate represented by the formula (IV), from the viewpoint of efficient separation of the resulting 4-hydroxybutyl acrylate from the alkyl acrylate, an alkyl acrylate having an alkyl group of 1 to 3 carbon atoms is preferable, and methyl acrylate is more preferable.

In the alkyl acrylate represented by the formula (IV), p is an integer of 1 to 8, and preferably an integer of 1 to 6, more preferably an integer of 1 to 4, furthermore preferably 4.

Among the alkyl acrylates, the alkyl acrylate represented by the formula (IV) is preferable from the viewpoint of efficient separation of the resulting 4-hydroxybutyl acrylate from the alkyl acrylate.

The amount of the alkyl acrylate per one mole of 1,4-butanediol is preferably at least 0.5 moles from the viewpoint of increase in reaction rate, and preferably at most 5 moles, more preferably at most 3 moles, from the viewpoint of lowering in the amount of an unreacted alkyl acrylates.

In the present invention, as a catalyst for transesterification, a dialkyltin oxide is used. There is one of great characteristics of the present invention in that the dialkyltin oxide is used as a catalyst for transesterification as mentioned above. Since the dialkyltin oxide which is excellent in catalytic activity is used as a catalyst in the present invention, 4-hydroxyalkyl acrylate can be efficiently prepared.

The dialkyltin oxides include, for example, dialkyltin oxides having an alkyl group of 4 to 18 carbon atoms, such as dibutyltin oxide, dioctyltin oxide and dilauryltin oxide, and the present invention is not limited only to those exemplified ones. These dialkyltin oxides can be used alone respectively, or at least two kinds thereof can be used in combination. Among these dialkyltin oxides, a dialkyltin oxide having an alkyl group of 4 to 12 carbon atoms is preferable, a dialkyltin oxide having an alkyl group of 4 to 8 carbon atoms is more preferable, dibutyltin oxide and dioctyltin oxide are further preferable, and dioctyltin oxide is furthermore preferable, from the viewpoint of acceleration of the transesterification reaction of 1,4-butanediol and the alkyl acrylate.

The amount of the dialkyltin oxide per one mole of the alkyl acrylate is at least 0.00001 moles, preferably at least 0.0001 moles, from the viewpoint of acceleration of the transesterification of 1,4-butanediol and the alkyl acrylate, and preferably at most 0.01 moles, more preferably at most 0.005 moles, from the viewpoint of suppress of the disproportionation reaction of 4-hydroxybutyl acrylate.

Incidentally, the disproportionation reaction of 4-hydroxybutyl acrylate means a reaction in which 4-hydroxybutyl acrylate is changed to 1,4-butanediol diacrylate and 1,4-butanediol.

When 1,4-butanediol is reacted with the alkyl acrylate, it is preferred that 1,4-butanediol is reacted with the alkyl acrylate in the presence of a reaction inhibitor from the viewpoint of suppression of polymerization of the alkyl acrylate.

The polymerization inhibitor includes, ones exemplified in the first invention. The polymerization inhibitor can be used alone in one kind, or at least two kinds thereof can be used in combination.

The amount of the polymerization inhibitor per 100 parts by mass of the alkyl acrylate is preferably at least 0.001 parts by mass, more preferably at least 0.005 parts by mass, furthermore preferably at least 0.01 parts by mass, from the viewpoint of suppression of polymerization of the alkyl acrylate, and preferably at most 5 parts by mass, more preferably at most 3 parts by mass, and furthermore preferably at most 1 part by mass, from the viewpoint of increase in purity of 4-hydroxybutyl acrylate.

Incidentally, when the transesterification reaction of 1,4-butanediol and the alkyl acrylate is carried out, an organic solvent can be used.

The organic solvent is preferably an organic solvent which is inactive in the reaction system of the transesterification reaction. As a preferred organic solvent, there can be exemplified ones used in the first invention. The organic solvents can be used only in one kind, or at least two kinds thereof can be used in combination.

The amount of the organic solvent is not particularly limited, and can be usually 5 to 200 parts by mass or so per 100 parts by mass of the total amount of 1,4-butanediol and the alkyl acrylate.

When the transesterification reaction of 1,4-butanediol and the alkyl acrylate is carried out, the reaction temperature is preferably at lowest 30° C., and more preferably at lowest 50° C., from the viewpoint of increase in reaction rate, and preferably at highest 150° C. from the viewpoint of inhibition of polymerization of the resulting 4-hydroxybutyl acrylate.

When the transesterification reaction of 1,4-butanediol and the alkyl acrylate is carried out, the atmosphere is preferably an atmosphere containing oxygen from the viewpoint of inhibition of polymerization of the alkyl acrylate, and more preferably a gas containing oxygen in a content of from 5% by volume to atmospheric concentration of oxygen from the viewpoint of enhancement of safety. Also, the pressure of the atmosphere is usually atmospheric pressure, and can be increased or reduced. For example, when the pressure of the atmosphere is reduced, there is a merit such that a side reaction can be suppressed, because the reflux temperature can be lowered.

When the transesterification reaction of 1,4-butanediol and the alkyl acrylate is carried out, the reaction time cannot be absolutely determined because the reaction time differs depending on the amounts of 1,4-butanediol and the alkyl acrylate, reaction temperature and the like. Therefore, the reaction time is usually controlled so that the transesterification reaction is completed. The end point of the transesterification reaction can be confirmed by, for example, gas chromatography, liquid chromatography and the like.

The transesterification reaction of 1,4-butanediol and the alkyl acrylate can be carried out by using a rectifying tower, a fluidized bed, a fixed bed, a reaction distillation column or the like, and the present invention is not limited only to those exemplified ones. In addition, the transesterification reaction of 1,4-butanediol and the alkyl acrylate can be carried out by any of a continuous method and a batch method.

In the progress of the transesterification reaction of 1,4-butanediol and the alkyl acrylate, an alcohol is generated as a by-product. It is usually preferred that the alcohol generated as a by-product is removed from the reaction system in order to accelerate the reaction. The alcohol generated as a by-product can be removed from the reaction system as, for example, an azeotropic mixture with an acrylate or a suitable solvent.

After the transesterification reaction of 1,4-butanediol and the alkyl acrylate, an organic solvent which is used in the reaction, an unreacted acrylate and an alcohol can be removed from the resulting reaction mixture, to collect an objective 4-hydroxybutyl acrylate. The removal of the unreacted acrylate and the alcohol can be carried out by distillation or extraction treatment.

In the present invention, there is one of characteristics of the present invention in that the reaction mixture containing 4-hydroxybutyl acrylate which is prepared by the transesterification of 1,4-butanediol and an alkyl acrylate is extracted with an aliphatic or alicyclic hydrocarbon compound and water as an extractant at a temperature of 15 to 35° C. Since the aliphatic or alicyclic hydrocarbon compound and water are used as an extractant, and the extraction operation of the above-mentioned reaction mixture is carried out at a specific temperature, 4-hydroxybutyl acrylate containing 1,4-butanediol diacrylate which is a by-product in a low content can be efficiently prepared, nevertheless the alkyltin oxide is used as a catalyst for transesterification.

In the description, the aliphatic or alicyclic hydrocarbon compound means an aliphatic hydrocarbon compound or an alicyclic hydrocarbon compound. In the description, the aliphatic or alicyclic hydrocarbon compound is described for convenience. The aliphatic hydrocarbon compound and the alicyclic hydrocarbon compound can be used alone or can be used in combination.

The aliphatic hydrocarbon compounds include, for example, aliphatic hydrocarbon compounds having 6 to 12 carbon atoms, such as n-hexane, n-heptane, n-octane, n-decane, isohexane, isooctane and isodecane, and the present invention is not limited only to those exemplified ones. These aliphatic hydrocarbon compounds can be used alone respectively, or at least two kinds thereof can be used in combination.

The alicyclic hydrocarbon compounds include, for example, alicyclic hydrocarbon compounds having 6 to 12 carbon atoms, such as cyclohexane, cycloheptane and cyclooctane, and the present invention is not limited only to those exemplified ones. These alicyclic hydrocarbon compounds can be used alone respectively, or at least two kinds thereof can be used in combination.

The amount of the aliphatic or alicyclic hydrocarbon compound per 100 mL (the milliliter) of the above-mentioned reaction mixture is preferably at least 50 mL, more preferably at least 100 mL and furthermore preferably at least 150 mL, from the viewpoint of efficient removal of 1,4-butanediol diacrylate, and preferably at most 300 mL, more preferably at most 250 mL and furthermore preferably at most 200 mL, from the viewpoint of efficient extraction of 4-hydroxybutyl acrylate. In addition, the amount of water per 100 mL of the above-mentioned reaction mixture is preferably at least 20 mL, more preferably at least 30 mL and furthermore preferably at least 40 mL, from the viewpoint of efficient extraction of 4-hydroxybutyl acrylate, and preferably at most 100 mL, more preferably at most 90 mL and furthermore preferably at most 80 mL, from the viewpoint of efficient removal of 1,4-butanediol diacrylate.

The extraction of 4-hydroxybutyl acrylate from the above-mentioned reaction mixture can be carried out by supplying the above-mentioned reaction mixture with the aliphatic or alicyclic hydrocarbon compound and water. Incidentally, it is preferred that the extraction of 4-hydroxybutyl acrylate from the above-mentioned reaction mixture is carried out by mixing the above-mentioned reaction mixture with the aliphatic or alicyclic hydrocarbon compound and water, and then the reaction mixture is allowed to stand.

When 4-hydroxybutyl acrylate is extracted from the above-mentioned reaction mixture, the extraction temperature is at lowest 15° C. and preferably at lowest 20° C., from the viewpoint of efficient removal of 1,4-butanediol diacrylate, and at highest 35° C., preferably at highest 30° C., from the viewpoint of efficient removal of the alkyltin oxide which is used as the catalyst for transesterification.

As mentioned above, by supplying the above-mentioned reaction mixture with the aliphatic or alicyclic hydrocarbon compound and water, mixing the above-mentioned reaction mixture with the aliphatic or alicyclic hydrocarbon compound and water, controlling the extraction temperature to a desired temperature, and allowing to stand the mixture, the water layer is separated from the aliphatic or alicyclic hydrocarbon compound layer. The 4-hydroxybutyl acrylate and 1,4-butanediol are mainly extracted to the water layer. The 1,4-butanediol diacrylate, the alkyl acrylate and the alkyltin oxide are mainly extracted to the aliphatic or alicyclic hydrocarbon compound layer.

The alkyltin oxide which is contained in the above-mentioned aliphatic or alicyclic hydrocarbon compound layer can be reused as a catalyst for transesterification by collecting the alkyltin oxide. When the alkyltin oxide is reused as a catalyst for transesterification, it is preferred that the alkyltin oxide is used after the water content in the transesterification reaction system is controlled to at most 1000 ppm, from the viewpoint of the maintenance of catalytic activity.

In addition, 1,4-butanediol diacrylate which is contained in the above-mentioned aliphatic or alicyclic hydrocarbon compound layer can be used as, for example, a crosslinking agent and the like by collecting 1,4-butanediol diacrylate.

Next, the above-mentioned water layer is collected from the above-mentioned aliphatic or alicyclic hydrocarbon compound layer and the water layer. The water layer is extracted at a temperature of 15 to 65° C. with an aromatic hydrocarbon compound, in order to remove 1,4-butanediol diacrylate which is contained in the water layer. The resulting aromatic hydrocarbon compound layer is collected from the aromatic hydrocarbon compound layer and the water layer.

In the present invention, there is one of characteristics of the present invention in that the above-mentioned water layer is extracted with an aromatic hydrocarbon compound as an extractant at a temperature of 15 to 65° C. Since the aromatic hydrocarbon compound is used as an extractant, and the extraction operation of the above-mentioned water layer is carried out at a specific temperature in the present invention, 4-hydroxybutyl acrylate can be efficiently prepared.

The aromatic hydrocarbon compound includes, for example, toluene, benzene, xylene, ethylbenzene and the like, and the present invention is not limited only to those exemplified ones. These aromatic hydrocarbon compounds can be used independently, or at least two kinds thereof can be used in combination.

The amount of the aromatic hydrocarbon compound per 100 mL of the above-mentioned water layer is preferably at least 100 mL, more preferably at least 150 mL and furthermore preferably at least 200 mL, from the viewpoint of efficient extraction of 4-hydroxybutyl acrylate, and preferably at most 500 mL, more preferably at most 450 mL and furthermore preferably at most 400 mL, from the viewpoint of efficient removal of 1,4-butanediol.

The extraction of 4-hydroxybutyl acrylate from the above-mentioned water layer can be carried out by supplying the above-mentioned water layer with an aromatic hydrocarbon compound. Incidentally, it is preferred that the extraction of 4-hydroxybutyl acrylate from the above-mentioned water layer is carried out by mixing the above-mentioned water layer with the aromatic hydrocarbon compound, and then the mixture is allowed to stand.

When 4-hydroxybutyl acrylate is extracted from the above-mentioned water layer, the extraction temperature is at lowest 15° C. from the viewpoint of efficient extraction of 4-hydroxybutyl acrylate, and at highest 65° C., preferably at highest 60° C., from the viewpoint of suppression of the scatter of the aromatic hydrocarbon compound which is used as an extractant.

As mentioned above, the water layer is separated from the aromatic hydrocarbon compound layer by supplying the above-mentioned water layer with the aromatic hydrocarbon compound as an extractant, mixing the water layer with the aromatic hydrocarbon compound, controlling the extraction temperature to a desired temperature, and allowing to stand the mixture. The 4-hydroxybutyl acrylate is mainly extracted to the aromatic hydrocarbon compound layer, and 1,4-butanediol is mainly extracted to the water layer.

The 1,4-butanediol which is contained in the above-mentioned water layer can be reused as, for example, a raw material of 4-hydroxybutyl acrylate and the like by collecting the 1,4-butanediol.

The 4-hydroxybutyl acrylate contained in the above-mentioned aromatic hydrocarbon compound layer can be used as it is, that is, as a solvent for a solution of the aromatic hydrocarbon compound. Alternatively, the 4-hydroxybutyl acrylate can be used after the aromatic hydrocarbon compound is removed from the aromatic hydrocarbon compound layer.

The 4-hydroxybutyl acrylate collected in the above can be purified by distillation, washing and the like as occasion demands. For example, when 1,4-butanediol is contained in 4-hydroxybutyl acrylate, there is a possibility that the 1,4-butanediol reacts with a multifunctional compound such as polyisocyanate compound, and forms a crosslinking structure, since 1,4-butanediol has two hydroxyl groups. Therefore, when 4-hydroxybutyl acrylate is used in the uses in which formation of a crosslinking structure is not appropriate, it is preferred that the 4-hydroxybutyl acrylate is washed with water and the like. In this case, 4-hydroxybutyl acrylate is washed until the content of 1,4-butanediol in the 4-hydroxybutyl acrylate becomes at most 0.1% by mass, in order to efficiently suppress the crosslinking reaction of 1,4-butanediol contained in the 4-hydroxybutyl acrylate.

As mentioned above, 4-hydroxybutyl acrylate obtained by the process of the present invention is useful raw materials such as coatings of automobiles, coatings for buildings, coating agents for electronic materials, photosensitive resin compositions, and the like.

[Fifth Invention]

The fifth invention is described below.

As mentioned above, the process for preparing a hydroxyalkyl acrylate of the fifth present invention relates to a process for preparing a hydroxyalkyl acrylate by carrying out the transesterification reaction of a polyhydric alcohol and an alkyl acrylate, characterized in that the resulting alcohol during the transesterification reaction of the polyhydric alcohol and the alkyl acrylate is collected by using a polyhydric alcohol.

In the present invention, at first, the transesterification reaction of the polyhydric alcohol and the alkyl acrylate is carried out.

It is preferred that the polyhydric alcohol is a polyhydric alcohol having an alkyl group corresponding to the alkyl group of an objective hydroxyalkyl acrylate, because the polyhydric alcohol is transformed into a hydroxyalkyl acrylate by the transesterification reaction with the alkyl acrylate. More specifically, it is preferred that the number of carbon atoms of the polyhydric alcohol is the same as the number of carbon atoms of the hydroxyalkyl acrylate from the viewpoint of preparation of an objective hydroxyalkyl acrylate.

The polyhydric alcohol includes, for example, aliphatic diols having carbon atoms of 2 to 8, such as ethylene glycol, 1,3-propanediol, 1,4-butanediol, 1,5-pentanediol and 1,6-hexanediol; aliphatic triols having 3 to 8 carbon atoms, such as glycerol, and the like, and the present invention is not limited only to those exemplified ones. These polyhydric alcohols can be used independently, or at least two kinds thereof can be used in combination. Among these polyhydric alcohols, aliphatic polyhydric alcohols having 2 to 4 carbon atoms is preferable, aliphatic diols having 2 to 4 carbon atoms are more preferable, and 1,4-butanediol is furthermore preferable.

The alkyl acrylate includes, for example, methyl acrylate, ethyl acrylate, propyl acrylate, n-butyl acrylate, isobutyl acrylate, tert-butyl acrylate and the like, and the present invention is not limited only to those exemplified ones. These alkyl acrylates can be used alone, or at least two kinds thereof can be used in combination. Among the alkyl acrylates, an alkyl acrylate having an alkyl group of 1 to 4 carbon atoms is preferable, an alkyl acrylate having an alkyl group of 1 to 3 carbon atoms is more preferable, and methyl acrylate is furthermore preferable.

The amount of the alkyl acrylate per one mole of the polyhydric alcohol is preferably at least 0.5 moles from the viewpoint of improvement in reaction rate, and preferably at most 5 moles, more preferably at most 3 moles, from the viewpoint of reduction of residual amount of an unreacted alkyl acrylate.

Incidentally, it is preferred that the transesterification reaction of the polyhydric alcohol and the alkyl acrylate is carried out in the presence of an organic solvent. Among the organic solvents, an organic solvent which is incompatible to the polyhydric alcohol is preferable from the viewpoint of efficient collection of the resulting alcohol generated as a by-product during the transesterification reaction of the polyhydric alcohol and alkyl acrylate.

Therefore, in the present invention, it is preferred that the transesterification reaction of the polyhydric alcohol and the alkyl acrylate is carried out in the presence of an organic solvent which is incompatible to the polyhydric alcohol from the viewpoint of efficient collection of the alcohol which is generated as a by-product during the transesterification reaction of the polyhydric alcohol and the alkyl acrylate.

Preferred organic solvents which are incompatible to the polyhydric alcohol include, for example, aliphatic hydrocarbon compounds having 6 to 8 carbon atoms, such as n-hexane, n-heptane and n-octane; alicyclic hydrocarbon compounds having 6 to 8 carbon atoms, such as cyclohexane and methylcyclohexane, and the like, and the present invention is not limited only to those exemplified ones. These organic solvents can be used alone, or at least two kinds thereof can be used in combination. Among the above-mentioned organic solvents, the alicyclic hydrocarbon compounds having 6 to 8 carbon atoms is preferable, cyclohexane and methylcyclohexane are more preferable, and cyclohexane is furthermore preferable, from the viewpoint of efficient removal of an alcohol which is generated as a by-product during the transesterification reaction of the polyhydric alcohol and the alkyl acrylate, and the organic solvent from the reaction system by forming an azeotropic mixture of the polyhydric alcohol and the alcohol.

In addition, from the viewpoint of efficient removal of an alcohol which is generated as a by-product during the transesterification reaction of the polyhydric alcohol, and the alkyl acrylate and the above-mentioned organic solvent from the reaction system of the transesterification reaction by forming an azeotropic mixture of the alcohol which is generated during the transesterification reaction and the above-mentioned organic solvent, it is desired that the polyhydric alcohol is an aliphatic polyhydric alcohol having 2 to 6 carbon atoms, and that the organic solvent which is incompatible to the polyhydric alcohol is at least one solvent selected from the group consisting of aliphatic hydrocarbon compounds having 6 to 8 carbon atoms and alicyclic hydrocarbon compounds having 6 to 8 carbon atoms, preferably the alicyclic hydrocarbon compounds having 6 to 8 carbon atoms among the above-mentioned organic solvents.

The amount of the organic solvent per 100 parts by mass of the total amount of the polyhydric alcohol and the alkyl acrylate is preferably at least 5 parts by mass, more preferably at least 10 parts by mass, from the viewpoint of efficient removal of an alcohol which is generated as a by-product during the transesterification reaction of the polyhydric alcohol and the alkyl acrylate, and the organic solvent from the reaction system of the transesterification reaction by forming an azeotropic mixture of the alcohol which is generated as a by-product during the transesterification reaction and the organic solvent, and preferably at most 300 parts by mass, more preferably at most 250 parts by mass, furthermore preferably at most 200 parts by mass, from the viewpoint of increase in efficiency of separation of the organic solvent from the alcohol which is generated as a by-product.

In the present invention, when the transesterification reaction of the polyhydric alcohol and the alkyl acrylate is carried out, a catalyst for transesterification can be used.

The catalyst for transesterification includes, for example, organotin compounds such as monomethyltin acid, monobutyltin oxide, monobutyltin hydrochloride, monobutyltin trioctoate, monobutyltin acid, monobutyltin tris(2-ethyl hexoate), butyltin trichloride, monobutyltin trimethylate, dibutyltin dilaurate, monophenyltin tribromide, dimethyltin oxide, dibutyltin oxide, dibutyltin dibromide, dibutyltin dichloride, dibutyltin diacetate, dibutyltin maleate, dibutyltin dithiol, dibutyltin bis(2-ethylhexoate), dibutyltin sulfide, tributyltin chloride, dioctyltin diacetate, dioctyltin oxide, dioctyltin dilaurate, dioctyltin dimethoxide, dioctyltin dibutoxide, diphenyltin dichloride, diphenyltin sulfide, diphenyltin dichloride, triphenyltin acetate, tetra-n-butyl-1,3-diacetoxy distannoxane, tetra-n-butyl-1,3-dioctyloxy distannoxane and tetra-n-butyl-1,3-dilauryloxy distannoxane; transition metal compounds such as titanium compounds such as tetraethyltitanate, tetraisopropyltitanate, tetrabutyltitanate, tetramethoxytitatnate and tetraethoxytitanate, thallium compounds, copper compounds, lead compounds, and chromium compounds; alkali metal alcoholates such as sodium methylate, sodium ethylate, lithium methylate and lithium ethylate; alkaline earth metal alcoholates such as calcium methylate, calcium ethylate, magnesium methylate and magnesium ethylate; aluminum alcoholates such as aluminum methylate and aluminum ethylate; lithium hydroxide, and the like. The present invention is not limited only to those exemplified ones. These catalysts for transesterification can be used alone, or at least two kinds thereof can be used in combination. Among the catalysts for transesterification, the dialkyltin oxide having an alkyl group of 4 to 12 carbon atoms is preferred, the dialkyltin oxide having an alkyl group of 4 to 8 carbon atoms is more preferred, dibutyltin oxide and dioctyltin oxide are further preferred, and dioctyltin oxide is furthermore preferred, from the viewpoint of acceleration of the transesterification reaction of the polyhydric alcohol and the alkyl acrylate.

The amount of the catalyst for transesterification per one mole of the alkyl acrylate is preferably at least 0.00001 moles, more preferably at least 0.0001 moles from the viewpoint of efficient progress of the transesterification reaction of the polyhydric alcohol and the alkyl acrylate, and preferably at most 0.01 moles, more preferably at most 0.005 moles from the viewpoint of inhibition of dismutation reaction of the resulting hydroxyalkyl acrylate. Incidentally, the dismutation reaction of the hydroxyalkyl acrylate is a reaction in which the hydroxyalkyl acrylate is changed into a diacrylate of a polyhydric alcohol and a polyhydric alcohol.

It is preferred that the transesterification reaction of the polyhydric alcohol and the alkyl acrylate is carried out in the presence of a polymerization inhibitor from the viewpoint of inhibition of polymerization of the alkyl acrylate.

As the polymerization inhibitor, there can be exemplified ones which are used in the first invention. The polymerization inhibitors can be used alone, or at least two kinds thereof can be used in combination.

The amount of the polymerization inhibitor per 100 parts by mass of the alkyl acrylate is preferably at least 0.001 parts by mass, more preferably at least 0.005 parts by mass, from the viewpoint of sufficient inhibition of the polymerization of the alkyl acrylate, and preferably at most 5 parts by mass, more preferably at most 3 parts by mass, furthermore preferably at most 1 part by mass, from the viewpoint of increase in purity of the resulting hydroxyalkyl acrylate.

When the transesterification reaction of the polyhydric alcohol and the alkyl acrylate is carried out, the reaction temperature is preferably at lowest 30° C., more preferably at lowest 50° C., from the viewpoint of increase in reaction rate, and preferably at highest 150° C. from the viewpoint of inhibition of the polymerization of the resulting hydroxyalkyl acrylate.

When the transesterification reaction of the polyhydric alcohol and the alkyl acrylate is carried out, the atmosphere is preferably an atmosphere which contains oxygen from the viewpoint of prevention of the polymerization of the alkyl acrylate, and more preferably a gas having an oxygen concentration of 5% by volume to an atmospheric concentration from the viewpoint of increase in safety. Also, the pressure of the atmosphere is usually atmospheric pressure, and can be increased or reduced. For example, when the pressure of the atmosphere is reduced, there is an advantage that a side-reaction can be restrained, because the reflux temperature can be lowered.

When the transesterification reaction of the polyhydric alcohol and the alkyl acrylate is carried out, the reaction time cannot be absolutely determined because the reaction time differs depending on the reaction temperature and the like. Therefore, the reaction time is usually selected so that the transesterification reaction is terminated. The end point of the transesterification reaction of the polyhydric alcohol and the alkyl acrylate can be confirmed by, for example, gas chromatography, liquid chromatography and the like.

The transesterification reaction of the polyhydric alcohol and the alkyl acrylate can be carried out by using, for example, a fractionator, a fluidized bed, a fixed bed, a reaction distillation column and the like, and the present invention is not limited only to those exemplified ones. In addition, the transesterification reaction of the polyhydric alcohol and the alkyl acrylate can be carried out by any of a circulation type and a batch type.

In the course of the progress of the transesterification reaction of the polyhydric alcohol and the alkyl acrylate, an alcohol is generated as a by-product. It is preferred that the alcohol which is generated as a by-product during the transesterification reaction is distilled away from the transesterification reaction system, from the viewpoint of efficient progress of the transesterification reaction of the polyhydric alcohol and the alkyl acrylate.

Incidentally, when the above-mentioned organic solvent is used in the transesterification reaction of the polyhydric alcohol and the alkyl acrylate is carried out, an alcohol generated as a by-product in the transesterification reaction can be distilled away together with the organic solvent from the transesterification reaction system. Since the distilled azeotropic mixture contains a valuable alcohol which is generated as a by-product, it is referred that the alcohol generated as a by-product is collected from the azeotropic mixture. In addition, since the above-mentioned azeotropic mixture contains a valuable organic solvent, it is preferred that the organic solvent is collected from the azeotropic mixture, and that the collected organic solvent is reused, for example, as an organic solvent which is used in the transesterification reaction of the polyhydric alcohol and the alkyl acrylate, and the like.

In the present invention, one of the great characteristics of the present invention resides in that an alcohol which is generated as a by-product during the transesterification reaction of the polyhydric alcohol and the alkyl acrylate is collected by using a polyhydric alcohol. When the alcohol which is generated as a by-product is collected by using the polyhydric alcohol, the collected alcohol contains little water. Therefore, the alcohol can be efficiently collected.

After the transesterification reaction of the polyhydric alcohol and the alkyl acrylate is carried out in the presence of an organic solvent which is incompatible to the polyhydric alcohol, and an azeotropic mixture containing an alcohol which is generated as a by-product during the transesterification reaction, and the organic solvent is distilled away from the reaction system of the transesterification reaction, it is preferred that the distilled azeotropic mixture is further mixed with a polyhydric alcohol in the present invention from the viewpoint of efficient collection of the alcohol which is generated as a by-product.

The above-mentioned azeotropic mixture usually contains the alcohol which is generated as a by-product and the organic solvent which is incompatible to the polyhydric alcohol. When the above-mentioned azeotropic mixture is mixed with the polyhydric alcohol, the alcohol which is generated as a by-product contained in this azeotropic mixture is extracted to the polyhydric alcohol. Therefore, an alcohol solution containing the alcohol generated as a by-product and the polyhydric alcohol is separated from the organic solvent which is incompatible to the polyhydric alcohol. Accordingly, when the alcohol solution is separated from the mixture obtained by mixing the above-mentioned azeotropic mixture with the polyhydric alcohol, the alcohol generated as a by-product can be efficiently collected under the condition of an alcohol solution.

As a polyhydric alcohol which is used when the azeotropic mixture is mixed with the polyhydric alcohol, there can be cited, for example, aliphatic diols having 2 to 8 carbon atoms, such as ethylene glycol, 1,3-propanediol, 1,4-butanediol, 1,5-pentanediol and 1,6-hexanediol; aliphatic triols having 3 to 8 carbon atoms, such as glycerol, and the like, and the present invention is not limited only to those exemplified ones. These polyhydric alcohols can be used alone, or at least two kinds thereof can be used in combination. Among these polyhydric alcohols, the aliphatic polyhydric alcohol having 2 to 4 carbon atoms is preferable, the aliphatic diol having 2 to 4 carbon atoms is more preferable, and butanediol is furthermore preferable, from the viewpoint of facilitation of collection of the polyhydric alcohol.

Also, it is preferred that the polyhydric alcohol which is used when the azeotropic mixture is mixed with the polyhydric alcohol is the same kind as the polyhydric alcohol which is used when the transesterification reaction of the polyhydric alcohol and alkyl acrylate is carried out, because the polyhydric alcohol can be reused as a polyhydric alcohol which is used in a new transesterification reaction of a polyhydric alcohol and an alkyl acrylate.

The amount of the polyhydric alcohol which is mixed with the azeotropic mixture is not particularly limited, and is preferably 10 to 100 parts by mass per 100 parts by mass of the azeotropic mixture from the viewpoint of efficient collection of an alcohol generated as a by-product.

Incidentally, the alcohol generated as a by-product, which is contained in the alcohol solution can be collected by distillation of the alcohol solution under reduced pressure.

A method for the distillation of the alcohol solution under reduced pressure is not particularly limited. As one method for the distillation of the alcohol solution under reduced pressure, there can be cited a method which includes heating the alcohol solution to an appropriate temperature within a range of 30 to 100° C., and reducing the surrounding atmosphere of the alcohol solution to not more than 500 kPa, and the present invention is not limited only to the exemplified one. After the distillation of the alcohol which is generated as a by-product from the alcohol solution, the remaining residue mainly contains a polyhydric alcohol. The residue can be used, for example, as a polyhydric alcohol which is used when a new transesterification reaction of a polyhydric alcohol and an alkyl acrylate is carried out. Also, the residue can be used as a raw material for preparing other organic compounds, and the like.

As described above, when the alcohol generated as a by-product and the residue which is obtained after the collection of the alcohol generated as a by-product from the alcohol solution containing the polyhydric alcohol are used in the transesterification reaction of a polyhydric alcohol and an alkyl acrylate, not only the alcohol generated as a by-product but also the collected residue are effectively used. Therefore, the amount of an effluent can be reduced. Accordingly, the process for preparing a hydroxyalkyl acrylate according to the present invention is a process friendly to environment.

On the other hand, after the termination of the transesterification reaction of a polyhydric alcohol and an alkyl acrylate, the resulting reaction mixture contains a hydroxyalkyl acrylate which is an objective compound in the present invention. When the transesterification reaction of a polyhydric alcohol and an alkyl acrylate is carried out, the alcohol generated as a by-product, a polyhydric alcohol, an organic solvent and the like are removed from the reaction system as an azeotropic mixture. Therefore, this reaction mixture mainly contains hydroxybutyl acrylate which is an objective compound, an unreacted acrylate, an organic solvent and the like. This reaction mixture can be used as it is in accordance with its purpose of use, or can be purified by, for example, a method for purification, such as distillation or extraction.

Also, the hydroxyalkyl acrylate can be collected by, for example, mixing the reaction mixture with an extractant containing water and an aliphatic hydrocarbon compound, to extract a hydroxyalkyl acrylate which is contained in the reaction mixture to a water layer, thereafter mixing the water layer with the extractant containing an aromatic hydrocarbon compound to extract the hydroxyalkyl acrylate which is contained in the water layer to the aromatic hydrocarbon compound.

The hydroxyalkyl acrylate collected in the above can be purified by distillation, washing and the like as occasion demands.

As explained above, according to the process for preparing a hydroxyalkyl acrylate of the present invention, an alcohol generated as a by-product when a hydroxyalkyl acrylate is prepared by a transesterification method can be efficiently collected. In addition, since the collected alcohol has a relatively high purity, the alcohol can be used as a raw material for preparing various organic compounds. Alternatively, the alcohol can be burned as a boiler fuel and the like. Furthermore, when the collected alcohol is burned, there is no necessity to use a special furnace such as an incinerator for waste water, which has been conventionally used, and also there is no necessity to burn water which is contained in an aqueous alcohol solution. Therefore, consumption of energy can be reduced, and moreover running cost can be reduced.

[Sixth Invention]

Hereinafter, the sixth invention is described.

Since methyl(meth)acrylate is a compound sensitive to temperatures, and is easily polymerized, in order to prevent the methyl(meth)acrylate from polymerization, as a method for collecting methyl(meth)acrylate remaining in a reactor, it can be thought a method for collecting methyl(meth)acrylate by carrying out vacuum distillation of methyl(meth)acrylate at a low temperature.

However, when methyl(meth)acrylate is collected by carrying out the vacuum distillation of methyl(meth)acrylate at a low temperature, it is difficult to trap the vapor of methyl(meth)acrylate with a condenser, because the boiling point of methyl(meth)acrylate is low, and the vapor pressure of methyl(meth)acrylate is high, and the vapor is easily scattered to the air. Therefore, there are some possibilities such that not only methyl (meth)acrylate cannot be efficiently collected, but also a bad smell due to methyl(meth)acrylate is given off. In order to prevent the vapor of methyl(meth)acrylate from scattering to the air, it is considered to provide a condenser with an exhaust gas processor. However, when the exhaust gas processor is used, there arise secondary problems such as treatment of waste fluid generated in the exhaust gas processor, costs of equipment for using the exhaust gas processor, and increase of the expenses such as maintenance costs.

Therefore, the present inventors have earnestly studied. As a result, they have eventually found out that methyl(meth)acrylate remaining in the reactor can be efficiently collected from the reactor under atmospheric pressure without the above-mentioned vacuum operation, when as a solvent, an azeotropic solvent which forms an azeotropic mixture with methyl alcohol at a temperature of not higher than the boiling point of methyl alcohol, and which forms an azeotropic mixture with methyl(meth)acrylate at a temperature of not higher than the boiling point of methyl(meth)acrylate is used, the transesterification reaction of methyl(meth)acrylate and an alcohol which corresponds to an objective (meth)acrylate is carried out, and thereafter the resulting reaction mixture is heated to form an azeotropic mixture of methyl(meth)acrylate existing in the reactor and the above-mentioned azeotropic solvent. Moreover, it has been found out that the collected methyl(meth)acrylate can be used as a raw material when a new transesterification reaction of methyl(meth)acrylate and an alcohol corresponding to an objective (meth)acrylate is carried out.

Therefore, according to the method for preparing a (meth)acrylate of the present invention, methyl(meth)acrylate remaining in a reactor can be efficiently collected under atmospheric pressure without the necessity of a vacuum operation. Moreover, the collected methyl (meth)acrylate can be reused. Accordingly, the process for preparing a (meth)acrylate of the present invention is a process excellent in industrial productivity.

As described above, the process for preparing a (meth)acrylate of the present invention is a process for preparing am objective (meth)acrylate, which includes using methyl(meth)acrylate as a raw material, carrying out the transesterification reaction of methyl (meth)acrylate and an alcohol which corresponds to an objective (meth)acrylic acid ester, to prepare an objective (meth)acrylate, characterized in that a reactor having a distillation column is used as a reactor; when the transesterification reaction of methyl(meth)acrylate and an alcohol which corresponds to an objective (meth)acrylate is carried out in the reactor, an azeotropic solvent which forms an azeotropic mixture with methyl alcohol at a temperature of not higher than the boiling point of the methyl alcohol and which forms an azeotropic mixture with methyl (meth)acrylate at a temperature of not higher than the boiling point of the methyl(meth)acrylate is used; after the transesterification reaction of methyl(meth)acrylate and the alcohol which corresponds to the objective (meth)acrylate, the resulting reaction mixture is further heated; and vapor containing unreacted methyl(meth)acrylate is taken out from the upper portion of the distillation column.

In the present invention, when the transesterification reaction of methyl(meth)acrylate and an alcohol which corresponds to the objective (meth)acrylate is carried out, a reactor equipped with a distillation column is used as a reactor.

The reactor equipped with a distillation column includes, for example, a rectifying tower, a fluidized bed, a fixed bed, a reaction distillation column and the like, and the present invention is not limited only to those exemplified ones. Also, there is no limitation in the structure and type of the distillation column. Among the distillation columns, one having high gas-liquid contact efficiency is preferable. The preferred distillation column includes, for example, a packed-column type distillation column, a tray type distillation column and the like. The theoretical plate number of the distillation column is preferably at least 7, more preferably at least 10, furthermore preferably at least 15, from the viewpoint of efficient and stable progress of the transesterification reaction of methyl(meth)acrylate and the alcohol which corresponds to the objective (meth)acrylate, and preferably at most 100, more preferably at most 70, furthermore preferably at most 50, from the viewpoint of increase in economic efficiency.

The transesterification reaction of methyl(meth)acrylate and the alcohol which corresponds to the objective (meth)acrylate can be carried out by any of a circulation type and a batch type.

In the present invention, first of all, the transesterification reaction of methyl(meth)acrylate and the alcohol which corresponds to the objective (meth)acrylate is carried out.

When the transesterification reaction of methyl(meth)acrylate and the alcohol is carried out, the alcohol is selected so that the alcohol corresponds to an objective (meth)acrylate. More specifically, as the above-mentioned alcohol, an alcohol which forms an ester group of the objective (meth)acrylate is used. As one embodiment, for example, when the objective (meth)acrylate is n-propyl(meth)acrylate, n-propyl alcohol is used as an alcohol which forms the propyl group.

The alcohol corresponding to the objective (meth)acrylate includes, for example, aliphatic or alicyclic alcohols represented by the formula (V):

[Chem. 10]

$$R^6OH \quad\quad\quad (V)$$

wherein $R^6$ is an alkyl group having 2 to 30 carbon atoms, which may have a ring structure, such as ethyl alcohol, n-propyl alcohol, isopropyl alcohol, n-butyl alcohol, isobutyl alcohol, sec-butyl alcohol, tert-butyl alcohol, n-pentyl alcohol, n-hexyl alcohol, isohexyl alcohol, cyclohexyl alcohol, 3,3,5-trimethylcyclohexyl alcohol, 4-tert-butylcyclohexyl alcohol, n-heptyl alcohol, n-octyl alcohol, isooctyl alcohol, 2-ethylhexyl alcohol, 3,4-dimethylhexyl alcohol, 3,4-dimethylheptyl alcohol, lauryl alcohol, nonyl alcohol, isononyl alcohol, stearyl alcohol and 2-heptylundecane-1-ol; aromatic alcohols such as phenol, benzyl alcohol, 1-phenylethyl alcohol, 2-phenylethyl alcohol and phenoxyethanol; amino alcohols represented by the formula (VI):

[Chem. 11]

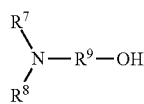

(VI)

wherein each of $R^7$ and $R^8$ is independently hydrogen atom or an alkyl group having 1 to 8 carbon atoms, and $R^9$ is an alkylene group having 1 to 4 carbon atoms, such as dimethylaminoethyl alcohol, diethylaminoethyl alcohol, dipropylaminoethyl alcohol, dibutylaminoethyl alcohol, dipentylaminoethyl alcohol, dihexylaminoethyl alcohol, dioctylaminoethyl alcohol, methylethylaminoethyl alcohol, methylpropylaminoethyl alcohol, methylbutylaminoethyl alcohol, methylhexylaminoethyl alcohol, ethylpropylaminoethyl alcohol, ethylbutylaminoethyl alcohol, ethylpentylaminoethyl alcohol, ethyloctylaminoethyl alcohol, propylbutylaminoethyl alcohol, dimethylaminopropyl alcohol, diethylaminopropyl alcohol, dipropylaminopropyl alcohol, dibutylaminopropyl alcohol and butylpentylaminopropyl alcohol; monohydric alcohols, such as alkoxy alcohols such as 2-methoxyethyl alcohol, ethoxyethyl alcohol, butoxyethyl alcohol, ethyleneglycol monomethyl ether, ethyleneglycol monoethyl ether (ethyl carbitol), triethyleneglycol monomethyl ether, tetrahydrofurfuryl alcohol, 2-ethyl-2-methyl-1,3-dioxolane-4-methyl alcohol, cyclohexane spiro-2-1,3-dioxolane-4-methyl alcohol, 3-methyl-3-oxetanylmetyl alcohol and 3-ethyl-3-oxetanylmetyl alcohol; ally alcohol, metallyl alcohol and tetrahydrofurfuryl alcohol; dihydric alcohols such as ethylene glycol, 2,3-propanediol, 1,3-butanediol, 1,4-butanediol, 1,6-hexanediol, trimethylolpropane and cyclohexanediol; polyhydric alcohols having at least three hydroxyl groups, such as glycerol, and the like, and the present invention is not limited only to those exemplified ones. These alcohols can be used alone respectively, or at least two kinds thereof can be used in combination, The amount of methyl(meth)acrylate per one equivalent of hydroxyl group of an alcohol which corresponds to an objective (meth)acrylate is preferably at least 0.3 equivalents, more preferably at least 0.5 equivalents, furthermore preferably at least 0.8 equivalents, from the viewpoint of increase in reaction rate of the transesterification reaction of methyl(meth)acrylate and the alcohol, and preferably at most 5 equivalents, more preferably at most 4 equivalents, furthermore preferably at most 3 equivalents, from the viewpoint of reduce in the amount of unreacted methyl (meth)acrylate.

When the transesterification reaction of methyl(meth)acrylate and the alcohol which corresponds to the objective (meth)acrylate is carried out, a catalyst for transesterification can be used.

The catalyst for transesterification includes, for example, hydroxides such as lithium hydroxide, sodium hydroxide, potassium hydroxide, cesium hydroxide, magnesium hydroxide, calcium hydroxide, barium hydroxide and strontium hydrate; hydrogen carbonates such as lithium hydrogen carbonate, sodium hydrogen carbonate, potassium hydrogen carbonate, cesium hydrogen carbonate, magnesium hydrogen carbonate, calcium hydrogen carbonate, barium hydrogen carbonate and strontium hydrogen carbonate; carbonates such as lithium carbonate, sodium carbonate, potassium carbonate, cesium carbonate, magnesium carbonate, calcium carbonate, barium carbonate and strontium carbonate; acetates such as lithium acetate, sodium acetate, potassium acetate, cesium acetate, magnesium acetate, calcium acetate, barium acetate and strontium acetate; borohydride compounds such as lithium borohydride, sodium borohydride, potassium borohydride and cesium borohydride; stearates such as lithium stearate, sodium stearate, potassium stearate, cesium stearate, magnesium stearate, calcium stearate, barium stearate and strontium stearate; phenylboron compounds such as lithium boron phenylate, sodium boron phenylate, potassium boron phenylate and cesium boron phenylate; benzoates such as lithium benzoate, sodium benzoate, potassium benzoate and cesium benzoate; hydrogen phosphate compounds such as dilithium hydrogen phosphate, disodium hydrogen phosphate, dipotassium hydrogen phosphate and dicesium hydrogen phosphate; phenylphosphates such as dilithium phenylphosphate, disodium phenylphosphate, dipotassium phenylphosphate and dicesium phenylphosphate; metal alkoxides such as sodium alkoxide and titanium alkoxide; tetraalkoxy titaniums such as tetramethoxy titanium, tetraethoxy titanium, tetrapropoxy titanium and tetrabutoxy titanium; dialyltin oxides such as dialyltin oxides having an alkyl group of 4 to 18 carbon atoms, such as dibutyltin oxide, dioctyltin oxide and dilauryltin oxide; metal alcoholates such as titanium alcoholate, aluminum alcoholate and magnesium alcoholate, and the like, and the present invention is not limited only to those exemplified ones. These catalysts for transesterification can be used alone respectively, or at least two kinds thereof can be used in combination. Among these catalysts for transesterification, from the viewpoint of acceleration of the transesterification reaction, a tetraalkoxy titanium and a dialkyltin oxide having an alkyl group of 4 to 12 carbon atoms are preferable, the tetraalkoxy titanium and the dialkyltin oxide having an alkyl group of 4 to 8 carbon atoms are more preferable, and tetramethoxy titanium, dibutyltin oxide and dioctyltin oxide are furthermore preferable.

The amount of the catalyst for transesterification cannot be absolutely determined because the amount differs depending on the kind of the catalyst for transesterification. Therefore, it is preferred that the amount of the catalyst for transesterification is determined in accordance with the kind of the catalyst for transesterification. The amount of the catalyst for transesterification is usually preferably at least 0.00001 moles, more preferably at least 0.0001 moles, from the viewpoint of efficient progress of the transesterification reaction of methyl(meth)acrylate and the alcohol, and preferably at most 0.10 moles, more preferably at most 0.05 moles, from the viewpoint of increase in economic efficiency.

In addition, when the transesterification reaction of methyl (meth)acrylate and the alcohol is carried out, a polymerization inhibitor can be used. As the polymerization inhibitor, there can be exemplified ones which can be used in the first invention. The polymerization inhibitors can be used only in one kind, or at least two kinds thereof can be used in combination.

The amount of the polymerization inhibitor per 100 parts by mass of methyl(meth)acrylate is preferably at least 0.00001 parts by mass, more preferably at least 0.00005 parts by mass, and furthermore preferably at least 0.0001 parts by mass, from the viewpoint of inhibition of polymerization of methyl(meth)acrylate used as a raw material and the resulting alkyl acrylate, and is preferably at most 0.1 parts by mass, more preferably at most 0.05 parts by mass, and furthermore preferably at most 0.01 parts by mass, from the viewpoint of enhancement of the purity of the resulting alkyl acrylate.

When the transesterification reaction of methyl(meth) acrylate and the alcohol which forms an azeotropic mixture with methyl alcohol is carried out in a reactor, as a solvent, an azeotropic solvent which forms an azeotropic mixture with methyl alcohol at a temperature of not higher than the boiling point of methyl alcohol, and which forms an azeotropic mixture with methyl(meth)acrylate at a temperature of not higher than the boiling point of methyl(meth)acrylate is used. In the present invention, since the azeotropic solvent which forms an azeotropic mixture with methyl alcohol at a temperature of not higher than the boiling point of methyl alcohol, and which forms an azeotropic mixture with methyl (meth)acrylate at a temperature of not higher than the boiling point of methyl(meth)acrylate is used as mentioned above, after the transesterification reaction of methyl (meth) acrylate and the alcohol which corresponds to the objective (meth)acrylate is carried out, methyl(meth)acrylate existing in the reactor can be efficiently collected from the reactor.

Incidentally, the above-mentioned methyl alcohol is an alcohol which is generated as a by-product when the transesterification reaction of methyl(meth)acrylate and the alcohol which corresponds to the objective (meth)acrylate is carried out.

The azeotropic solvent which forms an azeotropic mixture with methyl alcohol at a temperature of not higher than the boiling point of methyl alcohol and which forms an azeotropic mixture with methyl (meth)acrylate at a temperature of not higher than the boiling point of methyl(meth)acrylate includes, for example, cyclohexane, n-hexane and the like, and the present invention is not limited only to those exemplified ones. These azeotropic solvents can be used alone respectively or in combination. Among these azeotropic solvents, from the viewpoint of shortening of the reaction time of transesterification and efficient collection of methyl (meth)acrylate, cyclohexane is preferable.

The amount of the azeotropic solvent is not particularly limited, and can be usually 5 to 200 parts by mass or so per 100 parts by mass of the total amount of methyl(meth) acrylate and the alcohol which corresponds to the objective (meth)acrylate.

Incidentally, the other solvent can be used within a scope which does not hinder an object of the present invention. The other solvent includes, for example, aliphatic hydrocarbon compounds having 5 to 8 carbon atoms other than cyclohexane, such as n-pentane, n-hexane, isohexane, n-heptane, n-octane, 2,3-dimethylbutane, 2,5-dimethylhexane and 2,2, 4-trimethylpentane, and the present invention is not limited only to those exemplified ones.

It is preferred that the azeotropic mixture of the azeotropic solvent and methyl alcohol generated as a by-product is formed, and that the vapor of the methyl alcohol generated as a by-product is removed from the upper portion of the distillation column attached to the reactor, preferably the overhead of the distillation column from the viewpoint of efficient transesterification reaction of methyl(meth)acrylate and the alcohol which corresponds to the objective (meth) acrylate. It is preferred that the temperature at the overhead of the distillation column is controlled to a temperature which is included in a range of from a temperature when an azeotropic mixture of methyl alcohol and the azeotropic solvent is formed to a temperature of 5° C. higher, preferably 2° C. higher than the temperature when an azeotropic mixture of methyl alcohol and the azeotropic solvent is formed, from the viewpoint of efficient removal of the azeotropic solvent and methyl alcohol from the reactor.

During the transesterification reaction of methyl(meth) acrylate and the alcohol which corresponds to the objective (meth)acrylate, methyl alcohol can be collected as a condensate by taking out vapor from the upper portion of the above-mentioned distillation column, and condensing the vapor. When a part of the condensate is refluxed to the distillation column, and the remaining condensate is removed from the reactor, the temperature of the upper portion of the distillation column can be easily controlled to a temperature at which an azeotropic mixture is formed without the control of the heating temperature of the reactor.

The condensate removed from the reactor can be separated into two layers of an upper layer and a lower layer by adding water to the condensate. The amount of water to be added to the condensate per 100 parts by volume of the condensate is not particularly limited, and is usually preferably at least 10 parts by volume, more preferably at least 20 parts by volume, from the viewpoint of efficient separation of the upper layer from the lower layer, and preferably at most 300 parts by volume, more preferably at most 200 parts by volume, from the viewpoint of decrease of the amount of the resulting lower layer.

Incidentally, when water is added to the condensate, the temperature of the condensate is preferably 0 to 50° C., more preferably 0 to 40° C., furthermore preferably 0 to 30° C., from the viewpoint of efficient separation of the condensate into an upper layer and a lower layer.

When the condensate is separated into the upper layer and the lower layer, a separator such as a decanter or a separating funnel can be used.

In the separated two layers, the upper layer mainly contains the azeotropic solvent. The azeotropic solvent contained in the upper layer can be effectively used as a solvent when the transesterification reaction of methyl (meth)acrylate and the alcohol which corresponds to the objective (meth)acrylate is carried out.

Accordingly, it is preferred in the present invention that the above-mentioned upper layer is refluxed to the distillation column from the viewpoint of effective utilization of the azeotropic solvent contained in the above-mentioned upper layer. When the above-mentioned upper layer is supplied to the distillation column, it is preferred that the upper layer is supplied to the distillation column at the middle position from the viewpoint of efficient acceleration of the transesterification reaction of methyl (meth)acrylate and the alcohol. Incidentally, the middle position of the above-mentioned distillation column means a position neighborhood of the central of the multi-staged distillation column. For example, when the distillation column has theoretical stages of 15 stages, 6 to 9 stages thereof correspond to the middle position.

In addition, the ability for fractionation of the distillation column can be enhanced by refluxing a part of the condensate to the distillation column. The amount of the condensate which is refluxed to the overhead of the distillation column is not particularly limited, and is preferably 20 to 95% by mass or so of the total amount of the condensate, more preferably 50 to 90% by mass or so of the total amount of the condensate, from the viewpoint of enhancement in ability for fractionation of the distillation column and increase in reaction rate.

When a part of the condensate of vapor which is taken out from the upper portion of the distillation column is refluxed to the overhead of the distillation column, it is preferred that water is added to the remaining condensate in the same manner as mentioned above, and the remaining condensate is separated into two layers of an upper layer and a lower layer. The upper layer separated from the two layers mainly contains the azeotropic solvent. Therefore, the upper layer can be effectively used as a reaction solvent in the same manner as mentioned in the above when the transesterification reaction of methyl(meth)acrylate and the alcohol which corresponds to the objective (meth)acrylate is carried out. At that time, it is preferred that the above-mentioned upper layer is supplied to the middle portion of the distillation column in the same manner as mentioned above from the viewpoint of efficient acceleration of the transesterification reaction of methyl(meth)acrylate and the alcohol.

On the other hand, the above-mentioned lower layer mainly contains methyl alcohol and water, and also contains the azeotropic solvent and methyl(meth)acrylate in a content of 1 to 10% by mass or so, respectively, other than these components.

When the above-mentioned lower layer is distilled, the azeotropic solvent and methyl(meth)acrylate form an azeotropic mixture together with methyl alcohol, and can be removed from the lower layer as an azeotropic mixture.

It is preferred that water is added to the condensate which is removed from the reactor, the condensate is separated into two layers of an upper layer and a lower layer, and a distillation apparatus having a distillation column is charged with the lower layer separated from the two layers, to distill the lower layer. When this lower layer is distilled, vapor containing methyl(meth)acrylate and methyl alcohol which is generated as a by-product are firstly generated by controlling the temperature of the overhead of distillation column to not higher than 64° C. Thereafter, by controlling the temperature of the lower layer to 64 to 66° C., vapor mainly containing methyl alcohol which is generated as a by-product in the transesterification reaction can be generated. The generated vapor can be taken out from the upper portion of the distillation column.

The above-mentioned lower layer can be distilled by using a distillation apparatus having a distillation column. The distillation apparatus can be any type of a continuous method type and a batch method type. In addition, when the above-mentioned lower layer is distilled, the pressure can be any of atmospheric pressure and reduced pressure. The theoretical plate number of the distillation column which is used in the distillation is preferably at least 5, more preferably at least 7, furthermore preferably at least 10, from the viewpoint of efficient formation of an azeotropic mixture of the azeotropic solvent, methyl(meth)acrylate and methyl alcohol, and preferably at most 100, more preferably at most 70, furthermore preferably at most 50, from the viewpoint of increase in economic efficiency. Also, when the above-mentioned lower layer is distilled, the distillation temperature is preferably at lowest 20° C., more preferably at lowest 40° C., furthermore preferably at lowest 50° C., and from the viewpoint of the prevention of methyl(meth)acrylate from polymerization, preferably at highest 120° C., more preferably at highest 110° C., furthermore preferably at highest 105° C.

Since the vapor containing methyl(meth)acrylate, methyl alcohol which is generated as a by-product and the azeotropic solvent includes the azeotropic solvent, methyl(meth)acrylate and methyl alcohol, it is preferred that the vapor is condensed, and the resulting condensate is used as a raw material when the transesterification reaction of methyl (meth)acrylate and the alcohol which corresponds to the objective (meth)acrylate is carried out, from the viewpoint of reduction in amounts of waste. In addition, after the above-mentioned vapor is condensed, and the resulting condensate is distilled, to separate methyl alcohol and water from the condensate, it is preferred that the condensate from which methyl alcohol and water are separated is used as a raw material when the transesterification reaction of methyl (meth)acrylate and the alcohol which corresponds to the objective (meth)acrylate is carried out, from the viewpoint of efficient use of the condensate without the inclusion of methyl alcohol which is generated as a by-product and water. The separated methyl alcohol and water can be used, for example, as the water for adding to the condensate which is removed from the reactor. In addition, methyl alcohol can be easily separated from water by, for example, purification by distillation, and the like. Since methyl alcohol which is separated from the water contained in the residue does not contain impurities other than water, the methyl alcohol can be used as, for example, an industrial raw material, a solvent and the like, as well as methyl alcohol which has been usually used.

Incidentally, when the transesterification reaction of methyl(meth)acrylate and the alcohol is carried out, the reaction temperature is preferably at lowest 70° C., more preferably at lowest 75° C., from the viewpoint of increase in reaction rate, and preferably at highest 140° C., more preferably at highest 130° C., furthermore preferably at highest 120° C., from the viewpoint of prevention of methyl (meth)acrylate which is used as a raw material and the resulting (meth)acrylate from polymerization.

When the transesterification reaction of methyl(meth) acrylate and the alcohol is carried out, the atmosphere is preferably an atmosphere which contains oxygen from the viewpoint of prevention of methyl (meth)acrylate which is used as a raw material and the resulting (meth)acrylate from polymerization, and more preferably a gas having an oxygen concentration of 5% by volume to an atmospheric concentration, from the viewpoint of increase in safety. Also, the pressure of the atmosphere is usually atmospheric pressure, and can be increased or reduced. For example, when the pressure of the atmosphere is reduced, there is an advantage that a side-reaction can be restrained, because the reflux temperature can be lowered.

In the course of the progress of the transesterification reaction of methyl(meth)acrylate and the alcohol, the generating rate of methyl alcohol as a by-product is lowered. The transesterification reaction can be terminated at the time when the rate of reaction attains to a predetermined value. Incidentally, methyl(meth)acrylate disappears from the reactor due to the formation of an azeotropic mixture together with an azeotropic solvent. When the methyl(meth)acrylate disappears from the reactor, the temperature at the overhead of the distillation column finally attains to the boiling point of the azeotropic mixture. Therefore, the disappearance of methyl(meth)acrylate can be confirmed by measuring the temperature at the overhead of the distillation column. For example, the transesterification reaction of methyl(meth) acrylate and the alcohol can be terminated at the time when the temperature at the overhead of the distillation column attains to a temperature about 5° C. higher than the azeotropic temperature of the azeotropic solvent and methyl alcohol. The end point of transesterification reaction of methyl(meth)acrylate and the alcohol can be confirmed by, for example, gas chromatography, liquid chromatography and the like.

When the transesterification reaction of methyl(meth) acrylate and the alcohol is carried out, the reaction time cannot be absolutely determined because the reaction time differs depending on the amounts of methyl(meth)acrylate and the alcohol, reaction temperature and the like. Therefore, the reaction time is usually controlled so that the reaction ratio is attained to an intended value.

As described above, when the transesterification reaction of methyl(meth)acrylate and the alcohol is carried out, an objective (meth)acrylate can be obtained.

After the transesterification reaction of methyl(meth)acrylate and the alcohol which corresponds to the objective (meth)acrylate is carried out, the resulting reaction mixture is further heated, to take out the vapor containing unreacted methyl(meth)acrylate from the upper portion of the distillation column. In the present invention, there is one of great characteristics in that after the transesterification reaction is carried out as mentioned above, the reaction mixture in the reactor is further heated, to take out the vapor containing unreacted methyl(meth)acrylate from the upper portion of the distillation column. Since the above-mentioned operation is employed in the present invention, methyl(meth) acrylate which is used as a raw material can be efficiently collected from the reactor.

When the reaction mixture contained in the reactor is further heated after the transesterification reaction of methyl (meth)acrylate and the alcohol is terminated, the heating temperature cannot be absolutely determined, because the temperature differs depending on the kind of the azeotropic solvent being used. The heating temperature is usually a temperature at the transesterification reaction of methyl (meth)acrylate and the alcohol, and preferably at lowest 70° C., more preferably at lowest 75° C., and from the viewpoint of prevention of methyl(meth)acrylate which is used as a raw material and the resulting (meth)acrylate from polymerization, preferably at highest 140° C., more preferably at highest 130° C., furthermore preferably at highest 120° C. In addition, when the reaction mixture contained in the reactor is heated, the pressure can be controlled to atmospheric pressure. Therefore, there is no necessity to control the pressure to an increased pressure or a lowered pressure. The pressure can be higher or lower than the atmospheric pressure as occasion demands.

The vapor generated by heating the reaction mixture in the reactor is taken out from the upper portion of the reactor, preferably the overhead of the reactor to the outside of the reactor, and cooled to collect as a condensate.

When the vapor generated by heating the reaction mixture in the reactor is taken out from the reactor, since the vapor contains an azeotropic solvent, the azeotropic solvent is taken out from the reactor together with methyl(meth) acrylate, and the amount of the azeotropic solvent existing in the reactor is reduced. Therefore, in order to efficiently form an azeotropic mixture of methyl(meth)acrylate and the azeotropic solvent, the azeotropic solvent can be added to the reactor as occasion demands. The amount of the azeotropic solvent is not particularly limited, and is usually an amount which facilitates the formation of an azeotropic mixture of methyl(meth)acrylate and the azeotropic solvent.

Incidentally, the terminal point of the operation for forming an azeotropic mixture of methyl(meth)acrylate and the azeotropic solvent is not particularly limited. In accordance with the decrease of the amount of methyl(meth)acrylate remaining in the reactor, the azeotropic temperature of the azeotropic mixture approaches the boiling point of the azeotropic solvent. Therefore, it is preferred that the operation for forming an azeotropic mixture is carried out until the temperature of the azeotropic mixture attains to the boiling point of the azeotropic solvent.

The condensate collected in the above mainly contains collected methyl(meth)acrylate, the azeotropic solvent and methyl alcohol which is generated as a by-product in the transesterification reaction. The amount of the methyl alcohol generated as a by-product is lower than the amount of the collected methyl(meth)acrylate and the azeotropic solvent. Therefore, the condensate can be effectively used as methyl (meth)acrylate which is used as a raw material when a new transesterification reaction is carried out.

The objective (meth)acrylate is contained in the reaction mixture in the reactor. The reaction mixture can be taken out from the reactor, for example, from the lower portion thereof. The reaction mixture contains the azeotropic solvent which is used in the transesterification reaction, a slight amount of unreacted methyl(meth)acrylate and methyl alcohol generated as a by-product, other than the objective (meth)acrylate. Therefore, (meth)acrylate which is an objective compound can be collected by removing these compounds from the reaction mixture as occasion demands. The removal of unreacted methyl(meth)acrylate, the azeotropic solvent and methyl alcohol generated as a by-product from the reaction mixture can be easily carried out by distillation, extraction and the like.

As mentioned above, methyl(meth)acrylate can be efficiently collected.

The above-mentioned methyl(meth)acrylate is a substance exerting bad smell. When the methyl(meth)acrylate is discharged to the atmosphere, methyl(meth)acrylate exerts strong bad smell. Therefore, it is necessary not to discharge methyl(meth)acrylate to the atmosphere, or to reduce the amount of methyl(meth)acrylate which is discharged to the atmosphere as much as possible.

In contrast, according to the present invention, methyl (meth)acrylate remaining in the reaction mixture after the transesterification reaction can be mildly and easily removed by forming an azeotropic mixture together with an azeotropic solvent under the atmospheric pressure. Therefore, the amount of methyl(meth)acrylate which is discharged to the atmosphere can be extremely reduced.

Accordingly, it can be said that the process for preparing a (meth)acrylate of the present invention is an environmentally conscious and environment-friendly process.

Incidentally, the above-mentioned reactor can be equipped with, for example, an alkaline scrubber and the like at the exhaust port of the reactor as occasion demands, to absorb methyl(meth)acrylate to reduce the amount of methyl(meth)acrylate which is discharged to the air.

The (meth)acrylate obtained according to the process for preparing a (meth)acrylate is a compound useful as, for example, a raw material such as (meth)acrylic resins, surfactants, adhesive agents, coatings and the like.

In addition, according to the kind of an objective (meth) acrylate, its uses and the like, it may be desired that methyl(meth)acrylate which is used as a raw material is not contained in the (meth)acrylate. In contrast, the process for preparing a (meth)acrylate according to the present invention can prevent the inclusion of methyl(meth)acrylate which is a raw material into the (meth)acrylate. Therefore, the process for preparing a (meth)acrylate is useful as a process for preventing the inclusion of methyl (meth)acrylate into an objective (meth)acrylate.

[Seventh Invention]

The seventh invention is described below.

The process for preparing a (meth)acrylate of the seventh present invention is a process for preparing a (meth)acrylate by a transesterification reaction, in which methyl(meth) acrylate is used as a raw material, characterized in that isohexane and cyclohexane are used in combination as a reaction solvent when the transesterification reaction of methyl(meth)acrylate and an alcohol is carried out.

As described above, one of great characteristics of the present invention resides in that isohexane and cyclohexane are used in combination as a reaction solvent when the transesterification reaction of methyl (meth)acrylate and an alcohol is carried out. When isohexane and cyclohexane are used in combination as a reaction solvent, the transesterification reaction of methyl(meth)acrylate and an alcohol is carried out by using, for example, a reactor equipped with a distillation column, and vapor which is discharged from the overhead of the distillation column is condensed, to separate the resulting condensate into two layers of an upper layer and a lower layer. The separated upper layer mainly contains isohexane and a small amount of methyl alcohol. The lower layer mainly contains methyl alcohol and isohexane.

Since the above-mentioned upper layer mainly contains isohexane and a small amount of methyl alcohol, the upper layer is separated from the condensate, and transferred to the reaction system of the transesterification reaction of methyl (meth)acrylate and an alcohol. Thereby, methyl(meth)acrylate can be efficiently reused.

On the other hand, the above-mentioned lower layer unexpectedly contains little methyl(meth)acrylate, and moreover contains little cyclohexane. Since the lower layer contains little methyl (meth)acrylate as mentioned above, the lower layer can be collected without an operation for transferring to the reaction system of the transesterification reaction of methyl(meth)acrylate and an alcohol. Moreover, methyl alcohol having a high purity can be taken out from the lower layer by, for example, distilling the collected lower layer. The isohexane from which methyl alcohol is removed can be reused as a reaction solvent when the transesterification reaction of methyl(meth)acrylate and an alcohol is carried out. In addition, the separated methyl alcohol can be effectively used, for example, as a raw material for preparing a compound such as methyl(meth)acrylate, a solvent, a fuel and the like.

According to the process for preparing a (meth)acrylate of the present invention, since methyl(meth)acrylate which is used as a raw material can be effectively used, and moreover, isohexane which is used as a reaction solvent can be efficiently collected and reused as a reaction solvent. Also, according to the process for preparing a (meth)acrylate, the resulting by-product is approximately only methyl alcohol, and the methyl alcohol can be effectively used as a raw material for preparing a compound such as methyl(meth) acrylate, a solvent, a fuel and the like, as mentioned above.

Therefore, according to the present invention, methyl (meth)acrylate which is used as a raw material and a reaction solvent can be effectively used, and moreover, it is possible to prevent methyl (meth)acrylate which is used as a raw material from discharging from the reaction system. Furthermore, a by-product other than methyl (meth)acrylate is hardly generated. Accordingly, the process for preparing a (meth)acrylate of the present invention is friendly to global environment, and has a hopeful high industrial applicability.

The alcohol which is used in the transesterification reaction of methyl(meth)acrylate and an alcohol is appropriately selected in accordance with an objective (meth)acrylate. More specifically, the alcohol is appropriately selected in accordance with the ester group of an objective (meth) acrylate.

The alcohol includes, for example, an aliphatic or alicyclic alcohol represented by the formula (VII):

[Chem. 12]

$$R^{10}OH \qquad (VII)$$

wherein $R^{10}$ is an alkyl group having 2 to 30 carbon atoms, which may have a ring structure, such as ethyl alcohol, n-propyl alcohol, isopropyl alcohol, n-butyl alcohol, isobutyl alcohol, sec-butyl alcohol, tert-butyl alcohol, n-pentyl alcohol, n-hexyl alcohol, isohexyl alcohol, cyclohexyl alcohol, 3,3,5-trimethylcyclohexyl alcohol, 4-tert-butylcyclohexyl alcohol, n-heptyl alcohol, n-octyl alcohol, isooctyl alcohol, 2-ethylhexyl alcohol, lauryl alcohol, nonyl alcohol, isononyl alcohol and stearyl alcohol; aromatic alcohols such as phenol, benzyl alcohol, 1-phenylethyl alcohol, 2-phenylethyl alcohol and phenoxyethanol; an amino alcohol represented by the formula (VIII):

[Chem. 13]

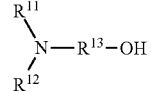
 (VIII)

wherein each of $R^{11}$ and $R^{12}$ is independently hydrogen atom or an alkyl group having 1 to 8 carbon atoms, and $R^{13}$ is an alkylene group having 1 to 4 carbon atoms, such as dimethylaminoethyl alcohol, diethylaminoethyl alcohol, dipropylaminoethyl alcohol, dibutylaminoethyl alcohol, dipentylaminoethyl alcohol, dihexylaminoethyl alcohol, dioctylaminoethyl alcohol, methylethylaminoethyl alcohol, methylpropylaminoethyl alcohol, methylbutylaminoethyl alcohol, methylhexylaminoethyl alcohol, ethylpropylaminoethyl alcohol, ethylbutylaminoethyl alcohol, ethylpentylaminoethyl alcohol, ethyloctylaminoethyl alcohol, propylbutylaminoethyl alcohol, dimethylaminopropyl alcohol, diethylaminopropyl alcohol, dipropylaminopropyl alcohol, dibutylaminopropyl alcohol and butylpentylaminopropyl alcohol; alkoxy alcohols such as methoxyethyl alcohol, ethoxyethyl alcohol and butoxyethyl alcohol; monohydric alcohols such as ally alcohol, metallyl alcohol and tetrahydrofurfuryl alcohol; dihydric alcohols such as ethanediol, propanediol, 1,3-butanediol, 1,4-butanediol and cyclohexanediol; polyhydric alcohols having at least three hydroxyl groups, such as glycerol, and the like, and the present invention is not limited only to those exemplified ones. These alcohols can be used alone, respectively, or at least two kinds thereof can be used in combination, The amount of methyl(meth)acrylate per one equivalent of hydroxyl group of an alcohol is preferably at least 0.3 equivalents, more preferably at least 0.5 equivalents, furthermore preferably at least 0.8 equivalents, from the viewpoint of increase in reaction rate of the transesterification reaction of methyl(meth)acrylate and the alcohol, and preferably at most 5 equivalents, more preferably at most 4 equivalents, furthermore preferably at most 3 equivalents, from the viewpoint of reduce in amount of unreacted methyl (meth)acrylate.

When the transesterification reaction of methyl(meth)acrylate and the alcohol is carried out, a catalyst for transesterification can be used. The catalyst for transesterification includes, for example, metal alkoxides such as sodium alkoxide and titanium alkoxide; tetraalkoxy titaniums such as tetramethoxy titanium, tetraethoxy titanium, tetrapropoxy titanium and tetrabutoxy titanium; dialkyltin oxides such as dialkyltin oxides having an alkyl group of 4 to 18 carbon atoms, such as dibutyltin oxide, dioctyltin oxide and dilauryltin oxide; metal alcoholates such as titanium alcoholate, aluminum alcoholate and magnesium alcoholate, and the like, and the present invention is not limited only to those exemplified ones. These catalysts for transesterification can be used alone respectively, or at least two kinds thereof can be used in combination. Among these catalysts for transesterification, from the viewpoint of acceleration of the transesterification reaction, the tetraalkoxy titanium and the dialkyltin oxide having an alkyl group of 4 to 12 carbon atoms are preferable, the tetraalkoxy titanium and the dialkyltin oxide having an alkyl group of 4 to 8 carbon atoms are more preferable, and tetramethoxy titanium, dibutyltin oxide and dioctyltin oxide are furthermore preferable.

The amount of the catalyst for transesterification is preferably at least 0.00001 moles, more preferably at least 0.0001 moles, from the viewpoint of efficient progress of the transesterification reaction of methyl(meth)acrylate and the alcohol, and preferably at most 0.10 moles, more preferably at most 0.05 moles, from the viewpoint of increase in economic efficiency.

In addition, when the transesterification reaction of methyl (meth)acrylate and the alcohol is carried out, a polymerization inhibitor can be used. As the polymerization inhibitor, there can be exemplified ones which can be used in the first invention. The polymerization inhibitors can be used only in one kind, or at least two kinds thereof can be used in combination.

The amount of the polymerization inhibitor per 100 parts by mass of methyl(meth)acrylate is preferably at least 0.00001 parts by mass, more preferably at least 0.00005 parts by mass, and furthermore preferably at least 0.0001 parts by mass, from the viewpoint of inhibition of polymerization of methyl(meth)acrylate which is used as a raw material and the resulting alkyl acrylate, and is preferably at most 0.1 parts by mass, more preferably at most 0.05 parts by mass, and furthermore preferably at most 0.01 parts by mass, from the viewpoint of enhancement of the purity of the resulting alkyl(meth)acrylate.

In the present invention, as a reaction solvent, isohexane and dicyclohexane are used. Incidentally, the other solvent can be used within a scope which does not hinder an object of the present invention. The other solvent includes, for example, aliphatic hydrocarbon compounds having 5 to 8 carbon atoms other than isohexane and cyclohexane, such as n-pentane, n-hexane, n-heptane, n-octane, 2,3-dimethylbutane, 2,5-dimethylhexane and 2,2,4-trimethylpentane, and the present invention is not limited only to those exemplified ones.

In the present invention, as described above, since isohexane and cyclohexane are used in combination, methyl (meth)acrylate can be efficiently used when a (meth)acrylate is prepared by the transesterification reaction of methyl (meth)acrylate and the alcohol.

The mass ratio of isohexane to cyclohexane cannot be absolutely determined because the mass ratio differs depending on the scale of a reactor, the volume of a distillation column and the like. The mass ratio of isohexane to cyclohexane (isohexane/cyclohexane) is preferably 10/90 to 70/30, more preferably 15/85 to 60/40, from the viewpoint of efficient progress of the transesterification reaction of methyl(meth)acrylate and the alcohol.

The amount of the reaction solvent is not particularly limited, and usually can be 5 to 200 parts by mass per 100 parts by mass of the total amount of methyl(meth)acrylate and the alcohol.

When a reactor such as a reactor having a distillation column is used in the transesterification reaction of methyl (meth)acrylate and the alcohol, isohexane and cyclohexane can be fractionated in the reactor.

The vapor discharged from the overhead of the distillation column is condensed, to separate into two layers of an upper layer and a lower layer. The separated upper layer mainly contains isohexane. The lower layer mainly contains methyl alcohol and isohexane, and contains little cyclohexane and a (meth)acrylate. In order to separate the condensate into an upper layer and a lower layer, the condensate can be cooled. The cooling temperature of the condensate is preferably 0 to 30° C., more preferably 0 to 25° C., furthermore preferably 0 to 20° C., from the viewpoint of efficient separation of the condensate into two layers of an upper layer and a lower layer.

In the condensate which is separated into two layers, the upper layer of which mainly contains methyl alcohol in a small amount other than isohexane. The isohexane contained in this upper layer is used as a reaction solvent in the present invention, and methyl alcohol is a by-product. From the viewpoint of effective use of isohexane, it is preferred that the above-mentioned upper layer is refluxed to a distillation column. When the above-mentioned upper layer is refluxed to a distillation column, it is preferred that the upper layer is refluxed to the distillation column at the middle position thereof from the viewpoint of efficient acceleration of the transesterification reaction of methyl(meth)acrylate and the alcohol.

In the condensate which is separated into two layers, the lower layer mainly contains methyl alcohol which is generated as a by-product. The lower layer substantially contains methyl alcohol, and also contains isohexane and a small amount of cyclohexane. The lower layer can be effectively used substantially as methyl alcohol by, for example, distillation for purification.

In addition, isohexane has a boiling point of about 62° C. at the atmospheric temperature. Therefore, when isohexane is used solely as a reaction solvent, the reaction temperature in the reaction system is lowered. To the contrary, according to the present invention, since cyclohexane which has a boiling point of about 81° C. at the atmospheric temperature is used as a reaction solvent, the reaction temperature can be controlled to not lower than 70° C. Therefore, the transesterification reaction of methyl (meth)acrylate and the alcohol can be efficiently carried out.

When the transesterification reaction of methyl(meth) acrylate and the alcohol is carried out, the reaction temperature is preferably at lowest 70° C., more preferably at lowest 75° C., from the viewpoint of increase in reaction rate, and preferably at highest 140° C., more preferably at highest 130° C., furthermore preferably at highest 120° C., from the viewpoint of inhibition of the polymerization of methyl (meth)acrylate which is used as a raw material and the resulting (meth)acrylate.

When the transesterification reaction of the methyl (meth) acrylate and an alcohol is carried out, the atmosphere is preferably an atmosphere which contains oxygen from the viewpoint of prevention of the polymerization of methyl (meth)acrylate which is used as a raw material and the resulting (meth)acrylate, and more preferably a gas having an oxygen concentration of 5% by volume to an atmospheric concentration from the viewpoint of increase in safety. Also, the pressure of the atmosphere is usually atmospheric pressure, and can be increased or reduced. For example, when the pressure of the atmosphere is reduced, there is an advantage such that a side-reaction can be restrained, because the reflux temperature can be lowered.

When the transesterification reaction of methyl(meth) acrylate and the alcohol is carried out, the reaction time cannot be absolutely determined because the reaction time differs depending on the reaction temperature and the like. Therefore, the reaction time is usually controlled so that the reaction ratio is attained to an intended value. The end point of the transesterification reaction of methyl(meth)acrylate and the alcohol can be confirmed by, for example, gas chromatography, liquid chromatography and the like.

The transesterification reaction of methyl(meth)acrylate and the alcohol can be carried out by using, for example, a fractionator, a fluidized bed, a fixed bed, a reaction distillation column and the like, and the present invention is not limited only to those exemplified ones. In addition, the transesterification reaction of methyl(meth)acrylate and the alcohol can be carried out by any of a circulation type and a batch type.

In the present invention, when the transesterification reaction of methyl(meth)acrylate and an alcohol is carried out, it is preferred that a reactor equipped with a distillation column is used as a reactor. A reactor equipped with a distillation column includes, for example, a so-called reaction tank which is a reactor equipped with a distillation column at the upper portion of the reactor and a distillation still can be used, and the present invention is not limited only to those exemplified ones. There is no limitation in the structure and type of the distillation column. Among the distillation columns, one having high gas-liquid contact efficiency is preferable. The preferred distillation column includes, for example, a packed-column type distillation column, a tray type distillation column and the like. The theoretical plate number of the distillation column is preferably at least 7, more preferably at least 10, furthermore preferably at least 15, from the viewpoint of efficient and stable progress of the transesterification reaction of methyl (meth)acrylate and the alcohol, and preferably at most 100, more preferably at most 70, furthermore preferably at most 50, from the viewpoint of increase in economic efficiency.

In the course of the progress of the transesterification reaction of methyl(meth)acrylate and the alcohol, methyl alcohol is generated as a by-product. It is usually preferred that the methyl alcohol generated as a by-product is removed from the reaction system in order to promote the reaction. The methyl alcohol generated as a by-product can be removed from the reaction system by, for example, forming an azeotropic mixture together with isohexane as mentioned above. The methyl alcohol can be effectively used as a raw material for preparing a compound such as methyl (meth) acrylate, a solvent, a fuel and the like.

The transesterification reaction of methyl(meth)acrylate and the alcohol can be efficiently carried out by, for example, charging a reactor with methyl(meth)acrylate, an alcohol, isohexane and cyclohexane, as occasion demands, a catalyst for transesterification and a polymerization inhibitor, and heating the components in the reactor, to reflux them.

When a reactor equipped with a distillation column is used as a reactor, it is preferred that vapor is taken out from the reactor at the overhead of the reactor, and the condensate of the vapor is separated into two layers by using a separator such as a decanter or a separating funnel. Incidentally, a part of the above-mentioned condensate can be refluxed to the distillation column. It is preferred that the temperature at the overhead of distillation column is controlled to 40 to 50° C. in order to efficiently form an azeotropic mixture of isohexane and methyl alcohol.

In the separated two layers, since the upper layer substantially contains isohexane, it is preferred that the upper layer is refluxed to the distillation column, for example, at the middle position of the distillation column. Also, since the lower layer substantially contains methyl alcohol, it is preferred that the lower layer is collected without transferring to the distillation column.

After the transesterification reaction of methyl(meth)acrylate and the alcohol is carried out, a (meth)acrylate which is an objective compound can be collected by distilling away isohexane and cyclohexane which are organic solvents used in the reaction, unreacted methyl (meth)acrylate and an alcohol from the resulting reaction mixture. The removal of unreacted methyl(meth)acrylate and the alcohol can be carried out by means of, for example, distillation, extraction and the like.

As explained above, according to the present invention, since isohexane and cyclohexane are used as a reaction solvent when the transesterification reaction of methyl (meth)acrylate and the alcohol is carried out, methyl(meth) acrylate can be efficiently used.

EXAMPLES

Next, the present invention will be more specifically explained based on working examples, and the present invention is not limited only to those working examples.

Example I of the First Invention

Example I-1

To a 2 L four-necked glass flask were attached a 20-stage Oldershaw, a reflux condenser and a gas introduction tube, and the flask was charged with 675 g (7.5 moles) of 1,4-butanediol, 430 g (5.0 moles) of methyl acrylate, 101.39 g of cyclohexane and 0.72 g of phenothiazine as a polymerization inhibitor. Thereafter, 3.6 g of dioctyltin oxide was added to the flask. While a nitrogen gas containing 7% by volume of oxygen gas was blown into the flask at a flow rate of 20 mL/min, the reaction of 1,4-butanediol and methyl acrylate was carried out at a temperature of 85° C. for 10 hours.

After the azeotropic mixture of the generated methanol and cyclohexane was put in a decanter, and 50 mL of water was continuously added to the decanter. While a separated aqueous methanol solution was removed from the decanter, the reaction of 1,4-butanediol and methyl acrylate was carried out at a temperature of 85° C. until almost no methanol was distilled out.

After the completion of the reaction of 1,4-butanediol and methyl acrylate, the obtained reaction liquid was heated to 88° C., and unreacted methyl acrylate was removed by azeotropic distillation with cyclohexane, to obtain 1109 g of a reaction mixture.

The obtained reaction mixture in an amount of 1109 g was supplied at a flow rate of 50 mL/h and pure water was also supplied at a flow rate of 29.5 mL/h to the upper part of a pulsating type continuous extraction tower (filled tower with 25 mm diameter and 1.4 m length) for continuous extraction (first extraction), cyclohexane was supplied at a flow rate of 87.7 mL/h to the lower part of the continuous extraction tower, the inside of the tower was heated to 20 to 25° C., and extraction was carried out continuously to obtain a cyclohexane layer containing 1,4-butanediol diacrylate as a by-product and a water layer containing the resulting 4-hydroxybutyl acrylate and unreacted 1,4-butanediol. Incidentally, No insoluble matter was found in the cyclohexane layer and in the water layer.

For continuous extraction (second extraction), 1200 mL of the obtained water layer was supplied at a flow rate of 50 mL/h to the upper part of the continuous extraction tower and toluene as an extraction solvent was supplied over 24 hours at a flow rate of 87.5 mL/h to the lower part of the continuous extraction tower. The inside of the tower was heated to 35 to 40° C., and the continuous extraction was carried out, to obtain a toluene layer containing 4-hydroxybutyl acrylate, and a water layer containing 1,4-butanediol. When the components other than toluene contained in the toluene layer were analyzed by gas chromatography, the components were found to contain 97.68% by mass of 4-hydroxybutyl acrylate, 2.01% by mass of 1,4-butanediol and 0.11% by mass of 1,4-butanediol diacrylate.

From the above-mentioned results, it was found that 4-hydroxybutyl acrylate can be prepared in a high yield by using dioctyltin oxide as a catalyst for transesterification.

Example I-2

To a 2 L four-necked glass flask were attached a 20-stage Oldershaw, a reflux condenser and a gas introduction tube, and the flask was charged with 675 g (7.5 moles) of 1,4-butanediol, 430 g (5.0 moles) of methyl acrylate, 67.59 g of cyclohexane, and 3.60 g of phenothiazine as a polymerization inhibitor. Thereafter, 4.73 g of dilauryltin oxide was added to the flask. While a nitrogen gas containing 7% by volume of oxygen gas was blown into the flask, the reaction of 1,4-butanediol and methyl acrylate was carried out at 85° C. for 10 hours.

After the azeotropic mixture of the resulting methanol and cyclohexane was put in a decanter, and 50 mL of water was continuously added to the decanter. While a separated aqueous methanol solution was removed from the decanter, the reaction of 1,4-butanediol and methyl acrylate was carried out at a temperature of 85° C. until almost no methanol was distilled out.

After the completion of the reaction of 1,4-butanediol and methyl acrylate, the obtained reaction liquid was heated to 88° C. and unreacted methyl acrylate was removed by azeotropic distillation with cyclohexane, to obtain 1156 g of a reaction mixture.

The obtained reaction mixture in an amount of 1128 g was supplied at a flow rate of 50 mL/h and pure water was also supplied at a flow rate of 29.5 mL/h to the upper part of a pulsating type continuous extraction tower for continuous extraction (first extraction), cyclohexane was supplied over 24 hours at a flow rate of 89.8 mL/h to the lower part of the continuous extraction tower, the inside of the tower was heated to 30 to 35° C., and extraction was carried out continuously to obtain a cyclohexane layer containing 1,4-butanediol diacrylate as a by-product and a water layer containing the resulting 4-hydroxybutyl acrylate and unreacted 1,4-butanediol.

For continuous extraction (second extraction), 1230 mL of the obtained water layer was supplied at a flow rate of 50 mL/h to the upper part of the continuous extraction tower and toluene as an extraction solvent was supplied over 24 hours at a flow rate of 87.5 mL/h to the lower part of the continuous extraction tower. The inside of the tower was heated to 35 to 40° C., and the continuous extraction was carried out, to obtain a toluene layer containing 4-hydroxybutyl acrylate, and a water layer containing 1,4-butanediol. When the content of 1,4-butanediol diacrylate in the components other than toluene contained in the toluene layer was analyzed by gas chromatography, the content was found to be 0.12% by mass.

From the above-mentioned results, it was found that 4-hydroxybutyl acrylate can be prepared in a high yield by using dilauryltin oxide as a catalyst for transesterification, and it was also found that even if 4-hydroxybutyl acrylate was concentrated by heating, 1,4-butanediol was scarcely generated.

Example I-3

To a 2 L four-necked glass flask were attached a 20-stage Oldershaw, a reflux condenser and a gas introduction tube, and the flask was charged with 675 g (7.5 moles) of 1,4-butanediol, 430 g (5.0 moles) of methyl acrylate, 67.59 g of cyclohexane, and 3.60 g of phenothiazine as a polymerization inhibitor. Thereafter, 2.49 g of dibutyltin oxide was added to the flask. While air was blown into the flask, the reaction of 1,4-butanediol and methyl acrylate was carried out at 85° C.

After the azeotropic mixture of the resulting methanol and cyclohexane was put in a decanter, and 50 mL of water was continuously added to the decanter. While a separated aqueous methanol solution was removed from the decanter, the reaction of 1,4-butanediol and methyl acrylate was carried out at a temperature of 85° C. until almost no methanol was distilled out.

After the completion of the reaction of 1,4-butanediol and methyl acrylate, the obtained reaction liquid was heated to 88° C., and unreacted methyl acrylate was removed by azeotropic distillation with cyclohexane, to obtain 1138 g of a reaction mixture.

The obtained reaction mixture in an amount of 1115 g was supplied at a flow rate of 50 mL/h and pure water was also supplied at a flow rate of 29.5 mL/h to the upper part of a pulsating type continuous extraction tower for continuous extraction (first extraction), cyclohexane was supplied over 24 hours at a flow rate of 89.8 mL/h to the lower part of the continuous extraction tower, the inside of the tower was heated to 30 to 35° C., and extraction was carried out continuously to obtain a cyclohexane layer containing 1,4-butanediol diacrylate as a by-product and a water layer containing the resulting 4-hydroxybutyl acrylate and unreacted 1,4-butanediol.

For continuous extraction (second extraction), 1210 mL of the obtained water layer was supplied at a flow rate of 50 mL/h to the upper part of the continuous extraction tower and toluene as an extraction solvent was supplied over 24 hours at a flow rate of 87.5 mL/h to the lower part of the continuous extraction tower. The inside of the tower was heated to 35 to 40° C., and the continuous extraction was carried out, to obtain a toluene layer containing 4-hydroxybutyl acrylate, and a water layer containing 1,4-butanediol. When the content of 1,4-butanediol diacrylate in the components other than toluene contained in the toluene layer was analyzed by gas chromatography, the content was found to be 0.11% by mass.

Example I-4

The same procedure as in Example I-1 was carried out except that 2.36 g of dioctyltin oxide (water content: not more than 1000 ppm) collected in Example I-1 was used in place of 2.36 g of dioctyltin oxide. The obtained reaction liquid was analyzed by gas chromatography after 10 hours passed from the starting of the reaction. As a result, the content of 4-hydroxybutyl acrylate in the three components of 4-hydroxybutyl acrylate, 1,4-butanediol and 1,4-butanediol diacrylate was 53.5% by mass.

Example I-5

The same procedure as in Example I-4 was carried out except that 2.36 g of dioctyltin oxide (water content: not more than 1000 ppm) collected in Example I-4 was used in place of 2.36 g of dioctyltin oxide. The obtained reaction liquid was analyzed by gas chromatography after 10 hours passed from the starting of the reaction. As a result, the content of 4-hydroxybutyl acrylate in the three components of 4-hydroxybutyl acrylate, 1,4-butanediol and 1,4-butanediol diacrylate was 52.8% by mass.

Example I-6

The same procedure as in Example I-5 was carried out except that 2.36 g of dioctyltin oxide (water content: not more than 1000 ppm) collected in Example I-5 was used in place of 2.36 g of dioctyltin oxide. The obtained reaction liquid was analyzed by gas chromatography after 10 hours passed from the starting of the reaction. As a result, the content of 4-hydroxybutyl acrylate in the three components of 4-hydroxybutyl acrylate, 1,4-butanediol and 1,4-butanediol diacrylate was 54.3% by mass.

Example I-7

The same procedure as in Example I-6 was carried out except that 2.36 g of dioctyltin oxide (water content: not more than 1000 ppm) collected in Example I-6 was used in place of 2.36 g of dioctyltin oxide in Example I-6. The obtained reaction liquid was analyzed by gas chromatography after 10 hours passed from the starting of the reaction. As a result, the content of 4-hydroxybutyl acrylate in the three components of 4-hydroxybutyl acrylate, 1,4-butanediol and 1,4-butanediol diacrylate was 52.5% by mass.

Example I-8

The same procedure as in Example I-7 was carried out except that 2.36 g of dioctyltin oxide (water content: not more than 1000 ppm) collected in Example I-7 was used in place of 2.36 g of dioctyltin oxide. The obtained reaction liquid was analyzed by gas chromatography after 10 hours passed from the starting of the reaction. As a result, the content of 4-hydroxybutyl acrylate in the three components of 4-hydroxybutyl acrylate, 1,4-butanediol and 1,4-butanediol diacrylate was 52.6% by mass.

Example I-9

The same procedure as in Example I-8 was carried out except that 2.36 g of dioctyltin oxide (water content: not more than 1000 ppm) collected in Example I-8 was used in place of 2.36 g of dioctyltin oxide in Example I-8. The obtained reaction liquid was analyzed by gas chromatography after 10 hours passed from the starting of the reaction. As a result, the content of 4-hydroxybutyl acrylate in the three components of 4-hydroxybutyl acrylate, 1,4-butanediol and 1,4-butanediol diacrylate was 52.8% by mass.

Example I-10

The same procedure as in Example I-9 was carried out except that 2.36 g of dioctyltin oxide (water content: not more than 1000 ppm) collected in Example I-9 was used in place of 2.36 g of dioctyltin oxide. The obtained reaction liquid was analyzed by gas chromatography after 10 hours passed from the starting of the reaction. As a result, the content of 4-hydroxybutyl acrylate in the three components of 4-hydroxybutyl acrylate, 1,4-butanediol and 1,4-butanediol diacrylate was 53.8% by mass.

Example I-11

The same procedure as in Example I-10 was carried out except that 2.36 g of dioctyltin oxide (water content: not more than 1000 ppm) collected in Example I-10 was used in place of 2.36 g of dioctyltin oxide in Example I-10. The reaction liquid was analyzed by gas chromatography after 10 hours passed from the starting of the reaction. As a result, the content of 4-hydroxybutyl acrylate in the three components of 4-hydroxybutyl acrylate, 1,4-butanediol and 1,4-butanediol diacrylate was 53.0% by mass.

Example I-12

The same procedure as in Example I-11 was carried out except that 2.36 g of dioctyltin oxide (water content: not more than 1000 ppm) collected in Example I-11 was used in place of 2.36 g of dioctyltin oxide in Example I-11. The reaction liquid was analyzed by gas chromatography after 10 hours passed from the starting of the reaction. As a result, the content of 4-hydroxybutyl acrylate in the three components of 4-hydroxybutyl acrylate, 1,4-butanediol and 1,4-butanediol diacrylate was 52.1% by mass.

From the results of Examples I-4 to I-12, it can be understood that a dialkyltin oxide having an alkyl group of 4 to 18 carbon atoms used in the transesterification reaction of 1,4-butanediol and an acrylic acid alkyl ester can be reused, since the dialkyltin oxide retains its catalytic activity, even if the dialkyltin oxide is collected after the transesterification reaction of 1,4-butanediol and an acrylic acid alkyl ester, and repeatedly used as a catalyst for transesterification in the transesterification reaction of 1,4-butanediol and an acrylic acid alkyl ester.

Accordingly, the process for preparing 4-hydroxybutyl acrylate of the present invention is advantageous in terms of effective utilization of the catalyst since the alkyltin oxide having an alkyl group of 4 to 18 carbon atoms can be used repeatedly as a catalyst for transesterification in the transesterification reaction of 1,4-butanediol and an acrylic acid alkyl ester.

Example I-13

In order to examine the effect of water on a dialkyltin oxide in Example I-1, the same procedure as in Example I-1 was carried out except that 9 g of dioctyltin oxide and 6 g of water (water content in the reaction system: 0.5% by mass) were added. The period of time necessary for attaining the content of 4-hydroxybutyl acrylate in three components of 4-hydroxybutyl acrylate, 1,4-butanediol and 1,4-butanediol diacrylate to 48% by mass was measured by gas chromatography. As a result, the period of time was 9 hours.

Example I-14

In order to examine the effect of water on a dialkyltin oxide in Example I-1, the same procedure as in Example I-1 was carried out except that 9 g of dioctyltin oxide and 12 g of water (water content in the reaction system: 1.0% by mass) were added. The period of time necessary for attaining the content of 4-hydroxybutyl acrylate in three components of 4-hydroxybutyl acrylate, 1,4-butanediol and 1,4-butanediol diacrylate to 48% by mass was measured by gas chromatography. As a result, the period of time was 10.5 hours.

Example I-15

In order to examine the effect of water on a dialkyltin oxide in Example I-1, the same procedure as in Example I-1 was carried out except that 9 g of dioctyltin oxide and 24 g of water (water content in the reaction system: 2.0% by mass) were added. The period of time necessary for attaining the content of 4-hydroxybutyl acrylate in three components of 4-hydroxybutyl acrylate, 1,4-butanediol and 1,4-butanediol diacrylate to 48% by mass was measured by gas chromatography. As a result, the period of time was 12.5 hours.

Example I-16

In order to examine the effect of water on a dialkyltin oxide in Example I-1, the same procedure as in Example I-1 was carried out except that 9 g of dioctyltin oxide and 36 g of water (water content in the reaction system: 3.0% by mass) were added. The period of time necessary for attaining the content of 4-hydroxybutyl acrylate in three components of 4-hydroxybutyl acrylate, 1,4-butanediol and 1,4-butanediol diacrylate to 48% by mass was measured by gas chromatography. As a result, the period of time was 15 hours.

Example I-17

In order to examine the effect of water on a dialkyltin oxide in Example I-1, the same procedure as in Example I-1 was carried out except that 9 g of dioctyltin oxide and 1.2 g of water (water content in the reaction system: 0.1% by mass) were added. The period of time necessary for attaining the content of 4-hydroxybutyl acrylate in three components of 4-hydroxybutyl acrylate, 1,4-butanediol and 1,4-butanediol diacrylate to 48% by mass was measured by gas chromatography. As a result, the period of time was 7 hours.

From the results of Examples I-13 to I-17, it can be understood that when water exists in the case where the transesterification reaction of 1,4-butanediol and an acrylic acid alkyl ester is carried out in the presence of a dialkyltin oxide, the transesterification reaction of 1,4-butanediol and an acrylic acid alkyl ester is hindered. Therefore, the water content in the reaction system of the transesterification reaction of 1,4-butanediol and an acrylic acid alkyl ester is preferably 0.5% by mass or lower, and more preferably 0.1% by mass (1000 ppm) or lower.

Example I-18

In order to examine the effect of amount of the catalyst for transesterification in Example I-1, the same procedure as in Example I-1 was carried out except that the amount of dioctyltin oxide was changed to 0.18 g. As a result, it took 40 hours, to give 4-hydroxybutyl acrylate in the same amount as that of 4-hydroxybutyl acrylate obtained in Example I-1.

From the above-mentioned results, it can be understood that according to the process for preparing 4-hydroxybutyl acrylate of the present invention, 4-hydroxybutyl acrylate can be efficiently prepared by the transesterification reaction of 1,4-butanediol and an acrylic acid alkyl ester, and that the catalyst for transesterification used in the transesterification reaction can be efficiently collected.

Example II of the Second Invention

Example II-1

To a 2 L four-necked glass flask were attached a 20-stage Oldershaw, a reflux condenser and a gas introduction tube, and the flask was charged with 675 g (7.5 moles) of 1,4-butanediol, 500.6 g (5.0 moles) of methyl methacrylate, 101.39 g of cyclohexane and 0.72 g of phenothiazine as a polymerization inhibitor. Thereafter, 0.563 g (0.0025 moles) of sodium diethyldithiocarbamate was added to the flask. While a nitrogen gas containing 7% by volume of oxygen gas was blown into the flask at a flow rate of 20 mL/min, the reaction of 1,4-butanediol and methyl methacrylate was carried out at 87° C. for 5 hours.

After the azeotropic mixture of the resulting methanol and cyclohexane was put in a decanter, and 50 mL of water was continuously added to the decanter. While a separated aqueous methanol solution was removed from the decanter, the reaction of 1,4-butanediol and methyl methacrylate was carried out at a temperature of 87° C. until almost no methanol was distilled out.

After the completion of the reaction of 1,4-butanediol and methyl methacrylate, the obtained reaction liquid was heated to 80° C. under reduced pressure, and cyclohexane and unreacted methyl methacrylate were removed by distillation to obtain 1015 g of a reaction mixture.

The components other than the solvent contained in the obtained reaction mixture were analyzed by gas chromatography. As a result, the components were found to contain 49.65% by mass of 4-hydroxybutyl methacrylate, 37.37% by mass of 1,4-butanediol and 12.45% by mass of 1,4-butanediol dimethacrylate.

From the above-mentioned results, it was found that 4-hydroxybutyl methacrylate can be efficiently prepared by using sodium diethyldithiocarbamate as a catalyst for transesterification.

Example II-2

To a 2 L four-necked glass flask were attached a 20-stage Oldershaw, a reflux condenser and a gas introduction tube, and the flask was charged with 675 g (7.5 moles) of 1,4-butanediol, 500.6 g (5.0 moles) of methyl methacrylate, 101.39 g of cyclohexane and 0.72 g of phenothiazine as a polymerization inhibitor. Thereafter, 0.500 g (0.0025 moles) of potassium diethyldithiocarbamate was added to the flask. While a nitrogen gas containing 7% by volume of oxygen gas was blown into the flask at a flow rate of 20 mL/min, the reaction of 1,4-butanediol and methyl methacrylate was carried out at 85° C. for 10 hours.

The azeotropic mixture of the resulting methanol and cyclohexane was put in a decanter, and 50 mL of water was continuously added to the decanter. While a separated aqueous methanol solution was removed from the decanter, the reaction of 1,4-butanediol and methyl methacrylate was carried out at a temperature of 85° C. until almost no methanol was distilled out.

After the completion of the reaction of 1,4-butanediol and methyl methacrylate, the obtained reaction liquid was heated to 80° C. under reduced pressure, and cyclohexane and unreacted methyl methacrylate were removed by distillation, to obtain 1010 g of a reaction mixture.

The components other than the solvent contained in the obtained reaction mixture were analyzed by gas chromatography. As a result, the components were found to contain 49.15% by mass of 4-hydroxybutyl methacrylate, 38.37% by mass of 1,4-butanediol and 11.95% by mass of 1,4-butanediol dimethacrylate.

From the above-mentioned results, it was found that 4-hydroxybutyl methacrylate can be efficiently prepared by using potassium diethyldithiocarbamate as a catalyst for transesterification.

Example II-3

A 3 L separatory funnel was charged with 1000 g of the reaction mixture obtained in Example II-1 and 500 g of cyclohexane, the ingredients were stirred. The resulting mixture was washed with 500 g of pure water and allowed to stand to separate into 1064 g of a cyclohexane layer and 934 g of a water layer.

Next, as a first extraction operation, pure water was supplied at a flow rate of 50 mL/h to the upper part of a pulsating type continuous extraction tower (filled tower with 25 mm diameter and 1.4 m length), and 1064 g of the cyclohexane layer was supplied over 20 hours at a flow rate of 50 mL/h to the lower part of the continuous extraction tower The inside of the tower was heated to 30 to 35° C., and extraction was carried out continuously, to obtain a cyclohexane layer containing 1,4-butanediol dimethacrylate as a by-product, and a water layer containing the resulting 4-hydroxybutyl methacrylate and unreacted 1,4-butanediol. No insoluble matter was found in the cyclohexane layer and in the water layer.

As a second extraction operation, 1200 mL of a mixture obtained by mixing the obtained water layer and the water layer obtained by the first extraction operation was supplied at a flow rate of 50 mL/h to the upper part of the continuous extraction tower and toluene as an extraction solvent was supplied over 24 hours at a flow rate of 87.5 mL/h to the lower part of the continuous extraction tower. The inside of the tower was heated to 35 to 40° C., and the continuous extraction was carried out, to obtain a toluene layer containing 4-hydroxybutyl methacrylate, and a water layer containing 1,4-butanediol.

The components other than toluene contained in the toluene layer were analyzed by gas chromatography, it was found that 0.08% by mass of 1,4-butanediol dimethacrylate was contained in the components.

Next, A 2 L three-necked glass flask was charged with 1400 g of the toluene layer obtained by the second extraction operation, and 0.008 g of hydroquinone monomethyl ether as a polymerization inhibitor was added to the flask. The temperature in the bottom part of the flask was adjusted to 74 to 85° C., and toluene was removed under reduced pressure of 280 to 20 hPa by distillation for 14 hours, to concentrate 4-hydroxybutyl methacrylate.

The components contained in the condensed material were analyzed by gas chromatography. As a result, the components were found to contain 98.57% by mass of 4-hydroxybutyl methacrylate, 0.09% by mass of 1,4-butanediol dimethacrylate and 1.08% by mass of 1,4-butanediol.

From the above-mentioned results, it was found that 4-hydroxybutyl methacrylate can be efficiently collected by carrying out the extraction operation using sodium diethyldithiocarbamate as a catalyst for transesterification.

Example II-4

To a 2 L four-necked glass flask were attached a 20-stage Oldershaw, a reflux condenser and a gas introduction tube, and the flask was charged with 675 g (7.5 moles) of 1,4-butanediol, 430 g (5.0 moles) of methyl acrylate, 101.39 g of cyclohexane and 0.72 g of phenothiazine as a polymerization inhibitor. Thereafter, 0.563 g (0.0025 moles) of sodium diethyldithiocarbamate was added to the flask. While a nitrogen gas containing 7% by volume of oxygen gas was blown into the flask at a flow rate of 20 mL/min, the reaction of 1,4-butanediol and methyl acrylate was carried out at 85° C. for 5 hours.

After the azeotropic mixture of the resulting methanol and cyclohexane was put in a decanter, and 50 mL of water was continuously added to the decanter. While a separated aqueous methanol solution was removed from the decanter, the reaction of 1,4-butanediol and methyl acrylate was carried out at a temperature of 85° C. until almost no methanol was distilled out.

After the completion of the reaction of 1,4-butanediol and methyl acrylate, the obtained reaction liquid was heated to 88° C., and unreacted methyl acrylate was removed by azeotropic distillation with cyclohexane, to obtain 1109 g of a reaction mixture.

The components other than the solvent contained in the obtained reaction mixture were analyzed by gas chromatography. As a result, the components were found to contain 39.25% by mass of 4-hydroxybutyl acrylate, 52.37% by mass of 1,4-butanediol and 7.35% by mass of 1,4-butanediol diacrylate.

From the above-mentioned results, it was found that 4-hydroxybutyl acrylate can be efficiently prepared by using sodium diethyldithiocarbamate as a catalyst for transesterification.

Next, as a first extraction operation, the obtained reaction mixture in an amount of 1088 g was supplied at a flow rate of 50 mL/h and pure water was also supplied at a flow rate of 29.5 mL/h to the upper part of a pulsating type continuous extraction tower (filled tower with 25 mm diameter and 1.4 m length), cyclohexane was supplied over 22 hours at a flow rate of 87.8 mL/h to the lower part of the continuous extraction tower. The inside of the tower was heated to 30 to 35° C., and extraction was carried out continuously to obtain a cyclohexane layer containing 1,4-butanediol diacrylate as a by-product, and a water layer containing the resulting 4-hydroxybutyl acrylate and unreacted 1,4-butanediol.

As a second extraction operation, 1200 mL of the obtained water layer was supplied at a flow rate of 50 mL/h to the upper part of the continuous extraction tower, and toluene as an extraction solvent was supplied over 24 hours at a flow rate of 87.5 mL/h to the lower part of the continuous extraction tower. The inside of the tower was heated to 35 to 40° C., and the continuous extraction was carried out, to obtain a toluene layer containing 4-hydroxybutyl acrylate, and a water layer containing 1,4-butanediol. The content of 1,4-butanediol diacrylate in the components other than toluene contained in the toluene layer was analyzed by gas chromatography. As a result, the content was found to be 0.11% by mass.

Next, a 2 L three-necked glass flask was charged with 1400 g of the toluene layer obtained by the second extraction operation, and 0.008 g of hydroquinone monomethyl ether as a polymerization inhibitor was added to the flask. The temperature in the bottom part of the flask was adjusted to 74 to 85° C., and toluene was removed under reduced pressure of 280 to 20 hPa by distillation for 14 hours to concentrate 4-hydroxybutyl acrylate.

The components contained in the condensed material were analyzed by gas chromatography. As a result, the components were found to contain 97.75% by mass of 4-hydroxybutyl methacrylate, 0.14% by mass of 1,4-butanediol diacrylate and 1.98% by mass of 1,4-butanediol.

From the above-mentioned results, it was found that 4-hydroxybutyl acrylate can be efficiently collected by carrying out the extraction operation using sodium diethyldithiocarbamate as a catalyst for transesterification.

Example II-5

First Reuse of Collected Catalyst

The water layer obtained by the second extraction operation in Example II-3 was concentrated, to give 367 g of a mixture of 1,4-butanediol and sodium diethyldithiocarbamate.

Next, 367 g of the mixture collected in the above was used in place of 1,4-butanediol used in Example II-1, and new 1,4-butanediol was used so that the amount of the amount of 1,4-butanediol could be the same as the amount of 1,4-butanediol used in Example II-1. At that time, no catalyst for transesterification was newly added, since sodium diethyldithiocarbamate was contained in the above-mentioned mixture.

Thereafter, the reaction of 1,4-butanediol and methyl methacrylate was carried out at a temperature of 87° C. for 5 hours in the same manner as in Example II-1.

After the completion of the reaction of 1,4-butanediol and methyl methacrylate, the obtained reaction liquid was heated to 80° C. under reduced pressure, and unreacted methyl methacrylate was removed by distillation to obtain 1012 g of a reaction mixture.

The components other than the solvent contained in the obtained reaction mixture were analyzed by gas chromatography. As a result, the components were found to contain 49.35% by mass of 4-hydroxybutyl methacrylate, 37.97% by mass of 1,4-butanediol and 12.32% by mass of 1,4-butanediol dimethacrylate.

A 3 L separatory funnel was charged with 1000 g of the reaction mixture obtained in Example II-5 and 500 g of cyclohexane, and the ingredients were stirred. The resulting mixture was washed with 500 g of pure water, and allowed to stand to separate into 1062 g of a cyclohexane layer and 936 g of a water layer.

Next, as a first extraction operation, pure water was supplied at a flow rate of 50 mL/h to the upper part of a pulsating type continuous extraction tower (filled tower with 25 mm diameter and 1.4 m length), and 1062 g of the cyclohexane layer was supplied over 20 hours at a flow rate of 50 mL/h to the lower part of the continuous extraction tower. The inside of the tower was heated to 30 to 35° C., and extraction was carried out continuously, to obtain a cyclohexane layer containing 1,4-butanediol dimethacrylate as a by-product, and a water layer containing the resulting 4-hydroxybutyl methacrylate and unreacted 1,4-butanediol. No insoluble matter was found in the cyclohexane layer and in the water layer.

As a second extraction operation, 1200 mL of a mixture obtained by mixing the obtained water layer and the water layer obtained by the first extraction operation was supplied at a flow rate of 50 mL/h to the upper part of the continuous extraction tower, and toluene as an extraction solvent was supplied over 24 hours at a flow rate of 87.5 mL/h to the lower part of the continuous extraction tower. The inside of the tower was heated to 35 to 40° C., and the continuous extraction was carried out, to obtain a toluene layer containing 4-hydroxybutyl methacrylate, and a water layer containing 1,4-butanediol and sodium diethyldithiocarbamate.

The components other than toluene contained in the toluene layer were analyzed by gas chromatography. As a result, it was found that 0.08% by mass of 1,4-butanediol dimethacrylate was contained in the components.

Next, a 2 L three-necked glass flask was charged with 1400 g of the toluene layer obtained by the second extraction operation, and 0.008 g of hydroquinone monomethyl ether was added as a polymerization inhibitor to the flask. The temperature in the bottom part of the flask was adjusted to 74 to 85° C., and toluene was removed under reduced pressure of 280 to 20 hPa by distillation for 14 hours, to concentrate 4-hydroxybutyl methacrylate.

The components contained in the concentrate obtained in the above were analyzed by gas chromatography. As a result, 98.42% by mass of 4-hydroxybutyl methacrylate, 0.08% by mass of 1,4-butanediol dimethacrylate and 1.25% by mass of 1,4-butanediol were contained in the components.

From the above-mentioned results, it was found that 4-hydroxybutyl acrylate can be efficiently collected, even when the extraction operation is carried out by using sodium diethyldithiocarbamate as a catalyst for transesterification.

Example II-6

Second Reuse of Collected Catalyst

The water layer obtained by the extraction operation as the second extraction operation in Example II-5 was concentrated, to give 353 g of a mixture of 1,4-butanediol and sodium diethyldithiocarbamate.

Next, the same procedure as in Example II-1 was carried out except that 353 g of the mixture collected in the above was used in place of 1,4-butanediol used in Example II-1, and furthermore new 1,4-butanediol in the same amount as that of 1,4-butanediol which is used in Example II-1 was used. Incidentally, since sodium diethyldithiocarbamate was contained in the mixture, a catalyst for transesterification was not additionally added.

Thereafter, the reaction of 1,4-butanediol and methyl methacrylate was carried out at a temperature of 87° C. for 6 hours in the same manner as in Example II-1.

After the completion of the reaction of 1,4-butanediol and methyl methacrylate, the obtained reaction liquid was heated to 80° C. under reduced pressure, and unreacted methyl methacrylate was removed by distillation, to obtain 1018 g of a reaction mixture.

The components other than the solvent contained in the obtained reaction mixture were analyzed by gas chromatography. As a result, 48.13% by mass of -hydroxybutyl methacrylate, 39.71% by mass of 1,4-butanediol and 11.82% by mass of 1,4-butanediol dimethacrylate were contained in the components.

From the above-mentioned results, it was found that 4-hydroxybutyl acrylate can be efficiently collected even when the extraction operation is carried out by reusing sodium diethyldithiocarbamate twice as a catalyst for transesterification.

Accordingly, it can be understood that the catalyst for transesterification used in the transesterification reaction of 1,4-butanediol and a (meth)acrylic acid alkyl ester in each example retains the catalytic activity even when the catalyst is collected together with unreacted 1,4-butanediol by the extraction operation after the transesterification reaction, and the catalyst is repeatedly reused in the transesterification reaction of 1,4-butanediol and a (meth)acrylic acid alkyl ester.

From the facts mentioned above, it can be understood that the process for preparing 4-hydroxybutyl(meth)acrylate of the present invention is a method excellent in industrial productivity, since the catalyst for transesterification can be used repeatedly and thus the catalyst for transesterification can be used effectively.

Example III of the Third Invention

Example III-1

To a 2 L four-necked glass flask were attached a 20-stage Oldershaw, a reflux condenser, and an air introduction tube, and the flask was charged with 675 g (7.5 moles) of 1,4-butanediol, 430.45 g (5.0 moles) of methyl acrylate, 100 g of cyclohexane and 0.72 g of phenothiazine as a polymerization inhibitor. Thereafter, 3.61 g of dioctyltin oxide was added to the flask. While a nitrogen gas containing 7% by volume of oxygen gas was blown into the flask at a flow rate of 20 mL/min, the reaction of 1,4-butanediol and methyl acrylate was carried out at 85° C. for 10 hours, to obtain a reaction mixture. The components other than the solvent contained in the reaction mixture were analyzed by gas chromatography. As a result, the content of 4-hydroxybutyl acrylate was 50.9% by mass, the content of 1,4-butanediol was 37.9% by mass, and the content of 1,4-butanediol diacrylate was 11.2% by mass.

Next, the azeotropic mixture of the resulting methanol and cyclohexane was put in a decanter, and 50 mL of water was continuously added to the decanter. While a separated aqueous methanol solution was removed from the decanter, the reaction of 1,4-butanediol and methyl acrylate was carried out at a temperature of 85° C. until almost no methanol was distilled out. After the completion of the reaction of 1,4-butanediol and methyl acrylate, the obtained reaction liquid was heated to 88° C., and cyclohexane and unreacted methyl acrylate were removed by azeotropic distillation, to obtain 1088 g of a reaction mixture.

As a first extraction operation, the obtained reaction mixture in an amount of 1088 g was supplied at a flow rate of 50 mL/h, and pure water was also supplied at a flow rate of 29.5 mL/h to the upper part of a pulsating type continuous extraction tower (filled tower with 25 mm diameter and 1.4 m length). Also, cyclohexane was supplied over 22 hours at a flow rate of 87.8 mL/h to the lower part of the continuous extraction tower. The inside of the tower was heated to 30 to 35° C., and extraction was carried out continuously, to obtain a cyclohexane layer containing 1,4-butanediol diacrylate as a by-product, and a water layer containing the resulting 4-hydroxybutyl acrylate and unreacted 1,4-butanediol.

As a second extraction operation, 1200 mL of the obtained water layer was supplied at a flow rate of 50 mL/h to the upper part of the continuous extraction tower, and toluene as an extraction solvent was supplied over 24 hours at a flow rate of 87.5 mL/h to the lower part of the continuous extraction tower. The inside of the tower was heated to 35 to 40° C., and the continuous extraction was carried out, to obtain a toluene layer containing 4-hydroxybutyl acrylate, and a water layer containing 1,4-butanediol. The content of 1,4-butanediol diacrylate in the components other than toluene contained in the toluene layer was analyzed by gas chromatography. As a result, the content was found to be 0.11% by mass.

Next, a 2 L three-necked glass flask was charged with 1400 g of the toluene layer obtained by the second extraction operation, and 0.008 g of hydroquinone monomethyl ether as a polymerization inhibitor was added to the flask. The temperature in the bottom part of the flask was adjusted to 74 to 85° C., and toluene was removed under reduced pressure of 280 to 20 hPa by distillation for 14 hours, to concentrate 4-hydroxybutyl acrylate. The resulting condensed material was distilled by a thin film distillatory, and the acid matter in the distillate was measured. As a result, the content of acrylic acid in the distillate was 0.0065% by mass (65 ppm).

Example III-2

To a 2 L four-necked glass flask were attached a 20-stage Oldershaw, a reflux condenser and a gas introduction tube, and the flask was charged with 675 g of 1,4-butanediol, 430.45 g (5.0 moles) of methyl acrylate, 100 g of cyclohexane and 0.72 g of phenothiazine as a polymerization inhibitor. Thereafter, 3.00 g of dioctyltin oxide was added to the flask. While a nitrogen gas containing 7% by volume of oxygen gas was blown into the flask at a flow rate of 20 mL/min, the reaction of 1,4-butanediol and methyl acrylate was carried out at 85° C. for 10 hours.

After the azeotropic mixture of the resulting methanol and cyclohexane was put in a decanter, 50 mL of water was continuously added to the decanter. While a separated aqueous methanol solution was removed from the decanter, the reaction of 1,4-butanediol and methyl acrylate was carried out at a temperature of 85° C. until almost no methanol was distilled out.

After the completion of the reaction of 1,4-butanediol and methyl acrylate, the obtained reaction liquid was heated to 80° C. under reduced pressure, and cyclohexane and unreacted methyl acrylate were removed by distillation to obtain 1080 g of a reaction mixture.

Next, as a first extraction operation, the obtained reaction mixture in an amount of 1080 g was supplied at a flow rate of 50 mL/h, and pure water was also supplied at a flow rate of 29.5 mL/h to the upper part of a pulsating type continuous extraction tower (filled tower with 25 mm diameter and 1.4 m length), and cyclohexane was supplied over 22 hours at a flow rate of 87.8 mL/h to the lower part of the continuous extraction tower. The inside of the tower was heated to 30 to 35° C., and extraction was carried out continuously, to obtain a cyclohexane layer containing 1,4-butanediol diacrylate as a by-product, and a water layer containing the resulting 4-hydroxybutyl acrylate and unreacted 1,4-butanediol.

As a second extraction operation, 1200 mL of the obtained water layer was supplied at a flow rate of 50 mL/h to the upper part of the continuous extraction tower, and toluene as an extraction solvent was supplied over 24 hours at a flow rate of 87.5 mL/h to the lower part of the continuous extraction tower. The inside of the tower was heated to 35 to 40° C., and the continuous extraction was carried out, to obtain a toluene layer containing 4-hydroxybutyl acrylate, and a water layer containing 1,4-butanediol. The content of 1,4-butanediol diacrylate in the components other than toluene contained in the toluene layer was analyzed by gas chromatography. As a result, the content was found to be 0.10% by mass.

Next, a 2 L three-necked glass flask was charged with 1400 g of the toluene layer obtained by the second extraction operation, and 0.008 g of hydroquinone monomethyl ether as a polymerization inhibitor was added to the flask. The temperature in the bottom part of the flask was adjusted to 74 to 85° C., and toluene was removed under reduced pressure of 280 to 20 hPa by distillation for 14 hours, to concentrate 4-hydroxybutyl acrylate.

Next, a 2 L three-necked glass flask was charged with 1400 g of the toluene layer obtained by the second extraction operation, and 0.008 g of hydroquinone monomethyl ether as a polymerization inhibitor was added to the flask. The temperature in the bottom part of the flask was adjusted to 74 to 85° C., and toluene was removed under reduced pressure of 280 to 20 hPa by distillation for 14 hours, to concentrate 4-hydroxybutyl acrylate. The resulting condensed material was distilled by a thin film distillatory, and the content of an acid in the distillate was measured. As a result, the content of acrylic acid in the distillate was 0.0076% by mass (76 ppm).

Example III-3

To a 2 L four-necked glass flask were attached a 20-stage Oldershaw, a reflux condenser and a gas introduction tube, and the flask was charged with 675 g of 1,4-butanediol, 430.45 g (5.0 moles) of methyl acrylate, 100 g of cyclohexane and 0.72 g of phenothiazine as a polymerization inhibitor. Thereafter, 3.80 g of dioctyltin oxide was added to the flask. While a nitrogen gas containing 7% by volume of oxygen gas was blown into the flask at a flow rate of 20 mL/min, the reaction of 1,4-butanediol and methyl acrylate was carried out at 85° C. for 5 hours.

After the azeotropic mixture of the resulting methanol and cyclohexane was put in a decanter, 50 mL of water was continuously added to the decanter. While a separated aqueous methanol solution was removed from the decanter, the reaction of 1,4-butanediol and methyl acrylate was carried out at a temperature of 85° C. until almost no methanol was distilled out.

After the completion of the reaction of 1,4-butanediol and methyl acrylate, the obtained reaction liquid was heated to 88° C., and unreacted methyl acrylate was removed by azeotropic distillation with cyclohexane, to obtain 1109 g of a reaction mixture.

Next, as a first extraction operation, the obtained reaction mixture in an amount of 1109 g was supplied at a flow rate of 50 mL/h, and pure water was also supplied at a flow rate of 29.5 mL/h to the upper part of a pulsating type continuous extraction tower (filled tower with 25 mm diameter and 1.4 m length), and cyclohexane was supplied over 22 hours at a flow rate of 87.8 mL/h to the lower part of the continuous extraction tower. The inside of the tower was heated to 30 to 35° C., and extraction was carried out continuously, to obtain a cyclohexane layer containing 1,4-butanediol diacrylate as a by-product, and a water layer containing the resulting 4-hydroxybutyl acrylate and unreacted 1,4-butanediol.

Next, the obtained water layer was dropwise added at a flow rate of 95 g/h to a column filled with 16 g of a strongly basic anion-exchange resin (trade name: Amberlite IRA 900 JCL, manufactured by Organo Corporation) to bring the water layer into contact with the strongly basic anion-exchange resin. Thereafter, as a second extraction operation, 1200 mL of the obtained water layer was supplied at a flow rate of 50 mL/h to the upper part of the continuous extraction tower, and toluene as an extraction solvent was supplied over 24 hours at a flow rate of 87.5 mL/h to the lower part of the continuous extraction tower. The inside of the tower was heated to 35 to 40° C., and the continuous extraction was carried out, to obtain a toluene layer containing 4-hydroxybutyl acrylate, and a water layer containing 1,4-butanediol. The content of 1,4-butanediol diacrylate in the components other than toluene contained in the toluene layer was analyzed by gas chromatography. As a result, the content was found to be 0.12% by mass.

Next, a 2 L three-necked glass flask was charged with 1400 g of the toluene layer obtained by the second extraction operation, and 0.008 g of hydroquinone monomethyl ether as a polymerization inhibitor was added to the flask. The temperature in the bottom part of the flask was adjusted to 74 to 85° C., and toluene was removed under reduced pressure of 280 to 20 hPa by distillation for 14 hours to concentrate 4-hydroxybutyl acrylate.

Next, a 2 L three-necked glass flask was charged with 1400 g of the toluene layer obtained by the second extraction operation, and 0.008 g of hydroquinone monomethyl ether as a polymerization inhibitor was added to the flask. The temperature in the bottom part of the flask was adjusted to 74 to 85° C., and toluene was removed under reduced pressure of 280 to 20 hPa by distillation for 14 hours, to concentrate 4-hydroxybutyl acrylate. The resulting condensed material was distilled by a thin film distillatory, and the content of an acid in the distillate was measured. As a result, the content of acrylic acid in the distillate was 0.0013% by mass (13 ppm).

From the results of Example III-3, it was found that 4-hydroxybutyl acrylate having a content of acrylic acid of 15 ppm or lower can be prepared efficiently by using dioctyltin oxide as a catalyst for transesterification, and moreover bringing the water layer into contact with the basic ion-exchange resin.

Example III-4

The water layer obtained by the second extraction operation in Example III-1 was concentrated, to give 340 g of a mixture of 1,4-butanediol and dioctyltin oxide.

Next, 340 g of the collected mixture was used in place of 1,4-butanediol used in Example III-1, and new 1,4-butanediol was added in the same amount as that of 1,4-butanediol used in Example III-1. At that time, since a dialkyltin oxide is contained in the mixture, a catalyst for transesterification was not additionally added.

Thereafter, the reaction of 1,4-butanediol and methyl acrylate was carried out in the same manner as in Example III-1 at a temperature of 85° C. for 10 hours.

After the completion of the reaction of 1,4-butanediol and methyl acrylate, the obtained reaction liquid was heated to 88° C. under reduced pressure, and unreacted methyl acrylate was removed by distillation, to obtain 1080 g of a reaction mixture.

The components other than the solvent in the obtained reaction mixture were analyzed by gas chromatography. As a result, the content of 4-hydroxybutyl acrylate was 50.1% by mass, the content of 1,4-butanediol was 37.3% by mass, and the content of 1,4-butanediol diacrylate was 12.2% by mass in the components.

As a first extraction operation, the obtained reaction mixture in an amount of 1088 g was supplied at a flow rate of 50 mL/h, and pure water was also supplied at a flow rate of 29.5 mL/h to the upper part of a pulsating type continuous extraction tower (filled tower with 25 mm diameter and 1.4 m length), cyclohexane was supplied over 22 hours at a flow rate of 87.8 mL/h to the lower part of the continuous extraction tower. The inside of the tower was heated to 30 to 35° C., and extraction was carried out continuously, to obtain a cyclohexane layer containing 1,4-butanediol diacrylate as a by-product, and a water layer containing the resulting 4-hydroxybutyl acrylate and unreacted 1,4-butanediol.

Next, the obtained water layer was dropwise added at a flow rate of 95 g/h to a column filled with 16 g of a weakly basic anion-exchange resin (trade name: Amberlite IRA 98, manufactured by Organo Corporation) to bring the water layer into contact with the weakly basic anion-exchange resin.

Next, as a second extraction operation, 1200 mL of the obtained water layer was supplied at a flow rate of 50 mL/h to the upper part of the continuous extraction tower, and toluene as an extraction solvent was supplied over 24 hours at a flow rate of 87.5 mL/h to the lower part of the continuous extraction tower. The inside of the tower was heated to 35 to 40° C., and the continuous extraction was carried out, to obtain a toluene layer containing 4-hydroxybutyl acrylate and a water layer containing 1,4-butanediol. The content of 1,4-butanediol diacrylate in the components other than toluene contained in the toluene layer was analyzed by gas chromatography. As a result, the content was found to be 0.11% by mass.

A 2 L three-necked glass flask was charged with the toluene layer in an amount of 1400 g obtained by the second extraction operation, and 0.008 g of hydroquinone monomethyl ether as a polymerization inhibitor was added to the flask. The temperature in the bottom part of the flask was adjusted to 74 to 85° C., and toluene was removed under reduced pressure of 280 to 20 hPa by distillation for 14 hours, to concentrate 4-hydroxybutyl acrylate.

The components contained in the condensed material were analyzed by gas chromatography. As a result, 98.3% by mass of 4-hydroxybutyl acrylate, 0.11% by mass of 1,4-butanediol diacrylate and 1.2% by mass of 1,4-butanediol were contained in the components. The resulting condensed material was distilled by a thin film distillatory, and the content of an acid in the distillate was measured. As a result, the content of acrylic acid in the distillate was 0.0015% by mass (15 ppm).

From the above-mentioned results, it was found that 4-hydroxybutyl acrylate having a low content of an acid can be efficiently collected even when the extraction operation is carried out by reusing the catalyst for transesterification.

Example III-5

A reaction mixture was obtained by carrying out the reaction of 1,4-butanediol and methyl acrylate at 85° C. for 10 hours in the same manner as in Example III-1, except that 6.14 g (0.025 moles) of tetramethyl titanate (purity: 70% by mass) was used as a catalyst for transesterification in Example III-1. The components other than the solvent in the obtained reaction mixture were analyzed by gas chromatography. As a result, the content of 4-hydroxybutyl acrylate was 51.1% by mass, the content of 1,4-butanediol was 36.5% by mass, and the content of 1,4-butanediol diacrylate was 12.4% by mass.

Next, as a first extraction operation, 1088 g of the obtained reaction mixture was supplied at a flow rate of 50 mL/h, and pure water was supplied at a flow rate of 29.5 mL/h to an upper part of a pulsating type continuous extraction tower (filled tower with 25 mm diameter and 1.4 m length), and cyclohexane was supplied at a flow rate of 87.8 mL/h to a lower part of the continuous extraction tower. As a result, the resulting 1,4-butanediol diacrylate could not be separated from the reaction mixture, since the reaction mixture in the continuous extraction tower became opaque, and an insoluble matter was precipitated.

From the results of Examples III-1 to III-5, it can be understood that when a dialkyltin oxide which is a tin compound is used as a catalyst for transesterification (Examples III-1 to III-4), 4-hydroxybutyl methacrylate can be easily separated from the reaction mixture as compared with the case where tetramethyl titanate is used as a catalyst for transesterification (Example III-5).

Comparative Example III-1

The reaction of 1,4-butanediol and methyl acrylate was carried out in the same manner as in Example III-1, except that dioctyltin oxide was not used as a catalyst in Example III-1. After 3 hours passed from the starting of the reaction, the amount of methanol was weighed. As a result, methanol was not generated. The reaction mixture was analyzed by gas chromatography. As a result, it could not be confirmed at all that 4-hydroxybutyl acrylate was generated.

Comparative Example III-2

To a 2 L four-necked glass flask were attached a 20-stage Oldershaw, a reflux condenser and an air introduction tube, and the flask was charged with 676 g (7.5 moles) of 1,4-butanediol, 360.5 g (5.0 moles) of acrylic acid, 400 g of cyclohexane and 0.721 g of phenothiazine as a polymerization inhibitor. Thereafter, 3.6 g of refined 98% sulfuric acid was added to the flask. While a nitrogen gas containing 7% by volume of oxygen gas was blown into the flask at a flow rate of 20 mL/min, 1,4-butanediol and acrylic acid were heated to 85° C., the resulting water was removed from the system by azeotropic dehydration, and the reaction of 1,4-butanediol and methyl acrylate was carried out at 85° C. for 12 hours.

After the completion of the reaction of 1,4-butanediol and methyl acrylate, the obtained reaction liquid was neutralized with an aqueous 10% sodium hydroxide solution, and the first extraction operation and the second extraction operation were carried out in the same manner as in Example III-1, to obtain a toluene solution containing 4-hydroxybutyl acrylate.

Next, a 2 L three-necked glass flask was charged with 1400 g of the toluene solution (toluene layer) of 4-hydroxybutyl acrylate obtained by the second extraction operation, and 0.008 g of hydroquinone monomethyl ether as a polymerization inhibitor was added to the flask. The temperature in the bottom part of the flask was adjusted to 74 to 85° C., and toluene was removed under reduced pressure of 280 to 20 hPa by distillation for 14 hours, to concentrate 4-hydroxybutyl acrylate.

The resulting condensed material was distilled by a thin film distillatory, and the acid matter in the distillate was measured. As a result, the content of acrylic acid in the distillate was 0.075% by mass (750 ppm).

From the results of Comparative Example III-2, it can be understood that when 4-hydroxybutyl acrylate is prepared by not a transesterification reaction but an esterification reaction by using acrylic acid in place of methyl acrylate, 4-hydroxybutyl acrylate having a content of acrylic acid of 50 ppm or lower cannot be prepared, since the content of acrylic acid considerably exceeds 50 ppm.

From the above-mentioned results, it can be understood that 4-hydroxybutyl acrylate obtained by the process for preparing 4-hydroxybutyl acrylate according to each example has a content of acrylic acid of 50 ppm or lower in the 4-hydroxybutyl acrylate. Therefore, the 4-hydroxybutyl acrylate has low skin irritation, and is thus suitable for not only as a raw material for pressure-sensitive adhesives for medical uses which may cause problems such as skin eruption and inflammation, but also as a raw material for coating agents for electronic materials, ultraviolet-curable or electron beam-curable photosensitive resin compositions for which the working environment is considered to be important.

Example IV of the Fourth Invention

Example IV-1

To a 2 L four-necked glass flask were attached a 20-stage Oldershaw, a reflux condenser and an air introduction tube, and the flask was charged with 676 g (7.5 moles) of 1,4-butanediol, 430.5 g (5.0 moles) of methyl acrylate, 101 g of cyclohexane and 0.72 g of phenothiazine as a polymerization inhibitor. Thereafter, 3.62 g of dioctyltin oxide was added. While a nitrogen gas containing 7% by volume of oxygen gas was blown into the flask at a flow rate of 20 mL/min, the reaction of 1,4-butanediol and methyl acrylate was carried out at 85° C. for 10 hours.

After the azeotropic mixture of the resulting methanol and cyclohexane was put in a decanter, 50 mL of water was continuously added to the decanter. While a separated aqueous methanol solution was removed from the decanter, the reaction of 1,4-butanediol and methyl acrylate was carried out at a temperature of 85° C. until almost no methanol was distilled out.

After the completion of the reaction of 1,4-butanediol and methyl acrylate, the obtained reaction liquid was heated to 88° C., and unreacted methyl acrylate was removed by azeotropic distillation with cyclohexane, to obtain 1220 g of a reaction mixture.

As a first extraction operation, 1220 g of the obtained reaction mixture was supplied at a flow rate of 40 mL/h, and pure water was also supplied at a flow rate of 23.6 mL/h to the upper part of a pulsating type continuous extraction tower (filled tower of 25 mm in diameter and 1.4 m in height) while the temperature of the whole of the continuous extraction tower was kept at 20° C., cyclohexane was supplied over 24 hours at a flow rate of 70.2 mL/h to the lower part of the continuous extraction tower, and extraction was carried out continuously, to obtain a cyclohexane layer containing 1,4-butanediol diacrylate as a by-product, and a water layer containing the resulting 4-hydroxybutyl acrylate and unreacted 1,4-butanediol.

The content of 1,4-butanediol diacrylate in the obtained water layer was analyzed by gas chromatography. As a result, it was confirmed that the removal ratio of 1,4-butanediol diacrylate from the reaction mixture to the cyclohexane layer was 98.58%.

Next, as a second extraction operation, while the temperature of the whole of a pulsating type continuous extraction tower (filled tower of 25 mm in diameter and 1.4 m in height) was kept at 20° C., 1200 mL of the obtained water layer was supplied at a flow rate of 30 mL/h to the upper part of the continuous extraction tower, and toluene as an extraction solvent was supplied over 24 hours at a flow rate of 100 mL/h to the lower part of the continuous extraction tower. As a result, a toluene layer containing 4-hydroxybutyl acrylate, and a water layer containing 1,4-butanediol were obtained.

The extraction ratio of 4-hydroxybutyl acrylate from the water layer extracted by the first extraction operation to the toluene layer was analyzed by gas chromatography. As a result, the extraction ratio of 4-hydroxybutyl acrylate was 86.3%.

Next, the obtained toluene layer was concentrated by heating to 85° C. and reducing the pressure from 280 hPa to 20 hPa over 7 hours. As a result, the content of 1,4-butanediol diacrylate in the obtained concentrated material was 0.61% by mass.

Example IV-2

The same procedure as in Example IV-1 was carried out except that the temperature in the entire pulsating type continuous extraction tower was changed from 20° C. to 30° C. when carrying out the first extraction operation and the second extraction operation in Example IV-1.

At the time of carrying out the above-mentioned process, the content of 1,4-butanediol diacrylate in the obtained water layer extracted by the first extraction operation was analyzed by gas chromatography. As a result, it was confirmed that the removal ratio of 1,4-butanediol diacrylate from the reaction mixture to the cyclohexane layer was 98.89%.

The extraction ratio of 4-hydroxybutyl acrylate from the water layer extracted by the first extraction operation to the toluene layer by the second extraction operation was analyzed by gas chromatography. As a result, the extraction ratio of 4-hydroxybutyl acrylate was 89.32%.

Next, the obtained toluene layer was concentrated by heating to 85° C., and reducing the pressure from 280 hPa to 20 hPa over 7 hours. As a result, the content of 1,4-butanediol diacrylate in the obtained concentrated material was 1.26% by mass.

Example IV-3

The same procedure as in Example IV-1 was carried out except that the temperature in the entire pulsating type continuous extraction tower was changed from 20° C. to 35° C. at the time of carrying out the first extraction operation and the second extraction operation in Example IV-1.

At the time of carrying out the above-mentioned process, the content of 1,4-butanediol diacrylate in the obtained water layer extracted by the first extraction operation was analyzed by gas chromatography. As a result, it was confirmed that the removal ratio of 1,4-butanediol diacrylate from the reaction mixture to the cyclohexane layer was 98.93%.

The extraction ratio of 4-hydroxybutyl acrylate from the water layer extracted by the first extraction operation to the toluene layer by the second extraction operation was analyzed by gas chromatography. As a result, the extraction ratio of 4-hydroxybutyl acrylate was 90.46%.

Next, the obtained toluene layer was concentrated by heating to 85° C., and reducing the pressure from 280 hPa to 20 hPa over 7 hours. As a result, the content of 1,4-butanediol diacrylate in the obtained concentrated material was 1.94% by mass.

Comparative Example IV-1

The same procedure as in Example IV-1 was carried out except that the temperature in the entire pulsating type continuous extraction tower was changed from 20° C. to 40° C. at the time of carrying out the first extraction operation and the second extraction operation in Example IV-1.

At the time of carrying out the above-mentioned process, the content of 1,4-butanediol diacrylate in the obtained water layer extracted by the first extraction operation was analyzed by gas chromatography. As a result, it was confirmed that the removal ratio of 1,4-butanediol diacrylate from the reaction mixture to the cyclohexane layer was 98.94%.

The extraction ratio of 4-hydroxybutyl acrylate from the water layer extracted by the first extraction operation to the toluene layer by the second extraction operation was analyzed by gas chromatography. As a result, the extraction ratio of 4-hydroxybutyl acrylate was 91.62%.

Next, the obtained toluene layer was concentrated by heating to 85° C., and reducing the pressure from 280 hPa to 20 hPa over 7 hours. As a result, the content of 1,4-butanediol diacrylate in the obtained concentrated material was 3.60% by mass.

Comparative Example IV-2

The same procedure as in Example IV-1 was carried out except that the temperature in the entire pulsating type continuous extraction tower was changed from 20° C. to 50° C. at the time of carrying out the first extraction operation and the second extraction operation in Example IV-1.

At the time of carrying out the above-mentioned process, the content of 1,4-butanediol diacrylate in the obtained water layer extracted by the first extraction operation was analyzed by gas chromatography. As a result, it was confirmed that the removal ratio of 1,4-butanediol diacrylate from the reaction mixture to the cyclohexane layer was 98.94%.

The extraction ratio of 4-hydroxybutyl acrylate from the water layer extracted by the first extraction operation to the toluene layer by the second extraction operation was analyzed by gas chromatography. As a result, the extraction ratio of 4-hydroxybutyl acrylate was 92.86%.

Next, the obtained toluene layer was concentrated by heating to 85° C., and reducing the pressure from 280 hPa to 20 hPa over 7 hours. As a result, the content of 1,4-butanediol diacrylate in the obtained concentrated material was 4.04% by mass.

Comparative Example IV-3

The same procedure as in Example IV-1 was carried out except that the temperature in the entire pulsating type continuous extraction tower was changed from 20° C. to 60° C. at the time of carrying out the first extraction operation and the second extraction operation in Example IV-1.

At the time of carrying out the above-mentioned process, the content of 1,4-butanediol diacrylate in the obtained water layer extracted by the first extraction operation was analyzed by gas chromatography. As a result, it was confirmed that the removal ratio of 1,4-butanediol diacrylate from the reaction mixture to the cyclohexane layer was 98.94%.

The extraction ratio of 4-hydroxybutyl acrylate from the water layer extracted by the first extraction operation to the toluene layer by the second extraction operation was analyzed by gas chromatography. As a result, the extraction ratio of 4-hydroxybutyl acrylate was 94.45%.

Next, the obtained toluene layer was concentrated by heating to 85° C., and reducing the pressure from 280 hPa to 20 hPa over 7 hours. As a result, the content of 1,4-butanediol diacrylate in the obtained concentrated material was 4.77% by mass.

From the above-mentioned results, it can be understood that the remaining amount of 1,4-butanediol diacrylate can be considerably decreased in the examples as compared with the comparative examples, since an aliphatic or alicyclic hydrocarbon compound was used as an extraction solvent and the extraction temperature in the first extraction operation was within a prescribed temperature range in the examples.

Furthermore, it can be understood that 4-hydroxybutyl acrylate can be stably extracted at an extraction ratio of 90% or higher in the examples, since the aromatic hydrocarbon compound was used as an extraction solvent in the second extraction operation, and the extraction temperature was adjusted to a prescribed temperature in the examples.

Accordingly, it can be understood that according to the process for preparing 4-hydroxybutyl acrylate of the examples, 4-hydroxybutyl acrylate can be efficiently prepared by the transesterification reaction of 1,4-butanediol and an acrylic acid alkyl ester, since an alkyltin oxide is used as a catalyst for transesterification, and that the amount of 1,4-butandiol diacrylate as a by-product can be decreased although the alkyltin oxide is used.

Experiment Example

The cyclohexane layer (containing dioctyltin oxide) obtained by the first extraction operation and the water layer (containing 1,4-butanediol) obtained by the second extraction operation in each example were respectively concentrated. Using the obtained concentrated liquids and using 1,4-butanediol and methyl acrylate, the amounts of respective components were adjusted to give a composition having the same components as in Example IV-1, and thereafter, the same procedure as in Example IV-1 was carried out, to give 4-hydroxybutyl acrylate. As a result, it was confirmed that 4-hydroxybutyl acrylate can be obtained in an extraction ratio similar to that in Example IV-1 in which each content of 1,4-butanediol diacrylate and 1,4-butanediol is low.

From the above-mentioned results, it can be understood that the process for preparing 4-hydroxybutyl acrylate in each example is excellent in environmental preservation, since the cyclohexane layer obtained in the first extraction operation and the water layer obtained in the second extraction operation in each example can be reused, and the amount of waste fluid to be discarded can be reduced.

Example V of the Fifth Invention

Example V-1

To a 2 L four-necked glass flask were attached an Oldershaw distillation tower (20 steps), a reflux condenser and a gas introduction tube, and the flask was charged with 675 g (7.5 moles) of 1,4-butanediol, 430.45 g (5.0 moles) of methyl acrylate, 100 g of cyclohexane and 0.721 g of phenothiazine as a polymerization inhibitor. Thereafter, 3.61 g of dioctyltin oxide as a catalyst for transesterification was added to the flask. While a nitrogen gas containing 7% by volume of oxygen was blown into the flask at a flow rate of 20 mL/min, the transesterification reaction of 1,4-butanediol and methyl acrylate was carried out at 85° C.

In addition, the azeotropic mixture of methanol and cyclohexane by-products generated in the transesterification of 1,4-butanediol and methyl acrylate was taken out from the distillation tower, and introduced into a 500 mL decanter as required. To the decanter, 50 mL of 1,4-butanediol was gradually added, and the alcohol solution containing separated methanol and 1,4-butanediol was taken out from the decanter to separate 200 g of the alcohol solution from cyclohexane.

The transesterification reaction of 1,4-butanediol and methyl acrylate was carried out at 85° C. until almost no methanol was distilled out, so that the transesterification reaction of 1,4-butanediol and methyl acrylate was terminated, to obtain a reaction mixture.

The obtained reaction mixture was heated to 88° C., and unreacted methyl acrylate was removed by azeotropic distillation with cyclohexane, to obtain 1088 g of crude 4-hydroxybutyl acrylate.

Next, the obtained crude 4-hydroxybutyl acrylate was collected by extraction and further subjected to thin film distillation, to obtain 489 g of refined 4-hydroxybutyl acrylate.

On the other hand, 200 g of the alcohol solution taken out from the decanter was heated to 80° C., the degree of pressure reduction was gradually increased, and finally the degree of pressure reduction was adjusted to 250 kPa, to remove methanol by distillation. As a result, the amount of methanol removed by distillation was 128.5 g, and the amount of remaining 1,4-butanediol was 70.5 g. Accordingly, it can be understood that methanol which is generated as a by-product in the transesterification of 1,4-butanediol and methyl acrylate can be efficiently collected.

Additionally, the collected methanol was analyzed by gas chromatography. As a result, a notable peak attributed to methanol was observed, and slight peaks attributed to cyclohexane and methyl acrylate were also observed. Accordingly, it was confirmed that methanol which is a by-product having a relatively high purity can be easily collected, and that the methanol can be used effectively not only as a raw material for organic compound synthesis but also as a fuel.

Example V-2

To a 2 L four-necked glass flask were attached a 20-stage Oldershaw, a reflux condenser and a gas introduction tube. This flask was charged with 70.5 g of 1,4-butanediol collected in Example V-1, and 604.5 g of new 1,4-butanediol, 430.45 g of methyl acrylate, 100 g of cyclohexane and 0.721 g of phenothiazine as a polymerization inhibitor were charged. Thereafter, 3.61 g of dioctyltin oxide as a catalyst for transesterification was added to the flask. While a nitrogen gas containing 7% by volume of oxygen was blown into the flask at a flow rate of 20 mL/min, the reaction of 1,4-butanediol and methyl acrylate was carried out at 85° C.

In addition, the azeotropic mixture of methanol and cyclohexane by-products generated in the transesterification of 1,4-butanediol and methyl acrylate was taken out from the distillation tower, and introduced into a 500 mL decanter as required. To the decanter, 50 mL of 1,4-butanediol was gradually added, and the alcohol solution containing separated methanol and 1,4-butanediol was taken out from the decanter, to separate the alcohol solution from cyclohexane.

The transesterification reaction of 1,4-butanediol and methyl acrylate was carried out at 85° C. until almost no methanol was distilled out, so that the transesterification reaction of 1,4-butanediol and methyl acrylate was terminated, to obtain a reaction mixture.

The obtained reaction mixture was heated to 88° C., and unreacted methyl acrylate was removed by azeotropic distillation with cyclohexane, to obtain 1088 g of crude 4-hydroxybutyl acrylate.

Next, the obtained crude 4-hydroxybutyl acrylate was collected by extraction, and further subjected to thin film distillation, to obtain 483 g of refined 4-hydroxybutyl acrylate.

On the other hand, 200 g of the alcohol solution taken out from the decanter was heated to 80° C., and the degree of pressure reduction was gradually increased. Finally the reduced pressure was adjusted to 250 kPa, to remove methanol by distillation. As a result, the amount of methanol removed by distillation was 128.5 g, and the amount of remaining 1,4-butanediol was 70.5 g. Accordingly, it can be understood that methanol which is generated as a by-product in the transesterification of 1,4-butanediol and methyl acrylate can be efficiently collected.

Additionally, the collected methanol was analyzed by gas chromatography. As a result, a notable peak attributed to methanol was observed, and slight peaks attributed to cyclohexane and methyl acrylate were also observed. Accordingly, it was confirmed that methanol which is a by-product having a relatively high purity can be easily collected, and that the methanol can be effectively used not only as a raw material for organic compound synthesis but also as a fuel.

Example V-3

To a 2 L four-necked glass flask were attached an Oldershaw distillation tower (20 steps), a reflux condenser and a gas introduction tube, and the flask was charged with 270.4 g (3.0 moles) of 1,4-butanediol, 1033.1 g (12.0 moles) of methyl acrylate, 81 g of cyclohexane and 2.163 g of phenothiazine as a polymerization inhibitor. Thereafter, 3.47 g of dioctyltin oxide as a catalyst for transesterification was added to the flask. While a nitrogen gas containing 7% by volume of oxygen was blown into the flask at a flow rate of 10 mL/min, the transesterification reaction of 1,4-butanediol and methyl acrylate was carried out at 85° C.

In addition, the azeotropic mixture of methanol and cyclohexane by-products generated in the transesterification of 1,4-butanediol and methyl acrylate was taken out from the distillation tower, and introduced into a 500 mL decanter as required. To the decanter, 43 mL of 1,4-butanediol was gradually added, and the alcohol solution containing separated methanol and 1,4-butanediol was taken out from the decanter, to separate 436 g of the alcohol solution from cyclohexane.

The transesterification reaction of 1,4-butanediol and methyl acrylate was carried out at 85° C. until almost no methanol was distilled out, so that the transesterification reaction of 1,4-butanediol and methyl acrylate was terminated, to obtain a reaction mixture.

The obtained reaction mixture was heated to 90° C., and unreacted methyl acrylate was removed by azeotropic distillation with cyclohexane, to obtain 1054 g of crude 1,4-butyl diacrylate.

Next, the obtained crude 1,4-butyl diacrylate was collected by extraction, cyclohexane was concentrated, and further the crude 1,4-butyl diacrylate was subjected to thin film distillation, to obtain 508 g of refined 4-hydroxybutyl acrylate.

On the other hand, 436 g of the alcohol solution taken out from the decanter was heated to 80° C., and the degree of pressure reduction was gradually increased. Finally the reduced pressure was adjusted to 250 kPa, to remove methanol by distillation. As a result, the amount of methanol removed by distillation was 182.7 g, and the amount of remaining 1,4-butanediol was 253 g. Accordingly, it can be understood that methanol which is generated as a by-product in the transesterification of 1,4-butanediol and methyl acrylate can be efficiently collected.

Additionally, the collected methanol was analyzed by gas chromatography. As a result, a notable peak attributed to methanol was observed, and slight peaks attributed to cyclohexane and methyl acrylate were also observed. Accordingly, it was confirmed that methanol which is a by-product having a relatively high purity can be easily collected, and that the methanol can be used effectively not only as a raw material for organic compound synthesis but also as a fuel.

Example V-4

To a 2 L four-necked glass flask were attached an Oldershaw distillation tower (20 steps), a reflux condenser and a gas introduction tube, and the flask was charged with 250.3 g of 1,4-butanediol collected in Example V-3, 20.1 g of new 1,4-butanediol, 1033.1 g of methyl acrylate, 81 g of cyclohexane and 2.163 g of phenothiazine as a polymerization inhibitor. Thereafter, 3.47 g of dioctyltin oxide as a catalyst for transesterification was added to the flask. While a nitrogen gas containing 7% by volume of oxygen was blown into the flask at a flow rate of 10 mL/min, the transesterification reaction of 1,4-butanediol and methyl acrylate was carried out at 85° C.

In addition, the azeotropic mixture of methanol and cyclohexane by-products generated in the transesterification of 1,4-butanediol and methyl acrylate was taken out from the distillation tower, and introduced into a 500 mL decanter as required. To the decanter, 50 mL of 1,4-butanediol was gradually added, and the alcohol solution containing separated methanol and 1,4-butanediol was taken out from the decanter, to separate 437 g of the alcohol solution from cyclohexane.

The transesterification reaction of 1,4-butanediol and methyl acrylate was carried out at 85° C. until almost no methanol was distilled out, so that the transesterification reaction of 1,4-butanediol and methyl acrylate was terminated, to obtain a reaction mixture.

The obtained reaction mixture was heated to 90° C., and unreacted methyl acrylate was removed by azeotropic distillation with cyclohexane, to obtain 1054 g of crude 4-hydroxybutyl acrylate.

Next, the obtained crude 4-hydroxybutyl acrylate was collected by extraction, and further subjected to thin film distillation to obtain 508 g of refined 4-hydroxybutyl acrylate.

On the other hand, 436 g of the alcohol solution taken out from the decanter was heated to 80° C., and the degree of pressure reduction was gradually increased. Finally the degree of pressure reduction was adjusted to 250 kPa, to remove methanol by distillation. As a result, the amount of methanol removed by distillation was 182.7 g, and the amount of remaining 1,4-butanediol was 253 g. Accordingly, it can be understood that methanol which is generated as a by-product in the transesterification of 1,4-butanediol and methyl acrylate can be efficiently collected.

Additionally, the collected methanol was analyzed by gas chromatography. As a result, a notable peak attributed to methanol was observed, and slight peaks attributed to cyclohexane and methyl acrylate were also observed. Accordingly, it was confirmed that methanol which is a by-product having a relatively high purity can be easily collected, and that the methanol can be effectively used not only as a raw material for organic compound synthesis but also as a fuel.

Next, the remaining 1,4-butanediol was used as a raw material of 1,4-butanediol when a new transesterification of 1,4-butanediol and methyl acrylate is carried out. As a result, it was confirmed that the transesterification of 1,4-butanediol and methyl acrylate could be efficiently carry out.

From the above-mentioned results, it can be understood that according to the process for preparing an alkyl diacrylate of the present invention, not only it is made possible to efficiently collect an alcohol which is generated as a by-product when preparing an alkyl diacrylate by a transesterification method, but also it is made possible to reuse a polyhydric alcohol separated from the by-product alcohol in a new transesterification reaction of a polyhydric alcohol and an acrylic acid alkyl ester.

Example V-5

To a 2 L four-necked glass flask were attached a 20-stage Oldershaw, a reflux condenser and a gas introduction tube, and the flask was charged with 886.6 g (7.5 moles) of 1,6-hexanediol, then 430.45 g (5.0 moles) of methyl acrylate, 100 g of cyclohexane and 0.721 g of phenothiazine as a polymerization inhibitor. Thereafter, 3.61 g of dioctyltin oxide as a catalyst for transesterification was added to the flask. While a nitrogen gas containing 7% by volume of oxygen was blown into the flask at a flow rate of 20 mL/min, the reaction of 1,6-hexanediol and methyl acrylate was carried out at 85° C.

In addition, the azeotropic mixture of methanol and cyclohexane by-products generated in the transesterification of 1,6-hexanediol and methyl acrylate was taken out from the distillation tower as required, and introduced into a heatable 500 mL decanter. To the decanter, 50 mL of 1,6-hexanediol heated to 45° C. was gradually added, and the alcohol solution containing separated methanol and 1,6-hexanediol was taken out from the decanter, to separate 200 g of the alcohol solution from cyclohexane.

The transesterification reaction of 1,6-hexanediol and methyl acrylate was carried out at 85° C. until almost no methanol was distilled out, so that the transesterification reaction of 1,6-hexanediol and methyl acrylate was terminated to obtain a reaction mixture.

The obtained reaction mixture was heated to 88° C., and unreacted methyl acrylate was removed by azeotropic distillation with cyclohexane, to obtain 1285 g of crude 6-hydroxyhexyl acrylate.

Next, the obtained crude 6-hydroxyhexyl acrylate was collected by extraction, and further subjected to thin film distillation, to obtain 242 g of refined 6-hydroxyhexyl acrylate.

On the other hand, 200 g of the alcohol solution taken out from the decanter was heated to 80° C., and the degree of pressure reduction was gradually increased, and finally the degree of pressure reduction was adjusted to 250 kPa, to remove methanol by distillation. As a result, the amount of methanol removed by distillation was 115.9 g, and the amount of remaining 1,6-hexanediol was 83.3 g. Accordingly, it can be understood that methanol which is generated as a by-product in the transesterification of 1,6-hexanediol and methyl acrylate can be efficiently collected.

Additionally, the collected methanol was analyzed by gas chromatography, As a result, a notable peak attributed to methanol was observed, and slight peaks attributed to cyclohexane and methyl acrylate were also observed. Accordingly, it was confirmed that methanol which is a by-product having a relatively high purity can be easily collected, and that the methanol can be effectively used not only as a raw material for organic compound synthesis but also as a fuel.

From the above-mentioned results, it can be understood that according to the process for preparing a hydroxyalkyl acrylate of the present invention, not only it is made possible to efficiently collect the alcohol generated as a by-product at the time of preparing a hydroxyalkyl acrylate by a transesterification method, but also it is made possible to reuse a polyhydric alcohol separated from the by-product alcohol in the transesterification reaction of a polyhydric alcohol and an acrylic acid alkyl ester, to give a hydroxyalkyl acrylate.

Example VI of the Sixth Invention

In the following examples, each yield of a (meth)acrylate and an intended compound was calculated by the ratio of the amount of the actually generated (meth)acrylate to the theoretical generated amount of the intended (meth)acrylate.

In addition, the amounts of a raw material alcohol, a (meth)acrylic acid ester generated from the raw material alcohol, an azeotropic solvent, and methyl(meth)acrylate in the reaction mixtures in the following examples were calculated from area percentage by gas chromatography (hereinafter, referred to as GC) using a GC analyzer (detector: FID, column capillary DB-1: 30 m, manufactured by Agilent Technologies).

Example VI-1

A 20-stage Oldershaw distillation tower (theoretical number of stages: 15 stages) equipped with a reflux device at the tower top part and having a side tube and a 2 L four-necked flask having an air introduction tube were used as a reaction apparatus. The flask of the reaction apparatus was charged with 694 g (8.06 moles) of methyl acrylate, 552 g (6.20 moles) of N,N-dimethylaminoethanol, 1.76 g of phenothiazine, 22.1 g of dibutyltin oxide and 100 g of cyclohexane. While air was blown into the flask at a flow rate of 20 mL/min in the flask through the air introduction tube, a transesterification reaction was carried out. More specifically, the vapor taken out from the tower top of the distillation tower installed in the reaction apparatus was condensed, and a portion of the obtained condensate was refluxed to the tower top and the remaining condensate was removed outside of the reaction apparatus. The top temperature of the distillation tower was adjusted to 54 to 56° C., an azeotropic temperature of methyl alcohol and cyclohexane by adjusting the amount of the condensate to be removed outside of the reaction apparatus.

The condensate in an amount of 700 g removed from the tower top part of the distillation tower of the reaction apparatus and 200 g of water were mixed at 20° C. and the obtained mixed liquid was introduced into a decanter. The mixed liquid was separated into two layers of an upper layer and a lower layer. Methyl alcohol contained in the condensate was extracted with water and contained in the lower layer and cyclohexane contained in the condensate was contained in the upper layer of the extraction liquid.

The amount of the lower layer was 410 g, and the lower layer contained 47.0% by mass (193 g) of methyl alcohol, 0.5% by mass (2 g) of cyclohexane, 3.6% by mass (15 g) of methyl acrylate, and 48.9% by mass (200 g) of water.

On the other hand, the above-mentioned upper layer was supplied to the position of the tenth stage from the bottom of the distillation tower, which was the middle stage of the distillation tower, and was used effectively.

While cyclohexane was added to the flask as required so that the reaction temperature in the transesterification reaction of methyl acrylate and N,N-dimethylaminoethanol was kept at 85 to 102° C., the reaction was carried out. After 4 hours passed from starting of the reaction, the transesterification reaction was completed. After the completion of the reaction, the amount of methyl acrylate contained in the reaction mixture obtained by the transesterification reaction was 160 g.

After the completion of the reaction, the reaction mixture obtained by the transesterification reaction was further heated, and the reflux ratio was set to 10 to 15. The vapor was taken out from the tower top of the distillation tower, and the vapor was condensed, to give a condensate. At that time, cyclohexane was added to the flask so that the temperature of the reaction mixture in the flask was kept at 85 to 100° C. As the condensate was taken out from the tower top of the distillation tower, the top temperature of the distillation tower was gradually increased. The distillation was continued until the temperature at the top of the distillation tower reached 80° C., which is the boiling point of cyclohexane.

As a result, the content of methyl acrylate in the reaction mixture in the flask was not more than 0.1% by mass. The amount of the collected condensate which was taken out from the tower top was 490 g. The condensate contained 5 g of methanol, 145 g of methyl acrylate and 340 g of cyclohexane. The condensate contained almost all of methyl acrylate used in an excess amount. The collected condensate could be used in the transesterification of methyl acrylate and N,N-dimethylaminoethanol. Accordingly, it was confirmed that loss of methyl acrylate can be prevented by using the condensate in the transesterification reaction of methyl acrylate and N,N-dimethylaminoethanol.

As a result of preparation of N,N-dimethylaminoethyl acrylate in the above-mentioned manner, the amount of N,N-dimethylaminoethyl acrylate was 852 g (yield on the basis of N,N-dimethylaminoethanol: 96% by mass, yield on the basis of the charged amount of methyl acrylate: 73.8% by mass, and yield in the case of reusing methyl acrylate collected by azeotropy with cyclohexane after the completion of the reaction: 93.3% by mass).

From the above-mentioned results, according to Example VI-1, it can be understood that the upper layer obtained by mixing the condensate removed from the tower top part of the distillation tower of the reaction apparatus with water, separating the obtained mixed liquid, and supplying the separated upper layer to the distillation tower can be used effectively, and that the condensate obtained by further heating the reaction mixture obtained by the transesterification reaction and collected from the tower top of the distillation tower can be used effectively for a new transesterification reaction, and thus the intended N,N-dimethylaminoethyl acrylate can be prepared in a high yield.

Example VI-2

A 10-stage Oldershaw distillation tower (theoretical number of stages: 7 stages) equipped with a reflux device at the tower top part and having a side tube and a 1 L four-necked flask having an air introduction tube were used as a distillation apparatus. The lower layer obtained in Example VI-1 was charged to the flask of the reaction apparatus.

Distillation was carried out while setting the reflux ratio to 10 to 15 and a fraction A was collected at the time the tower top temperature was 64° C. or lower. As a result, the amount of the collected fraction A was 40 g, and the composition of the fraction A was 62.1% by mass (25 g) of methyl alcohol, 32.5% by mass (13 g) of methyl acrylate, 5.3% by mass (2 g) of cyclohexane, and 0.1% by mass of water. The fraction A could be used in the transesterification reaction of methyl acrylate and N,N-dimethylaminoethanol.

The above-mentioned distillation was continued while setting the reflux ratio to 5 to 10, and a fraction B was collected at the time the tower top temperature was 64 to 66° C. As a result, it was confirmed that the amount of the collected fraction B was 167 g, the composition of the fraction B was 99.9% by mass of methyl alcohol and 0.1% by mass of water, and no methyl acrylate was contained.

It was confirmed that the fraction B can be used effectively as an industrial raw material, a solvent or the like, since the fraction contains no component other than methyl alcohol and a trace of water. Furthermore, it was confirmed that no methyl acrylate was lost, since no methyl acrylate was detected in the fraction B, and thus no adverse influence would be caused on the yield of N,N-dimethylaminoethyl acrylate.

The composition of 203 g of the remaining liquid in the flask was 3% by mass of methyl alcohol and 97% by mass of water, and no other component was detected. Thus, the remaining liquid contained mainly water, so that the remaining liquid could be used as water when mixing the condensate and water in Example VI-1.

From the above-mentioned results, it can be understood that the lower layer obtained by mixing the condensate removed from the tower top part of the distillation tower of the reaction apparatus and collected in Example VI-1 with water and separating the obtained mixed liquid can be effectively used according to Example VI-2.

Example VI-3

The same reaction apparatus as that used in Example VI-1 was used. The flask of the reaction apparatus was charged with 517 g (6.00 moles) of methyl acrylate, 651 g (5.00 moles) of n-octyl alcohol, 1.76 g of phenothiazine, 0.72 g of tetramethyltitanium and 117 g of n-hexane. While air was blown into the flask at a flow rate of 20 mL/min in the flask through the air introduction tube, a transesterification reaction was carried out. More specifically, the vapor taken out from the tower top of the distillation tower installed in the reaction apparatus was condensed, and a portion of the obtained condensate was refluxed to the tower top, and the remaining condensate was removed outside of the reaction apparatus. The temperature at the top of the distillation tower was adjusted to 48 to 50° C. which was an azeotropic temperature of methyl alcohol and n-hexane by adjusting the amount of the condensate to be removed outside of the reaction apparatus.

The condensate in an amount of 549 g removed from the tower top part of the distillation tower of the reaction apparatus and 100 g of water were mixed at 20° C., and the obtained mixed liquid was introduced into a decanter. The mixed liquid was separated into two layers of an upper layer and a lower layer. Methyl alcohol contained in the condensate was contained in the lower layer by the extraction with water, and n-hexane contained in the condensate was contained in the upper layer of the extraction liquid.

The amount of the lower layer was 257 g, and the lower layer contained 56.4% by mass (145 g) of methyl alcohol, 1.6% by mass (4 g) of n-hexane, 3.1% by mass (8 g) of methyl acrylate, and 38.9% by mass (100 g) of water.

On the other hand, the upper layer was used effectively by supplying to the position of the tenth stage from the bottom of the distillation tower which was the middle stage of the distillation tower.

The reaction temperature in the transesterification reaction of methyl acrylate and n-octyl alcohol was 90 to 110° C., and the transesterification reaction was completed after 8 hours passed from the starting of the reaction. After the completion of the reaction, the amount of methyl acrylate contained in the reaction mixture obtained by the transesterification reaction was 86 g.

After the completion of the reaction, the reaction mixture obtained by the transesterification reaction was further heated. The reflux ratio was set to 10 to 15, and vapor was taken out from the tower top of the distillation tower. The vapor was condensed to give a condensate. At that time, n-hexane was added to the flask as required so that the temperature of the reaction mixture in the flask was kept at 90 to 110° C. As the condensate was taken out from the tower top of the distillation tower, the top temperature of the distillation tower was gradually increased. The distillation was continued until the top temperature of the distillation tower reached 68° C., which is the boiling point of n-hexane.

As a result, the content of methyl acrylate in the reaction mixture in the flask was not more than 0.2% by mass. Furthermore, the amount of the collected condensate taken out from the tower top was 392 g, and the condensate contained 3.8% by mass (15 g) of methanol, 18.6% by mass (73 g) of methyl acrylate, and 77.6% by mass (304 g) of n-hexane. The condensate contained almost all of methyl acrylate used in an excess amount. The collected condensate could be used in the transesterification reaction of methyl acrylate and n-octyl alcohol. Accordingly, it was confirmed that loss of methyl acrylate can be prevented by using the condensate in the transesterification reaction of methyl acrylate and n-octyl alcohol.

As a result of preparing n-octyl acrylate in the above-mentioned manner, the amount of n-octyl acrylate was 912 g (yield on the basis of n-octyl alcohol: 99.0% by mass, yield on the basis of the charged amount of methyl acrylate: 82.5% by mass, and yield in the case of reusing methyl acrylate collected by azeotropy with n-hexane after the completion of the reaction: 96.0% by mass).

Example VI-4

A 10-stage Oldershaw distillation tower (theoretical number of stages: 7 stages) equipped with a reflux device at the tower top part and having a side tube and a 2 L four-necked flask having an air introduction tube were used as a distillation apparatus. The flask of the reaction apparatus was charged with the lower layer obtained in Example VI-3.

Distillation was carried out while setting the reflux ratio to 10 to 15, and a fraction A was collected at the time the tower top temperature was 64° C. or lower. As a result, the amount of the collected fraction A was 32 g, and the composition of the fraction A was 62.5% by mass (20 g) of methyl alcohol, 25.0% by mass (8 g) of methyl acrylate, 12.5% by mass (4 g) of n-hexane, and 0.1% by mass of water. The fraction A could be used in the transesterification reaction of methyl acrylate and n-octyl alcohol.

The distillation was continued while setting the reflux ratio to 5 to 10 and a fraction B was collected at the time the tower top temperature was 64 to 66° C. As a result, it was confirmed that the amount of the collected fraction B was 122 g, the composition of the fraction B was 99.9% by mass (122 g) of methyl alcohol and 0.1% by mass of water, and no methyl acrylate was contained.

It was confirmed that the fraction B can be used effectively as an industrial raw material, a solvent or the like, since the fraction contains no component other than methyl alcohol and a trace of water. Furthermore, it was confirmed that no methyl acrylate was lost since no methyl acrylate was detected in the fraction B, and thus no adverse influence would be caused on the yield of n-octyl acrylate.

The composition of 103 g of the remaining liquid in the flask was 3% by mass (3 g) of methyl alcohol and 97% by mass (100 g) of water and no other component was detected. Thus, the remaining liquid contained mainly water, so that the remaining liquid could be used as water when mixing the condensate and water in Example VI-3.

Example VI-5

The same reaction apparatus as used in Example VI-1 was used. The flask of the reaction apparatus was charged with 430 g (5.0 moles) of methyl acrylate, 675 g (7.5 moles) of 1,4-butanediol, 0.72 g of phenothiazine, 3.6 g of dioctyltin oxide, and 100 g of cyclohexane. While air was blown into the flask at a flow rate of 20 mL/min in the flask through the air introduction tube, a transesterification reaction was carried out. More specifically, the vapor taken out from the tower top of the distillation tower installed in the reaction apparatus was condensed, and a portion of the obtained condensate was refluxed to the tower top. The remaining condensate was removed outside of the reaction apparatus. The temperature at the top of the distillation tower was adjusted to 54 to 56° C. which was an azeotropic temperature of methyl alcohol and cyclohexane by adjusting the amount of the condensate to be removed from the reaction apparatus.

The condensate in an amount of 490 g removed from the tower top part of the distillation tower of the reaction apparatus and 140 g of water were mixed at 20° C., and the obtained mixed liquid was introduced into a decanter. The mixed liquid was separated into two layers of an upper layer and a lower layer. Methyl alcohol contained in the condensate was contained in the lower layer by the extraction with water, and cyclohexane contained in the condensate was contained in the upper layer of the extraction liquid.

The amount of the lower layer was 303 g, and the lower layer contained 48.7% by mass (148 g) of methyl alcohol, 1.6% by mass (5 g) of cyclohexane, 3.3% by mass (10 g) of methyl acrylate, and 46.4% by mass (140 g) of water.

On the other hand, the upper layer was effectively used by supplying to the position of the tenth stage from the bottom of the distillation tower which was the middle stage of the distillation tower.

While cyclohexane was added to the flask as required so that the reaction temperature in the transesterification reaction of methyl acrylate and 1,4-butanediol was kept at 85 to 100° C., the reaction was carried out. After 8 hours passed from the starting of the reaction, the transesterification reaction was completed. After the completion of the reaction, the amount of methyl acrylate contained in the reaction mixture obtained by the transesterification reaction was 20 g.

After the completion of the reaction, the reaction mixture obtained by the transesterification reaction was further heated, the reflux ratio was set to 10 to 15, vapor was taken out from the tower top of the distillation tower, and the vapor was condensed to give a condensate. At that time, cyclohexane was added to the flask so that the temperature of the reaction mixture in the flask was kept at 85 to 100° C. As the condensate was taken out from the tower top of the distillation tower, the top temperature of the distillation tower was gradually increased. The distillation was continued until the top temperature of the distillation tower reached 80° C. which is the boiling point of cyclohexane.

As a result, the content of methyl acrylate in the reaction mixture in the flask was not more than 0.2% by mass. Furthermore, the amount of the collected condensate taken out from the tower top was 75 g, the condensate contained 5 g of methanol, 10 g of methyl acrylate, and 60 g of cyclohexane. The condensate contained almost all of methyl acrylate used in an excess amount. The collected condensate could be used in the transesterification reaction of methyl acrylate and 1,4-butanediol. Accordingly, it was confirmed that loss of methyl acrylate can be prevented by using the condensate in the transesterification reaction of methyl acrylate and 1,4-butanediol.

As a result of preparing 4-hydroxybutyl acrylate in the above-mentioned manner, the obtained reaction mixture contained 496 g of 4-hydroxybutyl acrylate, 131 g of 1,4-butanediol diacrylate, and 305 g of 1,4-butanediol. 4-Hydroxybutyl acrylate contained in the reaction mixture could be separated by extraction of the reaction mixture, distillation or adsorption using an adsorption tower.

Example VI-6

A 10-stage Oldershaw distillation tower (theoretical number of stages: 7 stages) equipped with a reflux device at the tower top part and having a side tube and a 1 L four-necked flask having an air introduction tube were used as a distillation apparatus. The flask of the reaction apparatus was charged with the lower layer obtained in Example VI-5.

Distillation was carried out while setting the reflux ratio to 10 to 15 and a fraction A was collected at the time the tower top temperature was 64° C. or lower. As a result, the amount of the collected fraction A was 42 g, and the composition of the fraction A was 64.3% by mass (27 g) of methyl alcohol, 23.8% by mass (10 g) of methyl acrylate, 12.5% by mass (5 g) of cyclohexane, and 0.1% by mass (0.04 g) of water. The fraction A could be used in the transesterification reaction of methyl acrylate and 1,4-butanediol.

The distillation was continued while setting the reflux ratio to 5 to 10 and a fraction B was collected at the time the tower top temperature was 64 to 65° C. As a result, it was confirmed that the amount of the collected fraction B was 118 g, the composition of the fraction B was 99.9% by mass of methyl alcohol and 0.1% by mass of water, and no methyl acrylate was contained.

It was confirmed that the fraction B can be used effectively as an industrial raw material, a solvent or the like, since the fraction contains no component other than methyl alcohol and a trace of water. Furthermore, it was confirmed that no methyl acrylate was lost, since no methyl acrylate was detected in the fraction B, and thus no adverse influence would be caused on the yield of 4-hydroxybutyl acrylate.

The composition of 142 g of the remaining liquid in the flask was 3% by mass of methyl alcohol and 97% by mass of water, and no other component was detected. Thus, the remaining liquid contained mainly water, so that the remaining liquid could be used as water when mixing the condensate and water in Example VI-5.

Example VI-7

The transesterification reaction was carried out in the same manner as in Example VI-1, except that 780.9 g (7.80 moles) of methyl methacrylate, 372.4 g (6.00 moles) of N,N-dimethylaminoethanol, and 1.89 g of phenothiazine were charged to the same reaction apparatus as used in Example VI-1. After the completion of the reaction, the amount of methyl acrylate contained in the reaction mixture obtained by the transesterification reaction was 178 g.

After cyclohexane was added to the flask, and 175 g of unreacted methyl methacrylate was collected. The content of methyl methacrylate in the reaction mixture in the flask was weighed. As a result, it was found that the content of methyl methacrylate was not more than 0.1% by mass.

Next, the lower layer in the decanter was distilled in the same manner as in Example VI-2, to give 5 g of a fraction A. The composition of the fraction A was 86.9% by mass of methyl alcohol, 13.0% by mass of cyclohexane, and 0.1% by mass of water. The fraction A could be used in the transesterification reaction of methyl methacrylate and N,N-dimethylaminoethanol. Successively, a fraction B was collected in the same manner as in Example VI-2, and its composition was analyzed to find that the composition of the fraction B was 99.9% by mass of methyl alcohol and 0.1% by mass of water.

Example VI-8

The transesterification reaction was carried out in the same manner as in Example VI-1, except that 1041.2 g (10.4 moles) of methyl methacrylate, 248.3 g (4.00 moles) of ethylene glycol, 1.59 g of phenothiazine, and 0.96 g of lithium hydroxide were charged to the same reaction apparatus as that used in Example VI-1. After the completion of the reaction, the amount of methyl methacrylate contained in the reaction mixture obtained by the transesterification reaction was 235 g.

After cyclohexane was added to the flask and 233 g of unreacted methyl methacrylate was collected, the content of methyl methacrylate in the reaction mixture in the flask was examined. As a result, it was found that the content of methyl methacrylate was not more than 0.1% by mass.

Next, the lower layer in the decanter was distilled in the same manner as in Example VI-2, to give 5 g of a fraction A. The composition of the fraction A was 86.9% by mass of methyl alcohol, 13.0% by mass of cyclohexane, and 0.1% by mass of water. The fraction A could be used in the transesterification reaction of methyl methacrylate and ethylene glycol. Successively, a fraction B was collected in the same manner as in Example VI-2, and its composition was analyzed to find that the composition of the fraction B was 99.9% by mass of methyl alcohol and 0.1% by mass of water.

Example VI-9

The transesterification reaction was carried out in the same manner as in Example VI-1, except that 633.2 g (6.20 moles) of tetrahydrofurfuryl alcohol was used in place of N,N-dimethylaminoethanol in Example VI-1. After the completion of the reaction, the amount of methyl acrylate contained in the reaction mixture obtained by the transesterification reaction was 147 g.

After cyclohexane was added to the flask, and 146 g of unreacted methyl acrylate was collected, the content of methyl acrylate in the reaction mixture in the flask was examined. As a result, it was found that the content of methyl acrylate was not more than 0.1% by mass.

Next, the lower layer in the decanter was distilled in the same manner as in Example VI-2. As a result, the composition of the fraction A was 62.3% by mass of methyl alcohol, 32.1% by mass of methyl acrylate, 5.5% by mass of cyclohexane, and 0.1% by mass of water. The fraction A could be used in the transesterification reaction of methyl acrylate and tetrahydrofurfuryl alcohol. Successively, a fraction B was collected in the same manner as in Example VI-2 and its composition was analyzed. As a result, it was found that the composition of the fraction B was 99.9% by mass of methyl alcohol and 0.1% by mass of water, and it was confirmed that no methyl acrylate was contained.

Example VI-10

The transesterification reaction was carried out in the same manner as in Example VI-1, except that 805.0 g (6.00 moles) of diethylene glycol monoethyl ether was used in place of N,N-dimethylaminoethanol in Example VI-1. After the completion of the reaction, the amount of methyl acrylate contained in the reaction mixture obtained by the transesterification reaction was 140 g.

After cyclohexane was added to the flask, and 138 g of unreacted methyl acrylate was collected, the content of methyl acrylate in the reaction mixture in the flask was examined. As a result, it was found that the content of methyl acrylate was not more than 0.1% by mass.

Next, the lower layer in the decanter was distilled in the same manner as in Example VI-2. As a result, the composition of the fraction A was 62.3% by mass of methyl alcohol, 32.3% by mass of methyl acrylate, 5.3% by mass of cyclohexane, and 0.1% by mass of water. The fraction A could be used in the transesterification reaction of methyl acrylate and diethylene glycol monoethyl ether. Successively, a fraction B was collected in the same manner as in Example VI-2 and its composition was analyzed. As a result, it was found that the composition of the fraction B was 99.9% by mass of methyl alcohol and 0.1% by mass of water and it was confirmed that no methyl acrylate was contained.

Example VI-11

The transesterification reaction was carried out in the same manner as in Example VI-1, except that 894.8 g (5.20 moles) of methyl acrylate, 472.7 g (4.00 moles) of 1,6-hexanediol and 3.7 g of dioctyltin oxide were used in Example VI-1. After the completion of the reaction, the amount of methyl acrylate contained in the reaction mixture obtained by the transesterification reaction was 189 g.

After cyclohexane was added to the flask, and 188 g of unreacted methyl acrylate was collected, the content of methyl acrylate in the reaction mixture in the flask was examined. As a result, it was found that the content of methyl acrylate was not more than 0.1% by mass.

Next, the lower layer in the decanter was distilled in the same manner as in Example VI-2. As a result, the composition of the fraction A was 62.1% by mass of methyl alcohol, 32.4% by mass of methyl acrylate, 5.4% by mass of cyclohexane, and 0.1% by mass of water. The fraction A could be used in the transesterification reaction of methyl acrylate and 1,6-hexanediol. Successively, a fraction B was collected in the same manner as in Example VI-2 and its composition was analyzed. As a result, it was found that the composition of the fraction B was 99.9% by mass of methyl alcohol and 0.1% by mass of water and it was confirmed that no methyl acrylate was contained.

Example VI-12

The transesterification reaction was carried out in the same manner as in Example VI-1, except that 1006.7 g (11.7 moles) of methyl acrylate, 402.5 g (3.00 moles) of trimethylolpropane and 8.4 g of dioctyltin oxide were used in Example VI-1. After the completion of the reaction, the amount of methyl acrylate contained in the reaction mixture obtained by the transesterification reaction was 216 g.

After cyclohexane was added to the flask and 214 g of unreacted methyl acrylate was collected, the content of methyl acrylate in the reaction mixture in the flask was examined. As a result, it was found that the content of methyl acrylate was not more than 0.1% by mass.

Next, the lower layer in the decanter was distilled in the same manner as in Example VI-2. As a result, the composition of the fraction A was 62.1% by mass of methyl alcohol, 32.3% by mass of methyl acrylate, 5.5% by mass of cyclohexane, and 0.1% by mass of water. The fraction A could be used in the transesterification reaction of methyl acrylate and trimethylolpropane. Successively, a fraction B was collected in the same manner as in Example VI-2 and its composition was analyzed. As a result, it was found that the composition of the fraction B was 99.9% by mass of methyl alcohol and 0.1% by mass of water and it was confirmed that no methyl acrylate was contained.

Example VI-13

The transesterification reaction was carried out in the same manner as in Example VI-1, except that 559.3 g (6.5 moles) of methyl acrylate, 1041.5 g (5.00 moles) of 2-ethyl-2-methyl-1,3-dioxolane-4-methanol and 4.7 g of dioctyltin oxide were used in Example VI-1. After the completion of the reaction, the amount of methyl acrylate contained in the reaction mixture obtained by the transesterification reaction was 117 g.

After cyclohexane was added to the flask, and 116 g of unreacted methyl acrylate was collected, the content of methyl acrylate in the reaction mixture in the flask was examined. As a result, it was found that the content of methyl acrylate was not more than 0.1% by mass.

Next, the lower layer in the decanter was distilled in the same manner as in Example VI-2. As a result, the composition of the fraction A was 62.5% by mass of methyl alcohol, 32.1% by mass of methyl acrylate, 5.3% by mass of cyclohexane, and 0.1% by mass of water. The fraction A could be used in the transesterification reaction of methyl acrylate and 2-ethyl-2-methyl-1,3-dioxolane-4-methanol. Successively, a fraction B was collected in the same manner as in Example VI-2 and its composition was analyzed. As a result, it was found that the composition of the fraction B was 99.9% by mass of methyl alcohol and 0.1% by mass of water and it was confirmed that no methyl acrylate was contained.

Example VI-14

The transesterification reaction was carried out in the same manner as in Example VI-1, except that 615.2 g (7.15 moles) of methyl acrylate, 892.1 g (5.50 moles) of 3-ethyl-3-oxetanylmethyl alcohol and 5.1 g of dioctyltin oxide were used in Example VI-1. After the completion of the reaction, the amount of methyl acrylate contained in the reaction mixture obtained by the transesterification reaction was 123 g.

After cyclohexane was added to the flask, and 122 g of unreacted methyl acrylate was collected, the content of methyl acrylate in the reaction mixture in the flask was examined. As a result, it was found that the content of methyl acrylate was not more than 0.1% by mass.

Next, the lower layer in the decanter was distilled in the same manner as in Example VI-2. As a result, the composition of the fraction A was 62.3% by mass of methyl alcohol, 32.1% by mass of methyl acrylate, 5.5% by mass of cyclohexane, and 0.1% by mass of water. The fraction A could be used in the transesterification reaction of methyl acrylate and 3-ethyl-3-oxetanylmethyl alcohol. Successively, a fraction B was collected in the same manner as in Example VI-2 and its composition was analyzed. As a result, it was found that the composition of the fraction B was 99.9% by mass of methyl alcohol and 0.1% by mass of water and it was confirmed that no methyl acrylate was contained.

Comparative Example VI-1

The same reaction apparatus as that used in Example VI-1 was used. The flask of the reaction apparatus was charged with 694 g (8.06 moles) of methyl acrylate, 552 g (6.20 moles) of N,N-dimethylaminoethanol, 1.76 g of phenothiazine, 22.1 g of dibutyltin oxide and 100 g of isohexane.

While air was blown into the flask at a flow rate of 20 mL/min in the flask, a transesterification reaction was carried out at a reaction temperature of 76 to 93° C. More specifically, the vapor taken out from the tower top of the distillation tower installed in the reaction apparatus was condensed, and a portion of the obtained condensate was refluxed to the tower top. The remaining condensate was removed from the reaction apparatus. The top temperature of the distillation tower was adjusted to 45 to 46° C. which was an azeotropic temperature of methyl alcohol and isohexane by adjusting the amount of the condensate to be removed outside of the reaction apparatus.

The condensate in an amount of 950 g removed from the reaction apparatus, 200 g of water were mixed at 20° C. and the obtained mixed liquid was introduced into a decanter and separated into two layers. As a result, methyl alcohol contained in the condensate was contained in the lower layer of the two layers. On the other hand, the upper layer contained isohexane, and was supplied to the tenth stage from the bottom, which was the middle stage of the distillation tower.

The reaction of methyl acrylate and N,N-dimethylaminoethanol was carried out for 13 hours, to complete the transesterification reaction of methyl acrylate and N,N-dimethylaminoethanol.

After the completion of the transesterification reaction, the amount of methyl acrylate remaining in the reaction apparatus was 160 g.

Next, isohexane was added to the flask so that the temperature of the reaction mixture in the flask was kept at 80 to 90° C., and at the same time the reflux ratio was set to 10 to 15. The condensate was taken out from the tower top. When the condensate was taken out from the tower top, the tower top temperature quickly reached 62° C. which was a boiling point of isohexane. The amount of the condensate taken out from the tower top was 300 g.

As a result, the remaining amount of methyl acrylate in the reaction apparatus was 10.8% by mass. Furthermore, 5 g of methanol, 5 g of methyl acrylate and 290 g of isohexane were contained in 300 g of the condensate taken out from the tower top. Accordingly, methyl acrylate used as a raw material was scarcely contained in the condensate It was confirmed that almost all of methyl acrylate remained in the reaction apparatus.

From the above-mentioned results, the amount of methyl acrylate remaining in the reaction apparatus on completion of the reaction was 160 g. In addition, in the process after the completion of the reaction, methyl acrylate was not azeotropically boiled with isohexane and collected only in an amount of 5 g.

Comparative Example VI-2

A 20-stage Oldershaw distillation tower (theoretical number of stages: 15 stages) equipped with a reflux device at the tower top part and having a side tube and a 2 L four-necked flask having an air introduction tube were used as a reaction apparatus. The flask of the reaction apparatus was charged with 694 g (8.06 moles) of methyl acrylate, 552 g (6.20 moles) of N,N-dimethylaminoethanol, 1.76 g of phenothiazine, 22.1 g of dibutyltin oxide and 100 g of cyclohexane. While air was blown into the flask at a flow rate of 20 mL/min in the flask through the air introduction tube, a transesterification reaction was carried out.

Specifically, the vapor taken out from the tower top of the distillation tower installed in the reaction apparatus was condensed, and a portion of the obtained condensate was refluxed to the tower top. The remaining condensate was removed from the reaction apparatus. The temperature at the top of the distillation tower was adjusted to 54 to 56° C. which was an azeotropic temperature of methyl alcohol and cyclohexane by adjusting the amount of the condensate to be removed outside of the reaction apparatus.

The condensate in an amount of 700 g removed from the tower top part of the distillation tower of the reaction apparatus and 200 g of water were mixed at 20° C., and the obtained mixed liquid was introduced into a decanter. The mixed liquid was separated into two layers of an upper layer and a lower layer. Methyl alcohol contained in the condensate was extracted with water and contained in the lower layer and cyclohexane contained in the condensate was contained in the upper layer of the extraction liquid. The amount of the lower layer was 410 g, and the lower layer contained 47.0% by mass (193 g) of methyl alcohol, 0.5% by mass (2 g) of cyclohexane, 3.6% by mass (15 g) of methyl acrylate, and 48.9% by mass (200 g) of water.

While cyclohexane was added to the flask as required so that the reaction temperature in the transesterification reaction of methyl acrylate and N,N-dimethylaminoethanol was kept at 85 to 102° C., the reaction was carried out until 4 hours passed from the starting of the reaction, and the transesterification reaction was completed.

As a result, the yield of N,N-dimethylaminoethyl acrylate was 96.0% by mass and the yield based on methyl acrylate was 73.8% by mass. The composition of the water layer obtained by extracting methanol from the condensate was 48.0% by mass of methanol, 0.1% by mass of n-hexane, and 3.6% by mass of methyl acrylate and the remaining amount of methyl acrylate in the reaction apparatus was 160 g.

Consequently, it can be understood that a large quantity of methyl acrylate remains in the reaction apparatus by the method of Comparative Example VI-2

From the above-mentioned results, it can be understood that according to each example in Examples VI of the present invention, it was made possible not only to efficiently collect a (meth)acrylate remaining after the transesterification reaction of methyl(meth)acrylate and an alcohol, but also it is made possible to reuse the collected methyl (meth)acrylate when carrying out the transesterification reaction of methyl(meth)acrylate and an alcohol.

Example VII of the Seventh Invention

In the following examples, each yield of a (meth)acrylate and an intended compound was calculated by the ratio of the amount of the actually generated (meth)acrylate to the theoretical generated amount of the intended (meth)acrylic acid ester on the basis of alcohol. Furthermore, the respective yields of methyl alcohol, cyclohexane, isohexane and methyl (meth)acrylate were calculated by area percentage by gas chromatography (hereinafter, referred to as GC) using a GC analyzer (detector: FID, column capillary DB-1: 30 m, manufactured by Agilent Technologies).

Example VII-1

To a 2 L four-necked glass flask were attached a 20-stage Oldershaw, a reflux condenser, and an air introduction tube, and the flask was charged with 694 g (8.06 moles) of methyl acrylate, 552 g (6.20 moles) of N,N-dimethylaminoethyl alcohol, 1.76 g of phenothiazine as a polymerization inhibitor, 22.1 g of dibutyltin oxide as a catalyst for transesterification, and 20 g of isohexane and 60 g of cyclohexane as reaction solvents. While a nitrogen gas containing 8% by volume of oxygen gas was blown into the flask at a flow rate of 20 mL/min to the flask, the contents in the flask were heated to 83 to 94° C., and a transesterification reaction was started under the atmospheric pressure.

The reflux ratio in the tower top was adjusted so that the top temperature of the distillation tower was kept at 45 to 46° C. which was an azeotropic temperature of methyl alcohol as a by-product and isohexane used as a reaction solvent. The condensate distilled out of the system from the tower top was cooled to 20° C. and led to a decanter.

Of the two layers separated in the decanter, the upper layer, which was a layer containing mainly isohexane, was refluxed to the tenth stage from the bottom of the distillation tower. The lower layer containing mainly methyl alcohol was continuously taken out so that the separation interface in the decanter was kept constant. Since the lower layer taken out contained isohexane besides methyl alcohol, in order to prevent decrease of isohexane in the reaction system, the reaction temperature was adjusted to 83 to 94° C. while isohexane in the same amount as that contained in the taken lower layer was added to the reaction system. The transesterification reaction of methyl acrylate and N,N-dimethylaminoethyl alcohol was completed within about 12 hours from the start of the reaction.

The amount of the generated N,N-dimethylaminoethyl acrylate was 852 g (yield: 96%), and the total concentration of Michael addition products in the reaction solution was not more than 0.02% by mass. Further, the lower layer containing mainly methyl alcohol and taken out in the reaction contained 54.7% by mass of methyl alcohol, 0.6% by mass of cyclohexane, and 44.7% by mass of isohexane, and the amount of methyl acrylate was not more than the detection limit (detection limit: 10 ppm).

Next, by using the distillation tower having a 10-stage Oldershaw, the lower layer was distilled. When a fraction having a boiling point of 45 to 50° C. was taken out from the tower top of the distillation tower, the fraction contained 82% by weight of isohexane, 17.6% by weight of methyl alcohol, and 0.4% by mass of cyclohexane. This fraction could be used as a reaction solvent. The remaining liquid in the flask contained 99.6% by weight of methyl alcohol, 0.3% by weight of isohexane, and 0.1% by weight of cyclohexane.

Example VII-2

To a 2 L four-necked glass flask were attached a 20-stage Oldershaw, a reflux condenser and an air introduction tube, and the flask was charged with 781 g (6.00 moles) of 2-ethylhexyl alcohol, 672 g (7.80 moles) of methyl acrylate, 0.55 g of 4-acetamino-2,2,6,6-tetramethylpiperidine-N-oxyl, 2.1 g of tetramethoxytitanium as a catalyst for transesterification, and 20 g of isohexane and 80 g of cyclohexane as reaction solvents. While a nitrogen gas containing 8% by volume of oxygen gas was blown into the flask at a flow rate of 20 mL/min to the flask, the contents in the flask were heated to 90 to 110° C. and a transesterification reaction was started under the atmospheric pressure.

The reflux ratio in the tower top was adjusted so that the top temperature of the distillation tower was kept at 45 to 46° C., an azeotropic temperature of methyl alcohol as a by-product and isohexane as a reaction solvent. The condensate distilled out of the system from the tower top was cooled to 20° C., and led to a decanter.

Of the two layers separated in the decanter, the upper layer, which was a layer containing mainly isohexane, was refluxed to the tenth stage from the bottom of the distillation tower. The lower layer containing mainly methyl alcohol was continuously taken out so that the separation interface in the decanter was kept constant. Since the lower layer taken out contained isohexane besides methyl alcohol, in order to prevent decrease of isohexane in the reaction system, the reaction temperature was adjusted to 90 to 110° C. while isohexane in the same amount as that contained in the taken lower layer was added to the reaction system. The transesterification reaction of methyl acrylate and 2-ethylhexyl alcohol was completed within about 6 hours from the start of the reaction.

The amount of the generated 2-ethylhexyl acrylate was 1078 g (yield: 98%), and the total concentration of Michael addition products in the reaction solution was not more than 0.05% by mass. Further, the lower layer containing mainly methyl alcohol and taken out at the time of the reaction contained 54.7% by mass of methyl alcohol, 0.6% by mass of cyclohexane, and 44.7% by mass of isohexane, and the amount of methyl acrylate was not more than the detection limit (detection limit: 10 ppm).

Next, by using the distillation tower having a 10-stage Oldershaw, the lower layer was distilled. When a fraction with a boiling point of 45 to 50° C. was taken out from the tower top of the distillation tower, the fraction contained 82% by weight of isohexane, 17.6% by weight of methyl alcohol, and 0.4% by mass of cyclohexane. This fraction could be used as a reaction solvent. The remaining liquid in the flask contained 99.6% by weight of methyl alcohol, 0.3% by weight of isohexane, and 0.1% by weight of cyclohexane.

Example VII-3

To a 2 L four-necked glass flask were attached a 20-stage Oldershaw, a reflux condenser, and an air introduction tube, and the flask was charged with 659 g (7.00 moles) of benzyl alcohol, 783 g (9.1 moles) of methyl acrylate, 0.52 g of 4-acetamino-2,2,6,6-tetramethylpiperidine-N-oxyl, 1.1 g of tetramethoxytitanium, 20 g of isohexane and 80 g of cyclohexane. While a nitrogen gas containing 8% by volume of oxygen gas was blown into the flask at a flow rate of 20 mL/min to the flask, the contents in the flask were heated to 85 to 100° C., and a transesterification reaction was started under the atmospheric pressure.

The reflux ratio in the tower top was adjusted so that the top temperature of the distillation tower was kept at 45 to 46° C., an azeotropic temperature of methyl alcohol as a by-product and isohexane as a reaction solvent. The condensate distilled out of the system from the tower top was cooled to 20° C. and led to a decanter.

Of the two layers separated in the decanter, the upper layer, which was a layer containing mainly isohexane, was refluxed to the tenth stage from the bottom of the distillation tower. The lower layer containing mainly methyl alcohol was continuously taken out so that the separation interface in the decanter was kept constant. Since the lower layer taken out contained isohexane besides methyl alcohol, in order to prevent decrease of isohexane in the reaction system, the reaction temperature was adjusted to 85 to 100° C. while isohexane in the same amount as that contained in the taken lower layer was added to the reaction system. The transesterification reaction of methyl acrylate and benzyl alcohol was completed within about 8 hours from the start of the reaction.

The amount of the generated benzyl acrylate was 996 g (yield: 96%), and the total concentration of Michael addition products in the reaction solution was not more than 0.1% by mass. Further, the lower layer containing mainly methyl alcohol and taken out at the time of the reaction contained 55.0% by mass of methyl alcohol, 0.6% by mass of cyclohexane, and 44.4% by mass of isohexane, but the amount of methyl acrylate was not more than the detection limit (detection limit: 10 ppm).

Next, by using the distillation tower having a 10-stage Oldershaw, the lower layer was distilled. When a fraction with a boiling point of 45 to 50° C. was taken out from the tower top of the distillation tower, the fraction contained 82% by weight of isohexane, 17.6% by weight of methyl alcohol, and 0.4% by mass of cyclohexane. This fraction could be used as a reaction solvent. The remaining liquid in the flask contained 99.6% by weight of methyl alcohol, 0.3% by weight of isohexane, and 0.1% by weight of cyclohexane.

Example VII-4

To a 2 L four-necked glass flask were attached a 20-stage Oldershaw, a reflux condenser and an air introduction tube, and the flask was charged with 647 g (8.50 moles) of 2-methoxyethyl alcohol, 951 g (11.05 moles) of methyl acrylate, 0.6 g of 4-acetamino-2,2,6,6-tetramethylpiperidine-N-oxyl, 6.4 g of dibutyltin oxide, 20 g of isohexane and 60 g of cyclohexane. While a nitrogen gas containing 8% by volume of oxygen gas was blown into the flask at a flow rate of 20 mL/min to the flask, the contents in the flask were heated to 85 to 100° C., and a transesterification reaction was started under the atmospheric pressure.

The reflux ratio in the tower top was adjusted so that the top temperature of the distillation tower was kept at 45 to 46° C. which was an azeotropic temperature of methyl alcohol as a by-product and isohexane as a reaction solvent. The condensate distilled out of the system from the tower top was cooled to 20° C. and led to a decanter.

Of the two layers separated in the decanter, the upper layer, which was a layer containing mainly isohexane, was refluxed to the tenth stage from the bottom of the distillation tower. The lower layer containing mainly methyl alcohol was continuously taken out so that the separation interface in the decanter was kept constant. Since the lower layer taken out contained isohexane besides methyl alcohol, in order to prevent decrease of isohexane in the reaction system, the reaction temperature was adjusted to 85 to 100° C. while isohexane in the same amount as that contained in the taken lower layer was added to the reaction system. The transesterification reaction of methyl acrylate and 2-methoxyethyl alcohol was completed within about 12 hours from the start of the reaction.

The amount of the generated 2-methoxyethyl acrylate was 1051 g (yield: 95%) and the total concentration of Michael addition products in the reaction solution was not more than 0.1% by mass. Further, the lower layer containing mainly methyl alcohol and taken out at the time of the reaction contained 54.9% by mass of methyl alcohol, 0.6% by mass of cyclohexane, and 44.5% by mass of isohexane, and the amount of methyl acrylate was not more than the detection limit (detection limit: 10 ppm).

Next, by using the distillation tower having a 10-stage Oldershaw, the lower layer was distilled. When a fraction having a boiling point of 45 to 50° C. was taken out from the tower top of the distillation tower, the fraction contained 82% by weight of isohexane, 17.6% by weight of methyl alcohol, and 0.4% by weight of cyclohexane. This fraction could be used as a reaction solvent. The remaining liquid in the flask contained 99.6% by weight of methyl alcohol, 0.3% by weight of isohexane, and 0.1% by weight of cyclohexane.

Example VII-5

To a 2 L four-necked glass flask were attached a 20-stage Oldershaw, a reflux condenser and an air introduction tube, and the flask was charged with 616 g (7.0 moles) of tetrahydrofurfuryl alcohol, 911 g (9.1 moles) of methyl methacrylate, 0.6 g of 4-acetamino-2,2,6,6-tetramethylpiperidine-N-oxyl, 6.4 g of dibutyltin oxide, 30 g of isohexane, and 70 g of cyclohexane. While a nitrogen gas containing 8% by volume of oxygen gas was blown into the flask at a flow rate of 20 mL/min to the flask, the contents in the flask were heated to 85 to 100° C., and a transesterification reaction was started under the atmospheric pressure.

The reflux ratio in the tower top was adjusted so that the top temperature of the distillation tower was kept at 45 to 46° C., an azeotropic temperature of methyl alcohol as a by-product and isohexane as a reaction solvent. The condensate distilled out of the system from the tower top was cooled to 20° C. and led to a decanter.

Of the two layers separated in the decanter, the upper layer, which was a layer containing mainly isohexane, was refluxed to the tenth stage from the bottom of the distillation tower. The lower layer containing mainly methyl alcohol was continuously taken out so that the separation interface in the decanter was kept constant. Since the lower layer taken out contained isohexane besides methyl alcohol, in order to prevent decrease of isohexane in the reaction system, the reaction temperature was adjusted to 85 to 100° C. while isohexane in the same amount as that contained in the taken lower layer was added to the reaction system. The transesterification reaction of methyl acrylate and tetrahydrofurfuryl alcohol was completed within about 12 hours from the start of the reaction.

The amount of the generated tetrahydrofurfuryl methacrylate was 1039 g (yield: 95%) and the total concentration of Michael addition products in the reaction solution was not more than 0.1% by mass. Further, the lower layer containing mainly methyl alcohol and taken out at the time of the reaction contained 57.0% by mass of methyl alcohol, 0.5% by mass of cyclohexane, and 42.5% by mass of isohexane, and the amount of methyl methacrylate was not more than the detection limit (detection limit: 10 ppm).

Next, by using the distillation tower having a 10-stage Oldershaw, the lower layer was distilled. When a fraction with a boiling point of 45 to 50° C. was taken out from the tower top of the distillation tower, the fraction contained 82% by weight of isohexane, 17.6% by weight of methyl alcohol, and 0.4% by mass of cyclohexane. This fraction could be used as a reaction solvent. The remaining liquid in the flask contained 99.6% by weight of methyl alcohol, 0.3% by weight of isohexane, and 0.1% by weight of cyclohexane.

Example VII-6

To a 2 L four-necked glass flask were attached a 20-stage Oldershaw, a reflux condenser and an air introduction tube, and the flask was charged with 616 g (7.0 moles) of tetrahydrofurfuryl alcohol, 911 g (9.1 moles) of methyl methacrylate, 0.6 g of 4-acetamino-2,2,6,6-tetramethylpiperidine-N-oxyl, 6.4 g of dibutyltin oxide, 40 g of isohexane, and 60 g of cyclohexane. While a nitrogen gas containing 8% by volume of oxygen gas was blown into the flask at a flow rate of 20 mL/min to the flask, the contents in the flask were heated to 80 to 97° C. and a transesterification reaction was started under the atmospheric pressure.

The reflux ratio in the tower top was adjusted so that the top temperature of the distillation tower was kept at 45 to 46° C. which was an azeotropic temperature of methyl alcohol as a by-product and isohexane as a reaction solvent. The condensate distilled out of the system from the tower top was cooled to 20° C. and led to a decanter.

Of the two layers separated in the decanter, the upper layer, which was a layer containing mainly isohexane, was refluxed to the tenth stage from the bottom of the distillation tower. The lower layer containing mainly methyl alcohol was continuously taken out so that the separation interface in the decanter was kept constant. Since the lower layer taken out contained isohexane besides methyl alcohol, in order to prevent decrease of isohexane in the reaction system, the reaction temperature was adjusted to 85 to 100° C. while isohexane in the same amount as that contained in the taken lower layer was added to the reaction system. The transesterification reaction of methyl methacrylate and tetrahydrofurfuryl alcohol was completed within about 12 hours from the start of the reaction.

The amount of the generated tetrahydrofurfuryl methacrylate was 1039 g (yield: 95%), and the total concentration of Michael addition products in the reaction solution was not more than 0.1% by mass. Further, the lower layer containing mainly methyl alcohol and taken out at the time of the reaction contained 55.2% by mass of methyl alcohol, 0.3% by mass of cyclohexane, and 44.5% by mass of isohexane, and the amount of methyl acrylate was not more than the detection limit (detection limit: 10 ppm).

Next, by using the distillation tower having a 10-stage Oldershaw, the lower layer was distilled. When a fraction with a boiling point of 45 to 50° C. was taken out from the tower top of the distillation tower, the fraction contained 82% by weight of isohexane, 17.6% by weight of methyl alcohol, and 0.4% by mass of cyclohexane. This fraction could be used as a reaction solvent. The remaining liquid in the flask contained 99.6% by weight of methyl alcohol, 0.3% by weight of isohexane, and 0.1% by weight of cyclohexane.

Comparative Example VII-1

To a 2 L four-necked glass flask were attached a 30-stage Oldershaw, a reflux condenser, and an air introduction tube, and the flask was charged with 647 g (8.50 moles) of 2-methoxyethyl alcohol, 951 g (11.05 moles) of methyl acrylate, 0.6 g of 4-acetamino-2,2,6,6-tetramethylpiperidine-N-oxyl, 6.4 g of dibutyltin oxide and 200 g of cyclohexane. While a nitrogen gas containing 8% by volume of oxygen gas was blown into the flask at a flow rate of 20 mL/min to the flask, the contents in the flask were heated to 87 to 94° C. and a transesterification reaction was started under the atmospheric pressure.

The reflux ratio in the tower top was adjusted so that the top temperature of the distillation tower was kept at 54 to 56° C., an azeotropic temperature of methyl alcohol as a by-product and cyclohexane as a reaction solvent. The condensate distilled out of the system from the tower top was cooled to 20° C. and led to a decanter.

Of the two layers separated in the decanter, the upper layer, which was a layer containing mainly cyclohexane, was refluxed to the tenth stage from the bottom of the distillation tower. The lower layer containing mainly methyl alcohol was continuously taken out so that the separation interface in the decanter was kept constant. Since the lower layer taken out contained cyclohexane besides methyl alcohol, in order to prevent decrease of cyclohexane in the reaction system, the reaction temperature was adjusted to 87 to 94° C. while cyclohexane in the same amount as the amount of cyclohexane contained in the taken lower layer was added to the reaction system. The transesterification reaction of methyl acrylate and 2-methoxyethyl alcohol was completed within about 10 hours from the start of the reaction.

The amount of the generated 2-methoxyethyl acrylate was 1029 g (yield: 93%) and the total concentration of Michael addition products in the reaction solution was not more than 0.2% by mass. Further, the lower layer containing mainly methyl alcohol and taken out at the time of the reaction contained 61% by mass of methyl alcohol, 30% by mass of cyclohexane, and 9% by mass of methyl acrylate.

Comparative Example VII-2

To a 2 L four-necked glass flask were attached a 30-stage Oldershaw, a reflux condenser and an air introduction tube, and the flask was charged with 647 g (8.50 moles) of 2-methoxyethyl alcohol, 951 g (11.05 moles) of methyl acrylate, 0.6 g of 4-acetamino-2,2,6,6-tetramethylpiperidine-N-oxyl, 6.4 g of dibutyltin oxide, and 150 g of n-hexane. While a nitrogen gas containing 8% by volume of oxygen gas was blown into the flask at a flow rate of 20 mL/min to the flask, the contents in the flask were heated to 82 to 91° C., and a transesterification reaction was started under the atmospheric pressure.

The reflux ratio in the tower top was adjusted so that the top temperature of the distillation tower was kept at 49 to 51° C., an azeotropic temperature of methyl alcohol as a by-product and n-hexane as a reaction solvent. The condensate distilled out of the system from the tower top was cooled to 20° C. and led to a decanter.

Of the two layers separated in the decanter, the upper layer, which was a layer containing mainly n-hexane, was refluxed to the tenth stage from the bottom of the distillation tower. The lower layer containing mainly methyl alcohol was continuously taken out so that the separation interface in the decanter was kept constant. Since the lower layer taken out contained n-hexane besides methyl alcohol, in order to prevent decrease of n-hexane in the reaction system, the reaction temperature was adjusted to 82 to 91° C. while n-hexane in the same amount as the amount of n-hexane contained in the taken lower layer was added to the reaction system. The transesterification reaction of methyl acrylate and 2-methoxyethyl alcohol was completed within about 11 hours from the start of the reaction.

The amount of the generated 2-methoxyethyl acrylate was 1040 g (yield: 94%) and the total concentration of Michael addition products in the reaction solution was not more than 0.2% by mass. Further, the lower layer containing mainly methyl alcohol and taken out at the time of the reaction contained 60% by mass of methyl alcohol, 35% by mass of n-hexane, and 5% by mass of methyl acrylate.

Comparative Example VII-3

To a 2 L four-necked glass flask were attached a 20-stage Oldershaw, a reflux condenser, and an air introduction tube, and the flask was charged with 647 g (8.50 moles) of 2-methoxyethyl alcohol, 951 g (11.05 moles) of methyl acrylate, 0.6 g of 4-acetamino-2,2,6,6-tetramethylpiperidine-N-oxyl, 6.4 g of dibutyltin oxide and 80 g of isohexane. While a nitrogen gas containing 8% by volume of oxygen gas was blown into the flask at a flow rate of 20 mL/min to the flask, the contents in the flask were heated to 72 to 82° C. and a transesterification reaction was started under the atmospheric pressure.

The reflux ratio in the tower top was adjusted so that the top temperature of the distillation tower was kept at 45 to 46° C., an azeotropic temperature of methyl alcohol as a by-product and isohexane as a reaction solvent. The condensate distilled out of the system from the tower top was cooled to 20° C. and led to a decanter.

Of the two layers separated in the decanter, the upper layer, which was a layer containing mainly isohexane, was refluxed to the tenth stage from the bottom of the distillation tower. The lower layer containing mainly methyl alcohol was continuously taken out so that the separation interface in the decanter was kept constant. Since the lower layer taken out contained isohexane besides methyl alcohol, in order to prevent decrease of isohexane in the reaction system, the reaction temperature was adjusted to 72 to 82° C. while isohexane in the same amount as the amount of isohexane contained in the taken lower layer was added to the reaction system. The transesterification reaction of methyl acrylate and 2-methoxyethyl alcohol was completed within about 17 hours from the start of the reaction.

The amount of the generated 2-methoxyethyl acrylate was 1040 g (yield: 94%) and the total concentration of Michael addition products in the reaction solution was not more than 0.2% by mass. Further, the lower layer containing mainly methyl alcohol and taken out at the time of the reaction contained 55% by mass of methyl alcohol and 45% by mass of isohexane, but no methyl acrylate.

Consequently, it can be understood that the method of Comparative Example VII-3 took a long time for carrying out the transesterification reaction of methyl acrylate and 2-methoxyethyl alcohol and is thus inferior in industrial production.

From the above-mentioned results, it can be understood that, according to the examples, the reaction temperature can be increased and thus the reaction time can be shortened at the time of preparing a (meth)acrylic acid ester by a transesterification method using methyl (meth)acrylate as a raw material since isohexane and cyclohexane are used in combination. Furthermore, it can be understood that, according to the examples, methyl alcohol taken out from the reaction system can be efficiently used as a raw material for a compound such as methyl (meth)acrylate, a solvent, a fuel and the like, since the methyl alcohol is scarcely contaminated with methyl(meth)acrylate as a raw material.

The invention claimed is:

1. A process for preparing 4-hydroxybutyl acrylate, which comprises carrying out a transesterification reaction of 1,4-butanediol and an alkyl acrylate in the presence of a catalyst for transesterification comprising a dialkyltin oxide having an alkyl group of 4 to 18 carbon atoms in an organic solvent, wherein the amount of the dialkyltin oxide having an alkyl group of 4 to 18 carbon atoms is controlled to 0.00001 to 0.01 moles per 1 mole of the alkyl acrylate, the organic solvent is an alicyclic hydrocarbon compound, and the amount of the alicyclic hydrocarbon compound is 5 to 200 parts by mass per 100 parts by mass of the total amount of 1,4-butanediol and the alkyl acrylate.

2. The process for preparing 4-hydroxybutyl acrylate according to claim 1, wherein the reaction mixture obtained by the transesterification reaction of 1,4-butanediol and the alkyl acrylate is mixed with an extractant comprising water and an aliphatic hydrocarbon compound, to extract 4-hydroxybutyl acrylate into a water layer, thereafter the water layer is mixed with an extractant comprising an aromatic hydrocarbon compound, to extract the 4-hydroxybutyl acrylate contained in the water layer to the aromatic hydrocarbon compound, and collecting the 4-hydroxybutyl acrylate.

3. The process for preparing 4-hydroxybutyl acrylate according to claim 1, wherein the dialkyltin oxide is collected from the reaction mixture comprising 4-hydroxybutyl acrylate, which is obtained by the transesterification reaction of 1,4-butanediol and the alkyl acrylate, and the collected dialkyltin oxide is reused as a catalyst for transesterification when the transesterification reaction of 1,4-butanediol and the alkyl acrylate is carried out.

4. The process for preparing 4-hydroxybutyl acrylate according to claim 1, wherein the alkyl acrylate is represented by the formula (I):

[Chem. 1]

$$CH_2=CHCOOR^1 \qquad (I)$$

wherein $R^1$ is an alkyl group having 1 to 4 carbon atoms.

5. The process for preparing 4-hydroxybutyl acrylate according to claim 2, wherein the dialkyltin oxide is collected from the reaction mixture comprising 4-hydroxybutyl acrylate, which is obtained by the transesterification reaction of 1,4-butanediol and the alkyl acrylate, and the collected dialkyltin oxide is reused as a catalyst for transesterification when the transesterification reaction of 1,4-butanediol and the alkyl acrylate is carried out.

6. The process for preparing 4-hydroxybutyl acrylate according to claim 2, wherein the alkyl acrylate is represented by the formula (I):

[Chem. 1]

$$CH_2=CHCOOR^1 \qquad (I)$$

wherein $R^1$ is an alkyl group having 1 to 4 carbon atoms.

7. The process for preparing 4-hydroxybutyl acrylate according to claim 3, wherein the alkyl acrylate is represented by the formula (I):

[Chem. 1]

$$CH_2=CHCOOR^1 \qquad (I)$$

wherein $R^1$ is an alkyl group having 1 to 4 carbon atoms.

8. The process for preparing 4-hydroxybutyl acrylate according to claim 1, wherein the alicyclic hydrocarbon compound is cyclohexane or methylcyclohexane.

* * * * *